United States Patent
Lee et al.

(10) Patent No.: US 10,464,919 B2
(45) Date of Patent: Nov. 5, 2019

(54) TRICYCLIC DERIVATIVE COMPOUND, METHOD FOR PREPARING SAME, AND PHARMACEUTICAL COMPOSITION COMPRISING SAME

(71) Applicant: Je Il Pharmaceutical Co., Ltd., Seoul (KR)

(72) Inventors: Hyunho Lee, Gyeonggi-do (KR); Kwangwoo Chun, Gyeonggi-do (KR); Bo-Young Joe, Chungcheongbuk-do (KR); Eun Seon Kim, Gyeonggi-do (KR); Eun Sung Jang, Gyeonggi-do (KR); Hyeongchan Oh, Gyeonggi-do (KR); Jeong-Min Kim, Gyeonggi-do (KR); Jiseon Park, Gyeonggi-do (KR); Hanchang Lee, Seoul (KR)

(73) Assignee: Je Il Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 15/579,692

(22) PCT Filed: Jun. 3, 2016

(86) PCT No.: PCT/KR2016/005911
§ 371 (c)(1),
(2) Date: Dec. 5, 2017

(87) PCT Pub. No.: WO2016/200101
PCT Pub. Date: Dec. 15, 2016

(65) Prior Publication Data
US 2018/0162834 A1    Jun. 14, 2018

(30) Foreign Application Priority Data

Jun. 9, 2015  (KR) .................. 10-2015-0081021

(51) Int. Cl.
| | |
|---|---|
| *C07D 401/06* | (2006.01) |
| *A61K 31/4375* | (2006.01) |
| *C07D 471/04* | (2006.01) |
| *A61K 31/497* | (2006.01) |
| *A61P 25/00* | (2006.01) |

(52) U.S. Cl.
CPC ........ *C07D 401/06* (2013.01); *A61K 31/4375* (2013.01); *A61K 31/497* (2013.01); *A61P 25/00* (2018.01); *C07D 471/04* (2013.01)

(58) Field of Classification Search
CPC ..... C07D 401/06; C07D 471/04; A61P 25/00; A61K 31/4375; A61K 31/497

USPC ......................................................... 514/285
See application file for complete search history.

(56) References Cited

U.S. PATENT DOCUMENTS

| | | |
|---|---|---|
| 5,391,554 A | 2/1995 | Showalter |
| 2007/0142430 A1 | 6/2007 | Peukert et al. |
| 2011/0218193 A1 | 9/2011 | Kim et al. |
| 2014/0350007 A1 | 11/2014 | Ye et al. |

FOREIGN PATENT DOCUMENTS

| | | |
|---|---|---|
| KR | 10-2009-0046431 | 5/2009 |
| KR | 10-2013-0089089 | 9/2013 |
| WO | WO 2003/080581 | 10/2003 |
| WO | 2005-123687 | 12/2005 |
| WO | WO 2009/053373 | 4/2009 |
| WO | 2009-061131 | 5/2009 |
| WO | 2010-056038 | 5/2010 |

OTHER PUBLICATIONS

International Search Report, ISA/KR, for PCT/KR2016/005911 (dated Nov. 23, 2016).
Curr Pharm Des., 13(9), 933-962, 2007.
BioEssays., 26(8), 882-893, 2004.
Nature, 434, 913-916, 2005.
Cancer Biology & Therapy, 4, 934-936, 2005.
Pharmacological Research, 52, 25-33, 2005.
Mol Cancer Ther, 2, 371-382, 2003.
Clin Cancer Res, 6, 2860-2867, 2000.
Cereb Blood Flow Metab., 17(11), 1143-1151, 1997.
Diabetes. 54(12), 3435-3441, 2005.
Biochimica et Biophysica Acta, 1846, -205, 2014.
Nature Reviews Drug Discovery, 11, 923-936, 2012.
EP Extended Search Report for EP App No. 16807741.0 dated Oct. 30, 2018 (6 pages).

*Primary Examiner* — Rita J Desai
(74) *Attorney, Agent, or Firm* — Fish & Richardson P.C.

(57) ABSTRACT

The present invention relates to novel tricyclic derivative compounds, and more specifically to tricyclic derivative compounds, optical isomers thereof, racemates thereof, or pharmaceutically acceptable salts thereof, which have excellent activity against PARP-1, tankyrase-1 or tankyrase-2. The tricyclic derivative compounds, optical isomers thereof, racemates thereof or pharmaceutically acceptable salts thereof according to the present invention have inhibitory activity against PARP-1, tankyrase-1, or tankyrase-2, and thus can be effectively used for the prevention or treatment of neuropathic pain, neurodegenerative diseases, cardiovascular diseases, diabetic neuropathy, inflammatory diseases, osteoporosis, or cancer.

11 Claims, No Drawings

TRICYCLIC DERIVATIVE COMPOUND, METHOD FOR PREPARING SAME, AND PHARMACEUTICAL COMPOSITION COMPRISING SAME

TECHNICAL FIELD

The present invention relates to tricyclic derivative compounds having excellent inhibitory activity against poly (ADP-ribose)polymerase, and more particularly to tricyclic derivative compounds having excellent inhibitory activity against PARP-1, tankyrase-1 or tankyrase-2, preparation methods thereof, and pharmaceutical compositions comprising the same.

BACKGROUND ART

The family of poly(ADP-ribose)polymerases (PARP) is composed of about 17 proteins, including PARP-1, PARP-2, PARP-3, PARP-4 (vPARP), PARP-5 (tankyrase-1, tankyrase-2), PARP-7, PARP-10 and the like [Curr Pharm Des., 13(9), 933-962, 2007]. These proteins all show a certain level of homology in their catalytic domain but differ in their cellular functions [BioEssays., 26(8), 882-893, 2004].

Among the many functions attributed to PARP-1 and PARP-2, its major role is to facilitate DNA repair by ADP-ribosylation and therefore coordinate a number of DNA repair proteins. Activation of PARP is induced by DNA single strand breaks after exposure to radiation, oxygen free radicals, or nitric oxide (NO), etc. DNA damage leads to PARP activation that repairs DNA single strand breaks, and thus PARP can contribute to resistance that may occur in various types in cancer therapy. Particularly, PARP inhibitors were reported to be useful for specific killing of tumors deficient in DNA double-strand repair factors such as BRCA-1 and BRCA-2, and thus have been developed as patient-specific anticancer agents against various types of cancers, including breast cancer, ovarian cancer, prostate cancer and the like, which have abnormalities in DNA double-strand damage repair factors [Nature, 434, 913-916, 2005; Cancer Biology & Therapy, 4, 934-936, 2005]. In addition, PARP inhibitors, when administered in combination, are known to enhance the efficacy of anticancer drugs that are used in conventional anticancer therapies [Pharmacological Research, 52, 25-33, 2005; Mol Cancer Ther, 2, 371-382, 2003; Clin Cancer Res, 6, 2860-2867, 2000]. Anticancer drugs that enhance the efficacy of PARP inhibitors include platinum compounds (cisplatin and carboplatin), topoisomerase inhibitors (irinotecan and topotecan), and temozolomide, etc.

Furthermore, it is known that inhibition of PARP enhances resistance to brain injury. When cerebral infarction occurs and cerebral blood vessels become clogged, oxygen in the cerebral blood vessels becomes deficient, and at this time, a large amount of glutamate is released and excessively activates glutamate receptor to produce an excessive amount of reactive oxygen species that damage DNA. It is considered that PARP activation caused by DNA damage in cerebral infarction rapidly consumes an excessive amount of NAD$^+$ to deplete energy in brain cells, causing ischemic brain injury [Cereb Blood Flow Metab., 17(11), 1143-1151, 1997]. PARP Inhibitors may be used for treatment of not only ischemic brain injury, but also various neurological diseases and cardiovascular diseases, including epilepsy, stroke, Alzheimer's disease, Parkinson's disease, amyotrophic lateral sclerosis (ALS), Huntington's disease, schizophrenia, chronic or acute pain, ischemic brain injury, neuronal loss after hypoxia, trauma, and nerve damage.

Furthermore, PARP inhibitors inhibit the production of inducible nitric oxide synthase (iNOS) in macrophages, P-selectin, and intercellular adhesion molecule-1 (ICAM-1) in endothelial cells. This activity becomes the basis of potent anti-inflammatory effects exhibited by PARP inhibitors. In addition, inhibition of PARP can reduce necrosis by preventing the translocation and penetration of neutrophils into damaged tissue. Therefore, PARP inhibitors are also useful for inflammatory symptoms. In recent years, the therapeutic potential of PARP inhibitors for treatment of diabetic neuropathy has been suggested [Diabetes. 54(12), 3435-3441, 2005].

Meanwhile, tankyrase-1 and tankyrase-2, also known as PARP-5, are known to be involved in Wnt/β-catenin signaling pathways, DNA repair processes, and mitosis which is highly related to the cell cycle [Biochimica et Biophysica Acta, 1846, 201-205, 2014]. In addition, tankyrase-1 and tankyrase-2 act as a positive regulator of telomere length that ADP-ribosylates TRF-1 to allow telomerase-mediated telomere elongation. Therefore, inhibition of tankyrase-1 and tankyrase-2 can inhibit Wnt/β-catenin signaling pathways, DNA repair processes and telomere elongation, thereby exhibiting anticancer effects through mechanisms different from those of PARP-1 [Nature Reviews Drug Discovery, 11, 923-936, 2012].

Accordingly, the present inventors have synthesized tricyclic derivative compounds as poly(ADP-ribose)polymerase (PARP)-1 inhibitors or tankyrase inhibitors, which may be used for treatment of various diseases caused by poly(ADP-ribose)polymerase (PARP) activity, and have found that the compounds exhibit excellent activity against PARP-1, tankyrase-1 or tankyrase-2, thereby completing the present invention.

DISCLOSURE

Technical Problem

It is an object of the present invention to provide tricyclic derivative compounds having excellent inhibitory activity against PARP-1, tankyrase-1 or tankyrase-2, and preparation methods thereof.

Another object of the present invention is to provide a pharmaceutical composition for prevention or treatment of various diseases caused by PARP-1, tankyrase-1 or tankyrase-2 activity, which contains the tricyclic derivative compound as an active ingredient.

Still another object of the present invention is to provide the use of the tricyclic derivative compound for manufacture of a medicament for prevention or treatment of various diseases caused by PARP-1, tankyrase-1 or tankyrase-2 activity.

Yet another object of the present invention is to provide a method for prevention or treatment of caused by PARP-1, tankyrase-1 or tankyrase-2 activity, which comprises administering the tricyclic derivative compound.

Technical Solution

In the present invention, tricyclic derivative compounds were synthesized, and it has been found that the derivative compounds inhibit PARP-1, tankyrase-1 or tankyrase-2 activity, and thus have significant effects on the treatment of various diseases caused by PARP-1, tankyrase-1 or tankyrase-2 activity, and are stable in vivo.

Tricyclic Derivative Compounds

The present invention provides tricyclic derivative compounds represented by the following formula 1, optical isomers thereof, racemates thereof, or pharmaceutically acceptable salts thereof:

[Formula 1]

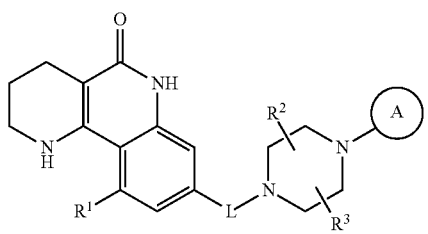

wherein
L is —CH$_2$— or —C(=O)—;
R$^1$ is H, a halogen atom, or C$_1$-C$_3$ alkoxy;
R$^2$ and R$^3$ are each independently H or C$_1$-C$_3$ alkyl, or R$^2$ and R$^3$ may be linked to each other to form a ring;
ring A is aryl or a heteroaryl containing 1 to 3 heteroatoms, wherein the aryl and the heteroaryl may be each independently unsubstituted, or one or more H atoms thereof may be substituted with a substituent selected from a halogen atom, —CN, —CF$_3$, —C$_1$-C$_3$ alkyl, —C$_1$-C$_3$ alkoxy, —CH$_2$—OR$^4$, —C(=O)—R$^4$, —C(=O)—OR$^4$, —S(=O)$_2$—R$^4$, —NH—C(=O)—R$^4$, —NO$_2$, —NR$^4$R$^5$ and —C(=O)—NR$^6$R$^7$;
R$^4$, R$^5$ and R$^6$ are each independently H or C$_1$-C$_3$ alkyl; and
R$^7$ is C$_1$-C$_3$ alkyl or C$_3$-C$_7$ cycloalkyl.

In the present invention, the halogen atom is preferably selected from among F, Cl and Br, but is not limited thereto.

In one embodiment of the present invention,
L may be —CH$_2$— or —C(=O)—;
R$^1$ may be H, a halogen atom or C$_1$-C$_3$ alkoxy;
R$^2$ and R$^3$ may be each independently H or C$_1$-C$_3$ alkyl, or R$^2$ and R$^3$ may be linked to each other to form a ring;
ring A may be aryl or a heteroaryl containing 1 to 3 heteroatoms, wherein one or more H atoms of the aryl may be substituted with a substituent selected from the group consisting of a halogen atom, —CN, —CF$_3$, —C$_1$-C$_3$ alkyl, —C$_1$-C$_3$ alkoxy, —C(=O)—R$^4$, —NH—C(=O)—R$^4$, —NO$_2$ and —C(=O)—NR$^6$R$^7$, and the heteroaryl may be unsubstituted, or one or more H atoms of the heteroaryl may be substituted with a substituent selected from the group consisting of a halogen atom, —CN, —C$_1$-C$_3$ alkyl, —C$_1$-C$_3$ alkoxy, —CH$_2$—OR$^4$, —C(=O)—OR$^4$, —S(=O)$_2$—R$^4$ and —C(=O)—NR$^6$R$^7$;
R$^4$ may be C$_1$-C$_3$ alkyl;
R$^6$ may be H; and
R$^7$ may be C$_1$-C$_3$ alkyl or C$_3$-C$_2$ cycloalkyl.

In another embodiment of the present invention,
L may be —CH$_2$— or —C(=O)—;
R$^1$ may be H or a halogen atom;
R$^2$ and R$^3$ may be each independently H or C$_1$-C$_3$ alkyl, or R$^2$ and R$^3$ may be linked to each other to form a ring;
ring A may be aryl or a heteroaryl containing 1 to 3 heteroatoms, wherein one or more H atoms of the aryl may be substituted with a substituent selected from the group consisting of a halogen atom, —CN, —C$_1$-C$_3$ alkyl, —C$_1$-C$_3$ alkoxy, —C(=O)—R$^4$, —NO$_2$ and —C(=O)—NR$^6$R$^7$, and the heteroaryl may be unsubstituted, or one or more H atoms of the heteroaryl may be substituted with a substituent selected from the group consisting of a halogen atom, —CN, —C$_1$-C$_3$ alkyl, —C$_1$-C$_3$ alkoxy, —C(=O)—OR$^4$, —S(=O)$_2$—R$^4$ and —C(=O)—NR$^6$R$^7$;
R$^4$ may be C$_1$-C$_3$ alkyl;
R$^6$ may be H; and
R$^7$ may be C$_1$-C$_3$ alkyl or C$_3$-C$_7$ cycloalkyl.

In one embodiment of the present invention, R$^2$ and R$^3$ may be each independently H or C$_1$-C$_3$ alkyl. In this case, ring A is preferably substituted with at least one substituent.

In another embodiment of the present invention, R$^2$ and R$^3$ may be linked to each other to form a ring.

In the present invention, the aryl may be a benzene ring, and the heteroaryl may be a monocyclic ring or a bicyclic ring. The monocyclic ring is preferably a ring selected from pyridine, pyrazine, pyrimidine, pyridazine, thiophene, thiazole, thiadiazole, oxazole and oxadiazole, and the bicyclic ring is preferably a ring selected from the group consisting of indole, indazole, cyclopentapyridine, dihydrocyclopentapyridine, furopyridine, dihydrofuropyridine, oxazolopyridine, benzoxazole, and benzoisoxazole.

Among the tricyclic derivative compounds of formula 1 according to the present invention, preferred compounds are as follows:
1) 8-{[4-(4-methoxyphenyl)piperazin-1-yl]methyl}-1,2,3,4-tetrahydrobenzo[h][1,6]naphthyridin-5(6H)-one;
2) 8-{[4-(4-fluorophenyl)piperazin-1-yl]methyl}-10-methoxy-1,2,3,4-tetrahydrobenzo[h][1,6]naphthyridin-5(6H)-one;
3) 10-ethoxy-8-{[4-(4-fluorphenyl)piperazin-1-yl]methyl}-1,2,3,4-tetrahydrobenzo[h][1,6]naphthyridin-5(6H)-one;
4) 10-ethoxy-8-{[4-(pyrimidin-2-yl)piperazin-1-yl]methyl}-1,2,3,4-tetrahydrobenzo[h][1,6]naphthyridin-5(6H)-one;
5) 10-ethoxy-8-{[4-(pyridin-2-yl)piperazin-1-yl]methyl}-1,2,3,4-tetrahydrobenzo[h][1,6]naphthyridin-5(6H)-one;
6) 10-ethoxy-8-{[4-(5-fluoropyrimidin-2-yl)piperazin-1-yl]methyl}-1,2,3,4-tetrahydrobenzo[h][1,6]naphthyridin-5(6H)-one;
7) 10-ethoxy-8-{[4-(5-fluoropyridin-2-yl)piperazin-1-yl]methyl}-1,2,3,4-tetrahydrobenzo[h][1,6]naphthyridin-5(6H)-one;
8) 10-ethoxy-8-{[4-(6-fluoropyridin-2-yl)piperazin-1-yl]methyl}-1,2,3,4-tetrahydrobenzo[h][1,6]naphthyridin-5(6H)-one;
9) 10-ethoxy-8-{[4-(3-fluoropyridin-2-yl)piperazin-1-yl]methyl}-1,2,3,4-tetrahydrobenzo[h][1,6]naphthyridin-5(6H)-one;
10) 8-{[4-(5-chloro-3-fluoropyridin-2-yl)piperazin-1-yl]methyl}-10-ethoxy-1,2,3,4-tetrahydrobenzo[h][1,6]naphthyridin-5(6H)-one;
11) 10-ethoxy-8-{[4-(6-(trifluoromethyl)pyridin-2-yl)piperazin-1-yl]methyl}-1,2,3,4-tetrahydrobenzo[h][1,6]naphthyridin-5(6H)-one;
12) 8-({4-[3-chloro-5-(trifluoromethyl)pyridin-2-yl]piperazin-1-yl}methyl)-10-ethoxy-1,2,3,4-tretrahydrobenzo[h][1,6]naphthyridin-5(6H)-one;
13) 8-{[4-(5-chloropyridin-2-yl)piperazin-1-yl]methyl}-10-ethoxy-1,2,3,4-tetrahydrobenzo[h][1,6]naphthyridin-5(6H)-one;
14) 8-{[4-(6-chloropyridin-2-yl)piperazin-1-yl]methyl}-10-ethoxy-1,2,3,4-tetrahydrobenzo[h][1,6]naphthyridin-5(6H)-one;
15) 8-{[4-(3-chloropyridin-2-yl)piperazin-1-yl]methyl}-10-ethoxy-1,2,3,4-tetrahydrobenzo[h][1,6]naphthyridin-5(6H)-one;
16) 8-{[4-(5-bromopyridin-2-yl)piperazin-1-yl]methyl}-10-ethoxy-1,2,3,4-tetrahydrobenzo[h][1,6]naphthyridin-5

17) 10-ethoxy-8-{[4-(3-methylpyridin-2-yl)piperazin-1-yl]methyl}-1,2,3,4-tetrahydrobenzo[h][1,6]naphthyridin-5(6H)-one;
18) 6-{4-{(10-ethoxy-5-oxo-1,2,3,4,5,6-hexahydrobenzo[h][1,6]naphthyridin-8-yl)methyl]piperzin-1-yl}-N-methyl-nicotinamide;
19) 6-{4-{(10-ethoxy-5-oxo-1,2,3,4,5,6-hexahydrobenzo[h][1,6]naphthyridin-8-yl)methyl]piperazin-1-yl}-N-ethyl-nicotinamide;
20) N-cyclopropyl-6-{4-[(10-ethoxy-5-oxo-1,2,3,4,5,6-hexahydrobenzo[h][1,6]naphthyridin-8-yl)methyl]piperazin-1-yl}nicotinamide;
21) 8-{[4-(4-chlorophenyl)piperazin-1-yl]methyl}-10-ethoxy-1,2,3,4-tetrahydrobenzo[h][1,6]naphthyridin-5(6H)-one;
22) 8-{[4-(4-bromophenyl)piperazin-1-yl]methyl}-10-ethoxy-1,2,3,4-tetrahydrobenzo[h][1,6]naphthyridin-5(6H)-one;
23) 4-{4-[(10-ethoxy-5-oxo-1,2,3,4,5,6-hexahydrobenzo[h][1,6]naphthyridin-8-yl)methyl]piperazin-1-yl}benzonitrile;
24) 3-fluoro-4-{4-[(10-ethoxy-5-oxo-1,2,3,4,5,6-hexahydrobenzo[h][1,6]naphthyridin-8-yl)methyl]piperazin-1-yl}benzonitrile;
25) 3-chloro-4-{4-[(10-ethoxy-5-oxo-1,2,3,4,5,6-hexahydrobenzo[h][1,6]naphthyridin-8-yl)methyl]piperazin-1-yl}benzonitrile;
26) 4-{4-[(10-ethoxy-5-oxo-1,2,3,4,5,6-hexahydrobenzo[h][1,6]naphthyridin-8-yl)methyl]piperazin-1-yl}-3-methylbenzonitrile;
27) 10-ethoxy-8-{[4-(4-fluoro-2-methylphenyl)piperazin-1-yl]methyl}-1,2,3,4-tetrahydrobenzo[h][1,6]naphthyridin-5(6H)-one;
28) 4-{4-[(10-ethoxy-5-oxo-1,2,3,4,5,6-hexahydrobenzo[h][1,6]naphthyridin-8-yl)methyl]piperazin-1-yl}-3,5-difluorobenzonitrile;
29) 4-{4-[(10-ethoxy-5-oxo-1,2,3,4,5,6-hexahydrobenzo[h][1,6]naphthyridin-8-yl)methyl]piperazin-1-yl}-2-fluorobenzonitrile;
30) 4-{4-[(10-ethoxy-5-oxo-1,2,3,4,5,6-hexahydrobenzo[h][1,6]naphthyridin-8-yl)methyl]piperazin-1-yl}-N-ethylbenzamide;
31) 4-{4-[(10-ethoxy-5-oxo-1,2,3,4,5,6-hexahydrobenzo[h][1,6]naphthyridin-8-yl)methyl]piperazin-1-yl}-2-fluoro-N-methylbenzamide;
32) 4-{4-[(10-ethoxy-5-oxo-1,2,3,4,5,6-hexahydrobenzo[h][1,6]naphthyridin-8-yl)methyl]piperazin-1-yl}-N-ethyl-2-fluorobenzamide;
33) 3-chloro-4-{4-[(10-ethoxy-5-oxo-1,2,3,4,5,6-hexahydrobenzo[h][1,6]naphthyridin-8-yl)methyl]piperazin-1-yl}-N-ethylbenzamide;
34) 3-chloro-N-cyclopropyl-4-{4-[(10-ethoxy-5-oxo-1,2,3,4,5,6-hexahydrobenzo[h][1,6]naphthyridin-8-yl)methyl]piperazin-1-yl}benzamide;
35) 3-chloro-4-{4-[(10-ethoxy-5-oxo-1,2,3,4,5,6-hexahydrobenzo[h][1,6]naphthyridin-8-yl)methyl]piperazin-1-yl}-N-methylbenzamide;
36) 4-{4-[(10-ethoxy-5-oxo-1,2,3,4,5,6-hexahydrobenzo[h][1,6]naphthyridin-8-yl)methyl]piperazin-1-yl}-N,3-dimethylbenzamide;
37) 4-{4-[(10-ethoxy-5-oxo-1,2,3,4,5,6-hexahydrobenzo[h][1,6]naphthyridin-8-yl)methyl]piperazin-1-yl}-N-ethyl-3-methylbenzamide;
38) N-cyclopropyl-4-{4-[(10-ethoxy-5-oxo-1,2,3,4,5,6-hexahydrobenzo[h][1,6]naphthyridin-8-yl)methyl]piperazin-1-yl}-3-methylbenzamide;
39) 10-methoxy-8-{[4-(pyridin-2-yl)piperazin-1-yl]methyl}-1,2,3,4-tetrahydrobenzo[h][1,6]naphthyridin-5(6H)-one;
40) 10-methoxy-8-{[4-(3-methylpyridin-2-yl)piperazin-1-yl]methyl}-1,2,3,4-tetrahydrobenzo[h][1,6]naphthyridin-5(6H)-one;
41) 8-{[4-(5-fluoropyridin-2-yl)piperazin-1-yl]methyl}-10-methoxy-1,2,3,4-tetrahydrobenzo[h][1,6]naphthyridin-5(6H)-one;
42) 4-{4-[(10-methoxy-5-oxo-1,2,3,4,5,6-hexahydrobenzo[h][1,6]naphthyridin-8-yl)methyl]piperazin-1-yl}benzonitrile;
43) 8-{[4-(4-fluoro-2-methylphenyl)piperazin-1-yl]methyl}-10-methoxy-1,2,3,4-tetrahydrobenzo[h][1,6]naphthyridin-5(6H)-one;
44) 4-{4-[(10-methoxy-5-oxo-1,2,3,4,5,6-hexahydrobenzo[h][1,6]naphthyridin-8-yl)methyl]piperazin-1-yl}-3-methylbenzonitrile;
45) 3-fluoro-4-{4-[(10-methoxy-5-oxo-1,2,3,4,5,6-hexahydrobenzo[h][1,6]naphthyridin-8-yl)methyl]piperazin-1-yl}benzonitrile;
46) 3,5-difluoro-4-{4-[(10-methoxy-5-oxo-1,2,3,4,5,6-hexahydrobenzo[h][1,6]naphthyridin-8-yl)methyl]piperazin-1-yl}benzonitrile;
47) 2-fluoro-4-{4-[(10-methoxy-5-oxo-1,2,3,4,5,6-hexahydrobenzo[h][1,6]naphthyridin-8-yl)methyl]piperazin-1-yl}benzonitrile;
48) 8-{[4-(4-fluorophenyl)piperazin-1-yl]methyl}-1,2,3,4-tetrahydrobenzo[h][1,6]naphthyridin-5(6H)-one;
49) 8-{[4-(4-fluoro-2-methylphenyl)piperazin-1-yl]methyl}-1,2,3,4-tetrahydrobenzo[h][1,6]naphthyridin-5(6H)-one;
50) 3-fluoro-4-{4-[(5-oxo-1,2,3,4,5,6-hexahydrobenzo[h][1,6]naphthyridin-8-yl)methyl]piperazin-1-yl}benzonitrile;
51) 3-chloro-4-{4-[(5-oxo-1,2,3,4,5,6-hexahydrobenzo[h][1,6]naphthyridin-8-yl)methyl]piperazin-1-yl}benzonitrile;
52) 3-bromo-4-{4-[(5-oxo-1,2,3,4,5,6-hexahydrobenzo[h][1,6]naphthyridin-8-yl)methyl]piperazin-1-yl}benzonitrile;
53) 3-methyl-4-{4-[(5-oxo-1,2,3,4,5,6-hexahydrobenzo[h][1,6]naphthyridin-8-yl)methyl]piperazin-1-yl}benzonitrile;
54) 3-methoxy-4-{4-[(5-oxo-1,2,3,4,5,6-hexahydrobenzo[h][1,6]naphthyridin-8-yl)methyl]piperazin-1-yl}benzonitrile;
55) 8-({4-[4-(diethylamino)-2-fluorophenyl]piperazin-1-yl}methyl)-1,2,3,4-tetrahydrobenzo[h][1,6]naphthyridin-5-(6H)-one;
56) 3-acetyl-4-{4-[(5-oxo-1,2,3,4,5,6-hexahydrobenzo[h][1,6]naphthyridin-8-yl)methyl]piperazin-1-yl}benzonitrile;
57) 4-fluoro-2-{4-[(5-oxo-1,2,3,4,5,6-hexahydrobenzo[h][1,6]naphthyridin-8-yl)methyl]piperazin-1-yl}benzonitrile;
58) 3,5-difluoro-4-{4-[(5-oxo-1,2,3,4,5,6-hexahydrobenzo[h][1,6]naphthyridin-8-yl)methyl]piperazin-1-yl}benzonitrile;
59) 8-{[4-(2-fluoro-4-nitrophenyl)piperazin-1-yl]methyl}-1,2,3,4-tetrahydrobenzo[h][1,6]naphthyridin-5(6H)-one;
60) 2-fluoro-4-{4-[(5-oxo-1,2,3,4,5,6-hexahydrobenzo[h][1,6]naphthyridin-8-yl)methyl]piperazin-1-yl}benzonitrile;
61) 2-chloro-4-{4-[(5-oxo-1,2,3,4,5,6-hexahydrobenzo[h][1,6]naphthyridin-8-yl)methyl]piperazin-1-yl}benzonitrile;

62) 4-{4-[(5-oxo-1,2,3,4,5,6-hexahydrobenzo[h][1,6]naphthyridin-8-yl)methyl]piperazin-1-yl}-2-(trifluoromethyl)benzonitrile;
63) 2-methyl-4-{4-[(5-oxo-1,2,3,4,5,6-hexahydrobenzo[h][1,6]naphthyridin-8-yl)methyl]piperazin-1-yl}benzonitrile;
64) N-ethyl-3-methyl-4-{4-[(5-oxo-1,2,3,4,5,6-hexahydrobenzo[h][1,6]naphthyridin-8-yl)methyl]piperazin-1-yl}benzamide;
65) N-cyclopropyl-3-methyl-4-{4-[(5-oxo-1,2,3,4,5,6-hexahydrobenzo[h][1,6]naphthyridin-8-yl)methyl]piperazin-1-yl}benzamide;
66) 3-fluoro-N-methyl-4-{4-[(5-oxo-1,2,3,4,5,6-hexahydrobenzo[h][1,6]naphthyridin-8-yl)methyl]piperazin-1-yl}benzamide;
67) N-ethyl-3-fluoro-4-{4-[(5-oxo-1,2,3,4,5,6-hexahydrobenzo[h][1,6]naphthyridin-8-yl)methyl]piperazin-1-yl}benzamide;
68) N-(3-fluoro-4-{4-[(5-oxo-1,2,3,4,5,6-hexahydrobenzo[h][1,6]naphthyridin-8-yl)methyl]piperazin-1-yl}phenyl)propionamide;
69) N-cyclopropyl-3-fluoro-4-{4-[(5-oxo-1,2,3,4,5,6-hexahydrobenzo[h][1,6]naphthyridin-8-yl)methyl]piperazin-1-yl}benzamide;
70) 3-chloro-N-methyl-4-{4-[(5-oxo-1,2,3,4,5,6-hexahydrobenzo[h][1,6]naphthyridin-8-yl)methyl]piperazin-1-yl}benzamide;
71) 3-chloro-N-ethyl-4-{4-[(5-oxo-1,2,3,4,5,6-hexahydrobenzo[h][1,6]naphthyridin-8-yl)methyl]piperazin-1-yl}benzamide;
72) 3-chloro-N-cyclopropyl-4-{4-[(5-oxo-1,2,3,4,5,6-hexahydrobenzo[h][1,6]naphthyridin-8-yl)methyl]piperazin-1-yl}benzamide;
73) 3-bromo-N-methyl-4-{4-[(5-oxo-1,2,3,4,5,6-hexahydrobenzo[h][1,6]naphthyridin-8-yl)methyl]piperazin-1-yl}benzamide;
74) 3-bromo-N-ethyl-4-{4-[(5-oxo-1,2,3,4,5,6-hexahydrobenzo[h][1,6]naphthyridin-8-yl)methyl]piperazin-1-yl}benzamide;
75) 3-bromo-N-cyclopropyl-4-{4-[(5-oxo-1,2,3,4,5,6-hexahydrobenzo[h][1,6]naphthyridin-8-yl)methyl]piperazin-1-yl}benzamide;
76) 2-fluoro-N-methyl-4-{4-[(5-oxo-1,2,3,4,5,6-hexahydrobenzo[h][1,6]naphthyridin-8-yl)methyl]piperazin-1-yl}benzamide;
77) N-ethyl-2-fluoro-4-{4-[(5-oxo-1,2,3,4,5,6-hexahydrobenzo[h][1,6]naphthyridin-8-yl)methyl]piperazin-1-yl}benzamide;
78) N-cyclopropyl-2-fluoro-4-{4-[(5-oxo-1,2,3,4,5,6-hexahydrobenzo[h][1,6]naphthyridin-8-yl)methyl]piperazin-1-yl}benzamide;
79) N-ethyl-2-fluoro-N-methyl-4-{4-[(5-oxo-1,2,3,4,5,6-hexahydrobenzo[h][1,6]naphthyridin-8-yl)methyl]piperazin-1-yl}benzamide;
80) 2-chloro-N-methyl-4-{4-[(5-oxo-1,2,3,4,5,6-hexahydrobenzo[h][1,6]naphthyridin-8-yl)methyl]piperazin-1-yl}benzamide;
81) 2-chloro-N-ethyl-4-{4-[(5-oxo-1,2,3,4,5,6-hexahydrobenzo[h][1,6]naphthyridin-8-yl)methyl]piperazin-1-yl}benzamide;
82) 2-chloro-N-cyclopropyl-4-{4-[(5-oxo-1,2,3,4,5,6-hexahydrobenzo[h][1,6]naphthyridin-8-yl)methyl]piperazin-1-yl}benzamide;
83) ethyl 2-chloro-5-{4-[(5-oxo-1,2,3,4,5,6-hexahydrobenzo[h][1,6]naphthyridin-8-yl)methyl]piperazin-1-yl}benzoate;
84) N-ethyl-3,5-difluoro-4-{4-[(5-oxo-1,2,3,4,5,6-hexahydrobenzo[h][1,6]naphthyridin-8-yl)methyl]piperazin-1-yl}benzamide;
85) N-cyclopropyl-3,5-difluoro-4-{4-[(5-oxo-1,2,3,4,5,6-hexahydrobenzo[h][1,6]naphthyridin-8-yl)methyl]piperazin-1-yl}benzamide;
86) 8-{[4-(pyridin-2-yl)piperazin-1-yl]methyl}-1,2,3,4-tetrahydrobenzo[h][1,6]naphthyridin-5(6H)-one;
87) 8-({4-[4-(trifluoromethyl)pyridin-2-yl]piperazin-1-yl}methyl)-1,2,3,4-tetrahydrobenzo[h][1,6]naphthyridin-5(6H)-one;
88) 8-({4-[3-(trifluoromethyl)pyridin-2-yl]piperazin-1-yl}methyl)-1,2,3,4-tetrahydrobenzo[h][1,6]naphthyridin-5(6H)-one;
89) 6-{4-[(5-oxo-1,2,3,4,5,6-hexahydrobenzo[h][1,6]naphthyridin-8-yl)methyl]piperazin-1-yl}nicotinonitrile;
90) 8-{[4-(3-methylpyridin-2-yl)piperazin-1-yl]methyl}-1,2,3,4-tetrahydrobenzo[h][1,6]naphthyridin-5(6H)-one;
91) 8-{[4-(5-fluoro-3-methylpyridin-2-yl)piperazin-1-yl]methyl}-1,2,3,4-tetrahydrobenzo[h][1,6]naphthyridin-5(6H)-one;
92) 8-{[4-(pyrazin-2-yl)piperazin-1-yl]methyl}-1,2,3,4-tetrahydrobenzo[h][1,6]naphthyridin-5(6H)-one;
93) 8-{[4-(6-chloropyridazin-3-yl)piperazin-1-yl]methyl}-1,2,3,4-tetrahydrobenzo[h][1,6]naphthyridin-5(6H)-one;
94) 8-{[4-(3,5-dichloropyridin-2-yl)piperazin-1-yl]methyl}-1,2,3,4-tetrahydrobenzo[h][1,6]naphthyridin-5(6H)-one;
95) N-methyl-6-{4-[(5-oxo-1,2,3,4,5,6-hexahydrobenzo[h][1,6]naphthyridin-8-yl)methyl]piperazin-1-yl}nicotinamide;
96) N-ethyl-6-{4-[(5-oxo-1,2,3,4,5,6-hexahydrobenzo[h][1,6]naphthyridin-8-yl)methyl]piperazin-1-yl}nicotinamide;
97) N-cyclopropyl-6-{4-[(5-oxo-1,2,3,4,5,6-hexahydrobenzo[h][1,6]naphthyridin-8-yl)methyl]piperazin-1-yl}nicotinamide;
98) 8-{[4-(thiazol-2-yl)piperazin-1-yl]methyl}-1,2,3,4-tetrahydrobenzo[h][1,6]naphthyridin-5(6H)-one;
99) ethyl 2-{4-[(5-oxo-1,2,3,4,5,6-hexahydrobenzo[h][1,6]naphthyridin-8-yl)methyl]piperazin-1-yl}thiazole-4-carboxylate;
100) N-ethyl 2-{4-[(5-oxo-1,2,3,4,5,6-hexahydrobenzo[h][1,6]naphthyridin-8-yl)methyl]piperazin-1-yl}thiazole-4-carboxamide;
101) 2-fluoro-4-{8-[(5-oxo-1,2,3,4,5,6-hexahydrobenzo[h][1,6]naphthyridin-8-yl)methyl]-3,8-diazabicyclo[3,2,1]octan-3-yl}benzonitrile;
102) 6-{8-[(5-oxo-1,2,3,4,5,6-hexahydrobenzo[h][1,6]naphthyridin-8-yl)methyl]-3,8-diazabicyclo[3,2,1]octan-3-yl}nicotinonitrile;
103) 2-fluoro-4-{(1S,4S)-5-[(5-oxo-1,2,3,4,5,6-hexahydrobenzo[h][1,6]naphthyridin-8-yl)methyl]-2,5-diazabicyclo[2.2.1]heptan-2-yl}benzonitrile;
104) 6-{(1S,4S)-5-[(oxo-1,2,3,4,5,6-hexahydrobenzo[h][1,6]naphthyridin-8-yl)methyl]-2,5-diazabicyclo[2.2.1]heptan-2-yl}nicotinonitrile;
105) 10-ethoxy-8-{[4-(5-fluoropyrimidin-2-yl)-2-methyl-piperazin-1-yl]methyl}-1,2,3,4-tetrahydrobenzo[h][1,6]naphthyridin-5(6H)-one;
106) 10-ethoxy-8-{[4-(5-fluoropyridin-2-yl)-2-methylpiperazin-1-yl]methyl}-1,2,3,4-tetrahydrobenzo[h][1,6]naphthyridin-5(6H)-one;
107) 3-fluoro-4-{3-methyl-4-[(5-oxo-1,2,3,4,5,6-hexahydrobenzo[h][1,6]naphthyridin-8-yl)methyl]piperazin-1-yl}benzonitrile;

108) (R)-3-fluoro-4-{3-methyl-4-[(5-oxo-1,2,3,4,5,6-hexahydrobenzo[h][1,6]naphthyridin-8-yl)methyl]piperazin-1-yl}benzonitrile;
109) (S)-3-fluoro-4-{3-methyl-4-[(5-oxo-1,2,3,4,5,6-hexahydrobenzo[h][1,6]naphthyridin-8-yl)methyl]piperazin-1-yl}benzonitrile;
110) (R)-3-fluoro-4-{2-methyl-4-[(5-oxo-1,2,3,4,5,6-hexahydrobenzo[h][1,6]naphthyridin-8-yl)methyl]piperazin-1-yl}benzonitrile;
111) 2-fluoro-4-{3-methyl-4-[(5-oxo-1,2,3,4,5,6-hexahydrobenzo[h][1,6]naphthyridin-8-yl)methyl]piperazin-1-yl}benzonitrile;
112) (R)-2-fluoro-4-{3-methyl-4-[(5-oxo-1,2,3,4,5,6-hexahydrobenzo[h][1,6]naphthyridin-8-yl)methyl]piperazin-1-yl}benzonitrile;
113) (S)-2-fluoro-4-{3-methyl-4-[(5-oxo-1,2,3,4,5,6-hexahydrobenzo[h][1,6]naphthyridin-8-yl)methyl]piperazin-1-yl}benzonitrile;
114) (R)-2-fluoro-4-{2-methyl-4-[(5-oxo-1,2,3,4,5,6-hexahydrobenzo[h][1,6]naphthyridin-8-yl)methyl]piperazin-1-yl}benzonitrile;
115) 8-({4-[4-(trifluoromethyl)phenyl]piperazin-1-yl}methyl)-1,2,3,4-tetrahydrobenzo[h][1,2]naphthyridin-5(6H)-one;
116) 6-{4-[(10-ethoxy-5-oxo-1,2,3,4,5,6-hexahydrobenzo[h][1,6]naphthyridin-8-yl)methyl]piperazin-1-yl}nicotinonitrile;
117) 8-({4-[2-chloro-4-(trifluoromethyl)phenyl]piperazin-1-yl}methyl)-1,2,3,4-tetrahydrobenzo[h][1,6]naphthyridin-5(6H)-one;
118) 8-({4-[3-chloro-4-(trifluoromethyl)phenyl]piperazin-1-yl}methyl)-1,2,3,4-tetrahydrobenzo[h][1,6]naphthyridin-5(6H)-one;
119) 8-{[4-(3-fluoro-4-nitrophenyl)piperazin-1-yl]methyl}-1,2,3,4-tetrahydrobenzo[h][1,6]naphthyridin-5(6H)-one;
120) 8-{[4-(5-chloropyridin-2-yl)piperazin-1-yl]methyl}-1,2,3,4-tetrahydrobenzo[h][1,6]naphthyridin-5(6H)-one;
121) 8-({4-[5-(trifluoromethyl)pyridin-2-yl]piperazin-1-yl}methyl)-1,2,3,4-tetrahydrobenzo[h][1,6]naphthyridin-5(6H)-one;
122) 8-({4-[5-(methylsulfonyl)pyridin-2-yl]piperazin-1-yl}methyl)-1,2,3,4-tetrahydrobenzo[h][1,6]naphthyridin-5(6H)-one;
123) 5-{4-[(5-oxo-1,2,3,4,5,6-hexahydrobenzo[h][1,6]naphthyridin-8-yl)methyl]piperazin-1-yl}picolinonitrile;
124) 2-{4-[(5-oxo-1,2,3,4,5,6-hexahydrobenzo[h][1,6]naphthyridin-8-yl)methyl]piperazin-1-yl}isonicotinonitrile;
125) 2-{4-[(5-oxo-1,2,3,4,5,6-hexahydrobenzo[h][1,6]naphthyridin-8-yl)methyl]piperazin-1-yl}nicotinonitrile;
126) 6-{4-[(5-oxo-1,2,3,4,5,6-hexahydrobenzo[h][1,6]naphthyridin-8-yl)methyl]piperazin-1-yl}picolinonitrile;
127) 8-{[4-(4-methoxypyridin-2-yl)piperazin-1-yl]methyl}-1,2,3,4-tetrahydrobenzo[h][1,6]naphthyridin-5(6H)-one;
128) 8-({4-[5-(methoxymethyl)-pyridin-2-yl]piperazin-1-yl}methyl)-1,2,3,4-tetrahydrobenzo[h][1,6]naphthyridin-5(6H)-one;
129) 5-{4-[(5-oxo-1,2,3,4,5,6-hexahydrobenzo[h][1,6]naphthyridin-8-yl)methyl]piperazin-1-yl}pyrazine-2-carbonitrile;
130) 8-{[4-(6-methylpyridazin-3-yl)piperazin-1-yl]methyl}-1,2,3,4-tetrahydrobenzo[h][1,6]naphthyridin-5(6H)-one;
131) 8-{[4-(6-methoxypyridazin-3-yl)piperazin-1-yl]methyl}-1,2,3,4-tetrahydrobenzo[h][1,6]naphthyridin-5(6H)-one;
132) 6-{4-[(5-oxo-1,2,3,4,5,6-hexahydrobenzo[h][1,6]naphthyridin-8-yl)methyl]piperazin-1-yl}pyridazine-3-carbonitrile;
133) 5-chloro-6-{4-[(5-oxo-1,2,3,4,5,6-hexahydrobenzo[h][1,6]naphthyridin-8-yl)methyl]piperazin-1-yl}nicotinonitrile;
134) 6-chloro-4-{4-[(5-oxo-1,2,3,4,5,6-hexahydrobenzo[h][1,6]naphthyridin-8-yl)methyl]piperazin-1-yl}nicotinonitrile;
135) 4-chloro-6-{4-[(5-oxo-1,2,3,4,5,6-hexahydrobenzo[h][1,6]naphthyridin-8-yl)methyl]piperazin-1-yl}nicotinonitrile;
136) 5-chloro-2-{4-[(5-oxo-1,2,3,4,5,6-hexahydrobenzo[h][1,6]naphthyridin-8-yl)methyl]piperazin-1-yl}isonicotinonitrile;
137) 4-methoxy-6-{4-[(5-oxo-1,2,3,4,5,6-hexahydrobenzo[h][1,6]naphthyridin-8-yl)methyl]piperazin-1-yl}nicotinonitrile;
138) 8-{[4-(5-bromo-4-methoxypyridin-2-yl)piperazin-1-yl]methyl}-1,2,3,4-tetrahydrobenzo[h][1,6]naphthyridin-5(6H)-one;
139) 2-{4-[(5-oxo-1,2,3,4,5,6-hexahydrobenzo[h][1,6]naphthyridin-8-yl)methyl]piperazin-1-yl}thiazole-4-carbonitrile;
140) 5-{4-[(5-oxo-1,2,3,4,5,6-hexahydrobenzo[h][1,6]naphthyridin-8-yl)methyl]piperazin-1-yl}thiophene-2-carbonitrile;
141) ethyl 2-{4-[((5-oxo-1,2,3,4,5,6-hexahydrobenzo[h][1,6]naphthyridin-8-yl)methyl]piperazin-1-yl}thiazole-5-carboxylate;
142) 2-{4-[(5-oxo-1,2,3,4,5,6-hexahydrobenzo[h][1,6]naphthyridin-8-yl)methyl]piperazin-1-yl}thiazole-5-carbonitrile;
143) 5-{4-[(5-oxo-1,2,3,4,5,6-hexahydrobenzo[h][1,6]naphthyridin-8-yl)methyl]piperazin-1-yl}-1,3,4-thiadiazole-2-carbonitrile;
144) 2-{4-[(5-oxo-1,2,3,4,5,6-hexahydrobenzo[h][1,6]naphthyridin-8-yl)methyl]piperazin-1-yl}oxazole-4-carbonitrile;
145) 5-{4-[(5-oxo-1,2,3,4,5,6-hexahydrobenzo[h][1,6]naphthyridin-8-yl)methyl]piperazin-1-yl}-1,2,4-thiadiazole-3-carbonitrile;
146) 5-{4-[(5-oxo-1,2,3,4,5,6-hexahydrobenzo[h][1,6]naphthyridin-8-yl)methyl]piperazin-1-yl}-1,3,4-oxadiazole-2-carbonitrile;
147) 8-{[4-(5-chlorobenzo[d]oxazol-2-yl)piperazin-1-yl]methyl}-1,2,3,4-tetrahydrobenzo[h][1,6]naphthyridin-5(6H)-one;
148) 8-{[4-(2-methylbenzo[d]oxazol-6-yl)piperazin-1-yl]methyl}-1,2,3,4-tetrahydrobenzo[h][1,6]naphthyridin-5(6H)-one;
149) 8-{[4-(3-methylbenzo[d]isoxazol-5-yl)piperazin-1-yl]methyl}-1,2,3,4-tetrahydrobenzo[h][1,6]naphthyridin-5(6H)-one;
150) 8-{[4-(1H-indol-6-yl)piperazin-1-yl]methyl}-1,2,3,4-tetrahydrobenzo[h][1,6]naphthyridin-5(6H)-one;
151) 8-{[4-(1H-indazol-5-yl)piperazin-1-yl]methyl}-1,2,3,4-tetrahydrobenzo[h][1,6]naphthyridin-5(6H)-one;
152) 8-{[4-(1H-indazol-6-yl)piperazin-1-yl]methyl}-1,2,3,4-tetrahydrobenzo[h][1,6]naphthyridin-5(6H)-one;
153) 8-{[4-(benzo[d]isoxazol-5-yl)piperazin-1-yl]methyl}-1,2,3,4-tetrahydrobenzo[h][1,6]naphthyridin-5(6H)-one;
154) 8-{[4-(oxazolo[4,5-b]pyridin-2-yl)piperazin-1-yl]methyl}-1,2,3,4-tetrahydrobenzo[h][1,6]naphthyridin-5(6H)-one;

155) 8-{[4-(oxazolo[5,4-b]pyridin-2-yl)piperazin-1-yl]methyl}-1,2,3,4-tetrahydrobenzo[h][1,6]naphthyridin-5(6H)-one;
156) 8-{[4-(2,3-dihydrofuro[2,3-b]pyridin-6-yl)piperazin-1-yl]methyl}-1,2,3,4-tetrahydrobenzo[h][1,6]naphthyridin-5(6H)-one;
157) 1-{4-[(5-oxo-1,2,3,4,5,6-hexahydrobenzo[h][1,6]naphthyridin-8-yl)methyl]piperazin-1-yl}-6,7-dihydro-5H-cyclopenta[c]pyridine-4-carbonitrile;
158) 8-{[3-(pyrazin-2-yl)-3,8-diazabicyclo[3.2.1]octan-8-yl]methyl}-1,2,3,4-tetrahydrobenzo[h][1,6]naphthyridin-5(6H)-one;
159) 6-{3-[(5-oxo-1,2,3,4,5,6-hexahydrobenzo[h][1,6]naphthyridin-8-yl)methyl]-3,8-diazabicyclo[3.2.1]octan-8-yl}nicotinonitrile;
160) 8-{[3-(6-chloropyridazin-3-yl)-3,8-diazabicyclo[3.2.1]octan-8-yl]methyl}-1,2,3,4-tetrahydrobenzo[h][1,6]naphthyridin-5(6H)-one;
161) 3-fluoro-4-{(1S,4S)-5-[(5-oxo-1,2,3,4,5,6-hexahydrobenzo[h][1,6]naphthyridin-8-yl)methyl]-2,5-diazabicyclo[2.2.1]heptan-2-yl}benzonitrile;
162) 8-{[(1S,4S)-5-(2-fluoro-4-nitrophenyl)-2,5-diazabicyclo[2.2.1]heptan-2-yl]methyl}-1,2,3,4-tetrahydrobenzo[h][1,6]naphthyridin-5(6H)-one;
163) 8-{[(1S,4S)-5-(6-chloropyridazin-3-yl)-2,5-diazabicyclo[2.2.1]heptan-2-yl]methyl}-10-fluoro-1,2,3,4-tetrahydrobenzo[h][1,6]naphthyridin-5(6H)-one;
164) 10-fluoro-8-{[(1S,4S)-5-(pyridazin-2-yl)-2,5-diazabicyclo[2.2.1]heptan-2-yl]methyl}-1,2,3,4-tetrahydrobenzo[h][1,6]naphthyridin-5(6H)-one;
165) (S)-2-fluoro-4-{2-methyl-4-[(5-oxo-1,2,3,4,5,6-hexahydrobenzo[h][1,6]naphthyridin-8-yl)methyl]piperazin-1-yl}benzonitrile;
166) 10-fluoro-8-{[4-(2-fluoro-4-nitrophenyl)piperazin-1-yl]methyl}-1,2,3,4-tetrahydrobenzo[h][1,6]naphthyridin-5(6H)-one;
167) 10-fluoro-8-{[4-(pyridin-2-yl)piperazin-1-yl]methyl}-1,2,3,4-tetrahydrobenzo[h][1,6]naphthyridin-5(6H)-one;
168) 10-fluoro-8-{[4-(3-methylpyridin-2-yl)piperazin-1-yl]methyl}-1,2,3,4-tetrahydrobenzo[h][1,6]naphthyridin-5(6H)-one;
169) 10-fluoro-8-{[4-(5-fluoropyridin-2-yl)piperazin-1-yl]methyl}-1,2,3,4-tetrahydrobenzo[h][1,6]naphthyridin-5(6H)-one;
170) 6-{4-[(10-fluoro-5-oxo-1,2,3,4,5,6-hexahydrobenzo[h][1,6]naphthyridin-8-yl)methyl]piperazin-1-yl) nicotinonitrile;
171) 2-{4-[(10-fluoro-5-oxo-1,2,3,4,5,6-hexahydrobenzo[h][1,6]naphthyridin-8-yl)methyl]piperazin-1-yl)thiazole-5-carbonitrile;
172) 10-fluoro-8-{[4-(4-fluorphenyl)piperazin-1-yl]methyl}-1,2,3,4-tetrahydrobenzo[h][1,6]naphthyridin-5(6H)-one;
173) 2-fluoro-4-{[4-(10-fluoro-5-oxo-1,2,3,4,5,6-hexahydrobenzo[h][1,6]naphthyridin-8-yl)methyl}piperazin-1-yl)benzonitrile;
174) 4-{[4-(10-fluoro-5-oxo-1,2,3,4,5,6-hexahydrobenzo[h][1,6]naphthyridin-8-yl)methyl}piperazin-1-yl)-2-(trifluoromethyl)benzonitrile;
175) 10-fluoro-8-{[4-(4-fluoro-2-methylphenyl)piperazin-1-yl]methyl}-1,2,3,4-tetrahydrobenzo[h][1,6]naphthyridin-5(6H)-one;
176) 3-fluoro-4-{4-[(10-fluoro-5-oxo-1,2,3,4,5,6-hexahydrobenzo[h][1,6]naphthyridin-8-yl)methyl}piperazin-1-yl)benzonitrile;
177) 6-{(1S,4S)-5-[(10-fluoro-5-oxo-1,2,3,4,5,6-hexahydrobenzo[h][1,6]naphthyridin-8-yl)methyl]-2,5-diazabicyclo[2.2.1]heptan-2-yl}nicotinonitrile;
178) 10-fluoro-8-{[4-(pyrazin-2-yl)piperazin-1-yl]methyl}-1,2,3,4-tetrahydrobenzo[h][1,6]naphthyridin-5(6H)-one;
179) 8-{[4-(5-chloropyridin-2-yl)piperazin-1-yl]methyl}-10-fluoro-1,2,3,4-tetrahydrobenzo[h][1,6]naphthyridin-5(6H)-one;
180) 5-{4-[(10-fluoro-5-oxo-1,2,3,4,5,6-hexahydrobenzo[h][1,6]naphthyridin-8-yl)methyl]piperazin-1-yl}picolinonitrile;
181) 8-{[4-(6-chloropyridazin-3-yl)piperazin-1-yl]methyl}-10-fluoro-1,2,3,4-tetrahydrobenzo[h][1,6]naphthyridin-5(6H)-one;
182) 6-{4-[(10-fluoro-5-oxo-1,2,3,4,5,6-hexahydrobenzo[h][1,6]naphthyridin-8-yl)methyl]piperazin-1-yl}pyridazine-3-carbonitrile;
183) 5-{4-[(10-fluoro-5-oxo-1,2,3,4,5,6-hexahydrobenzo[h][1,6]naphthyridin-8-yl)methyl]piperazin-1-yl}thiophene-2-carbonitrile;
184) 6-{8-[(10-fluoro-5-oxo-1,2,3,4,5,6-hexahydrobenzo[h][1,6]naphthyridin-8-yl)methyl]-3,8-diazabicyclo[3,2,1]octan-3-yl}nicotinonitrile;
185) 4-{4-[(10-fluoro-5-oxo-1,2,3,4,5,6-hexahydrobenzo[h][1,6]naphthyridin-8-yl)methyl]piperazin-1-yl}-3-methoxybenzonitrile;
186) 5-[4-(5-oxo-1,2,3,4,5,6-hexahydrobenzo[h][1,6]naphthyridin-8-carbonyl)piperazin-1-yl]thiophene-2-carbonitrile;
187) 6-[4-(5-oxo-1,2,3,4,5,6-hexahydrobenzo[h][1,6]naphthyridin-8-carbonyl)piperazin-1-yl]nicotinonitrile;
188) 2-[4-(5-oxo-1,2,3,4,5,6-hexahydrobenzo[h][1,6]naphthyridin-8-carbonyl)piperazin-1-yl]thiazole-4-carbonitrile; and
189) 2-[4-(5-oxo-1,2,3,4,5,6-hexahydrobenzo[h][1,6]naphthyridin-8-carbonyl)piperazin-1-yl]thiazole-5-carbonitrile.

In the present invention, the pharmaceutically acceptable salt may be preferably an acid addition salt formed by a pharmaceutically acceptable free acid. The acid addition salt may be prepared using a conventional method. For example, the acid addition salt may be prepared by dissolving the compound in an excess of an aqueous acid solution and precipitating the salt using a water-miscible organic solvent such as methanol, ethanol, acetone or acetonitrile. Alternatively, the acid addition salt may be prepared by heating an equimolar amount of the compound and acid or alcohol (e.g., glycol monomethylether) in water, and then drying the mixture by evaporation or filtering the precipitated salt by suction.

Free acids that may be used in the present invention may include organic acids and inorganic acids. Examples of the inorganic acids may include, but are not limited to, hydrochloric acid, phosphoric acid, sulfuric acid, nitric acid and the like, and examples of the organic acids may include, but are not limited to, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like.

In addition, a pharmaceutically acceptable metal salt may be prepared using a base. An alkali metal salt or an alkaline earth metal salt may be obtained, for example, by dissolving the compound in an excess of an alkali metal hydroxide or alkaline earth metal hydroxide solution, filtering the undissolved compound salt and evaporating and drying the filtrate. For use in pharmaceutics, it is particularly preferable to prepare a sodium, potassium or calcium salt, but the scope of the present invention is not limited thereto. In addition, a silver salt corresponding thereto may be obtained by reacting an alkali metal or alkaline earth metal salt with a suitable silver salt (e.g., silver nitrate).

Unless indicated otherwise, pharmaceutically acceptable salts of the compounds of formula 1 include salts of acidic or basic groups which may be present in the compounds of formula 1. For example, pharmaceutically acceptable salts include, but are not limited to, sodium, calcium and potassium salts, etc. of hydroxyl group, and other pharmaceutically acceptable salts of amino group include, but are not limited to, hydrobromide, sulfate salt, hydrogen sulfate salt, phosphate salt, hydrogen phosphate salt, dihydrogen phosphate salt, acetate salt, succinate salt, citrate salt, tartrate salt, lactate salt, mandelate salt, methanesulfonate (mesylate) salt and p-toluenesulfonate (tosylate) salt, etc. It is obvious to those skilled in the art that any salts suitable for the purpose of the present invention may also be used and such salts may be prepared by a conventional salt preparation method known in the art.

In addition, the compounds of formula 1 may have asymmetric centers, and thus exist in different enantiomeric forms. All optical isomers and (R) and (S) stereoisomers of the compounds of formula 1, and mixtures thereof, also fall within the scope of the present invention. The present invention encompasses the use of racemates, one or more enantiomeric forms, one or more diastereomeric forms, or mixture thereof, and also encompasses an isomer separation method or preparation process.

Methods for Preparation of Tricyclic Derivative Compounds

The present invention also provides methods for preparation of the tricyclic derivative compounds represented by formula 1, optical isomers thereof, racemates thereof, or pharmaceutically acceptable salts thereof.

Preferably, the compounds of formula 1 may be prepared by the methods shown in the reaction schemes below, but the scope of the present invention is not limited to such preparation methods. Particularly, any person skilled in the art will easily understand that the compounds of formula 1 can be prepared by various methods using conventional techniques well known in the art.

The reaction schemes below illustrate each step of methods for preparing representative compounds according to the present invention, and a number of compounds of the present invention may be prepared by alterations or modifications, including changing reagents, solvents and reaction sequence, which are used in the preparation processes shown in reaction schemes 1 to 3.

Preparation Method 1

Specifically, as shown in reaction scheme 1 below, the tricyclic derivatives of the present invention, optical isomers thereof, racemates thereof, or pharmaceutically acceptable salts thereof, may be prepared by a method comprising the steps of:

(1) preparing an acid chloride using a reagent that converts a nicotinic acid compound of formula 2 to the acid chloride, and subjecting the acid chloride to an amidation reaction with an aniline of formula 3, or subjecting the nicotinic acid compound of formula 2 to a coupling reaction with the aniline of formula 3, thereby preparing a compound of formula 4;

(2) introducing a protection group into the compound of formula 4, prepared in step (1), thereby preparing an N-protected compound of formula 5;

(3) cyclizing the compound of formula 5, prepared in step (2), in the presence of a metal catalyst, thereby preparing a compound of formula 6;

(4) subjecting the compound of formula 6, prepared in step (3), to a ring-reducing reaction with hydrogen in the presence of a palladium (Pd) catalyst, thereby preparing a compound of formula 7;

(5) reducing the compound of formula 7, prepared in step (4), with a reducing agent such as lithium aluminum hydride (LAH), thereby preparing a compound of formula 8;

(6) subjecting the compound of formula 8, prepared in step (5), to halogenation and an amination reaction with an amine compound, thereby preparing a compound of formula 9; and (7) removing the protection group from the compound of formula 9, prepared in step (6), by a deprotection reaction, thereby preparing a compound of formula 1a.

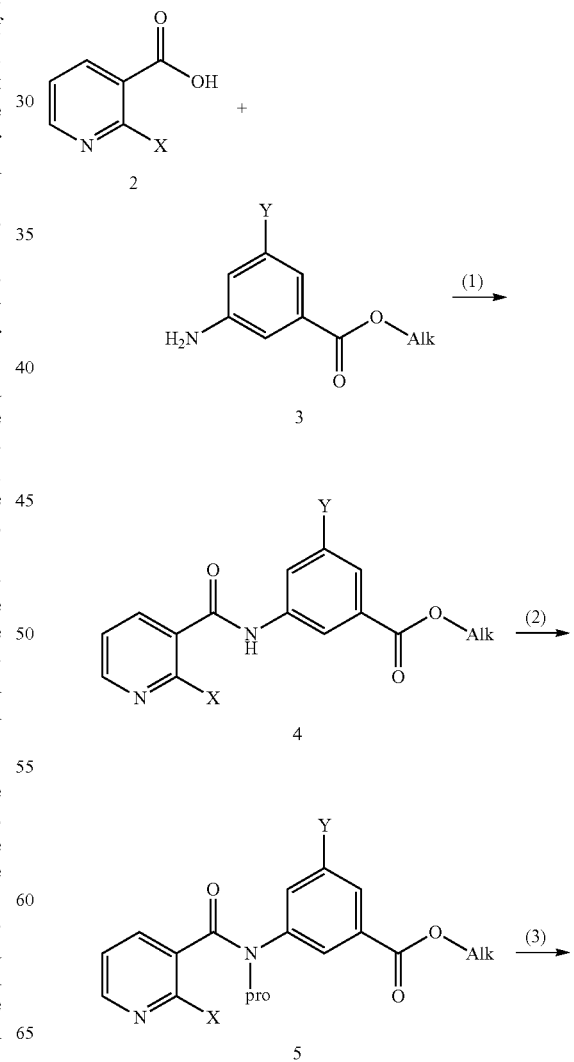

[Reaction Scheme 1]

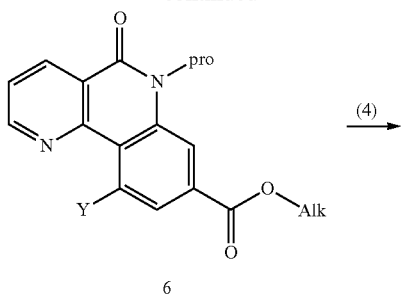

(4)

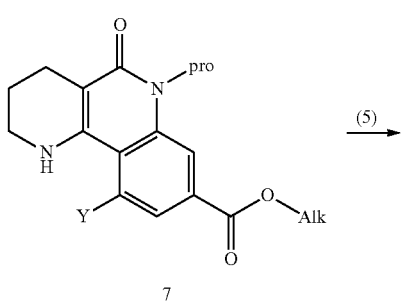

(5)

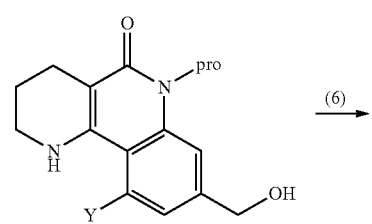

(6)

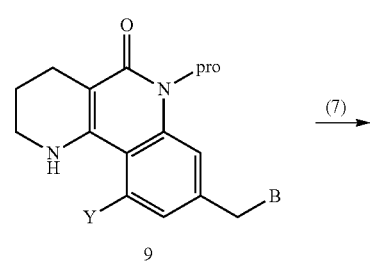

(7)

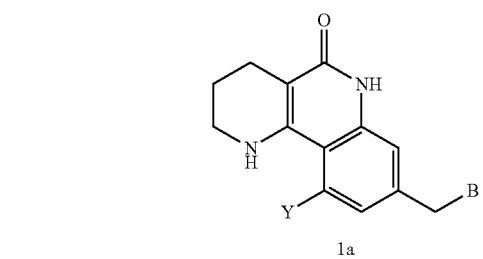

1a wherein

X is a halogen atom;

Y is H, $C_1$-$C_3$alkoxy or a halogen atom;

Alk is a $C_1$-$C_{10}$ straight or branched chain alkyl;

pro is a protection group selected from the group consisting of aryl group, benzyl group, benzyloxymethyl group, paramethoxybenzyl (PMB) group and methoxymethyl (MOM) group; and B is

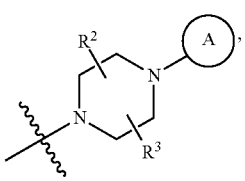

wherein ring A, $R^2$ and $R^3$ are as defined above.

Hereinafter, each step will be described in detail.

In step (1), an acid chloride is prepared using a reagent (the reagent may convert a carboxylic acid such as thionyl chloride or oxalyl chloride to the acid chloride) that converts a commercially readily available nicotinic acid compound of formula 2 to the acid chloride. This reaction is performed without using any solvent or performed using a solvent such as dichloromethane, chloroform, toluene or the like, which does not adversely affect the reaction. The reaction temperature is not particularly limited, but may generally be room temperature to heated temperature, preferably heated temperature. The produced acid chloride is subjected to a general amidation reaction with a compound of formula 3 which is aniline to produce a compound of formula 4. Although this reaction may be performed without using any base, it is generally performed using dichloromethane, chloroform, tetrahydrofuran, diethylether, toluene, N,N-dimethylformamide or the like, which does not adversely affect the reaction, in the presence of an organic amine such as pyridine, triethylamine or diethyl isopropylamine, etc., which is a base that may be used in amidation reactions. The reaction temperature is not particularly limited, but may generally be cold temperature to room temperature, preferably room temperature. Alternatively, 2-halonicotinic acid (formula 2) is subjected to a general amidation reaction with substituted aniline (formula 3) using a coupling reagent, thereby preparing a compound of formula 4. Generally, the coupling reagent used is (1-(3-dimethylaminopropyl)-3-ethylcarbodiimide (EDCI), 1,3-dicyclohexyl carboimide (DCC), 1,1-carbonyl diimidazole or the like, which is commercially readily available. Although this reaction may be performed without using any base, it is generally performed using the solvent acetonitrile, dimethyl formamide, dichloromethane or the like, which does not adversely affect the reaction, in the presence of 4-dimethylaminopyridine, pyridine, triethylamine, diethylisopropylamine, N-methylmorpholine or dimethylphenylamine, etc., which is a base that may be used in amidation reactions. The reaction temperature is not particularly limited, but may be from cold temperature to heated temperature, preferably cold temperature or room temperature.

In step (2), a protection group is introduced into the compound of formula 4, prepared in step (1), thereby synthesizing a compound of formula 5, which is an N-protected amide intermediate product. The protection group introduced may be alkoxymethyl such as methoxymethyl (MOM) or benzyloxymethyl (BOM), etc. benzyl (Bn) or p-methoxybenzyl (PMB), etc. The base that is used in this reaction is sodium hydride, potassium t-butoxide, potassium carbonate, sodium hydroxide or the like, and the solvent used in this reaction is tetrahydrofuran, N,N-dimethylformamide, acetonitrile, toluene, dichloromethane, water, etc., or a mixture thereof, which does not adversely affect the reaction. The reaction temperature is not particularly limited, but may generally be cold temperature to heated temperature, preferably room temperature.

In step (3), the compound of formula 5, which is an N-protected amide intermediate product prepared in step (2), is subjected to a cyclization reaction in the presence of a metal catalyst, thereby preparing a compound of formula 6. The metal catalyst that is used in this reaction is typically palladium(0) or palladium(II). In addition, tetrakistriphenylphosphine palladium(0) ((PPh$_3$)$_4$Pd), palladium(II) acetate (Pd(OAc)$_2$), tris(dibenzylideneacetone)dipalladium(0) (Pd$_2$dba$_3$) or bis(triphenylphosphine)palladium(II) chloride (PdCl$_2$(PPh$_3$)$_2$), etc., may be used as the metal catalyst. Although this reaction may be performed without using any ligand, it is generally performed using triphenylphosphine (PPh$_3$)4, tributylphosphine (Bu$_3$P), 1,2-bis(diphenylphosphino)propane (DPPP) or (R)-2,2'-bis(diphenylphosphino)-1,1'-binaphthyl ((R)-BiNAP), etc., which is a ligand that is generally used in a cyclization reaction in the presence of a metal catalyst. Bases that may be used in this reaction include potassium carbonate, sodium carbonate, silver carbonate, diethylisopropylamine, and the like, and the reaction is performed using a solvent such as N,N-dimethylformamide, benzene, xylene or acetonitrile, etc., which does not adversely affect the reaction. The reaction temperature is not particularly limited, but may generally be room temperature to heated temperature, preferably heated temperature.

In step (4), the compound of formula 6, prepared in step (3), is subjected to a ring-reducing reaction with hydrogen in the presence of a palladium (Pd) catalyst, thereby preparing a compound of formula 7. This reaction is performed using an organic solvent such as alcohol, chloroform, dichloromethane, ethyl acetate, etc., or a mixture thereof, which does not adversely affect the reaction. The reaction temperature is not particularly limited, but is generally room temperature.

In step (5), the compound of formula (7), prepared in step (4), is reduced with a reducing agent such as lithium aluminum hydride (LAH) or sodium borohydride (NaBH$_4$), thereby obtaining a compound of formula (8). The reducing agent used may generally be lithium aluminum hydride (LAH), sodium borohydride (NaBH$_4$), diisobutyl aluminum hydride (DIBAL-H) or the like, which is commercially readily available. In addition, this reaction is preferably performed in a solvent that does not adversely affect the reaction, and examples of solvents that may be used for this purpose include tetrahydrofuran, diethylether, alcohol and the like. The reaction temperature is not particularly limited, but may generally be cold temperature to heated temperature, preferably cold temperature or room temperature.

In step (6), the compound of formula 8, prepared in step (5), is halogenated and aminated with an amine compound to produce a compound of formula 9. In this step, conversion to the halogenated compound may generally be performed using tribromophosphine, tetrabromomethane, thionyl chloride or the like, which converts a hydroxyl group to a halogen, in a solvent such as chloroform, acetonitrile, dichloromethane or the like, which does not adversely affect the reaction. The reaction temperature is not particularly limited, but may generally be cold temperature to room temperature. Furthermore, the halogenated compound may be subjected to a general amination reaction to produce a compound of formula 9. This reaction is generally performed using alcohol such as methanol or ethanol, dichloromethane, chloroform, tetrahydrofuran, diethylether, toluene, N,N-dimethylformamide or the like, which does not adversely affect the reaction, in the presence of an organic amine such as pyridine, triethylamine or diethylisopropylamine, etc., or potassium carbonate, etc., which may be used as a base in amination reactions. The reaction temperature is not particularly limited, but may generally be cold temperature to heated temperature, preferably room temperature to heated temperature.

In step 7, the compound of formula 9, prepared in step (6), is deprotected according to a method known in general organic synthesis, thereby preparing a tricyclic derivative compound of formula 1a.

Preparation Method 2

In addition, according to the present invention, as shown in reaction scheme 2 below, the tricyclic derivative compounds of the present invention, optical isomers thereof, racemates thereof, or pharmaceutically acceptable salts thereof, may be prepared by a method comprising the steps of:

(1) removing the protection group of the compound of formula 8, prepared in step (5) of reaction scheme 1, by a deprotection reaction, thereby preparing a compound of formula 10; and (2) subjecting the compound of formula 10, prepared in step (1), to halogenation and an amination reaction with an amine compound, thereby preparing a compound of formula 1a.

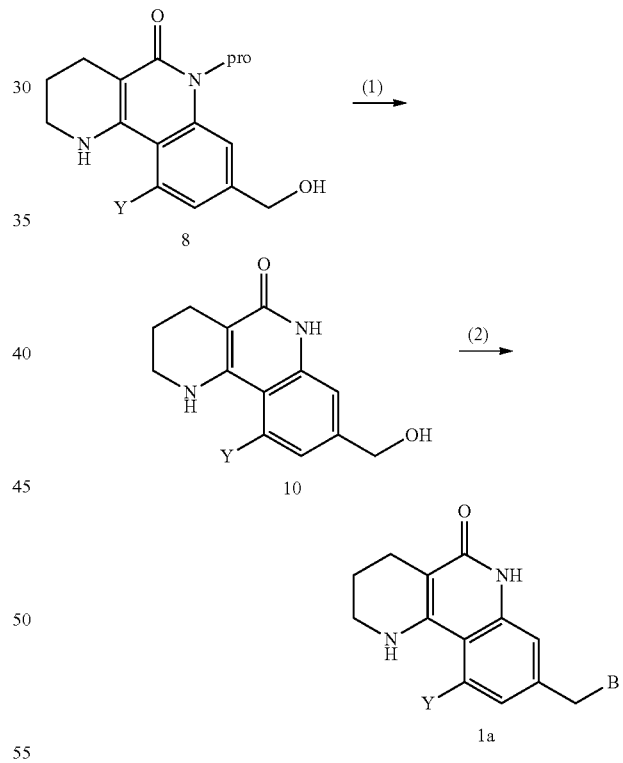

[Reaction Scheme 2]

wherein Y, B and pro are as defined above.

Hereinafter, each step will be described in detail.

In step (1), the compound of formula 8, prepared in step (5) of reaction scheme 1, is deprotected by a method known in general organic synthesis, thereby preparing a compound of formula 10.

In step (2), the compound of formula 10, prepared in step (1), is halogenated and aminated with an amine compound, thereby preparing a compound of formula 1a. In this step, conversion to the halogenated compound may be generally performed using tribromophosphine, tetrabromomethane, thionyl chloride or the like, which converts a hydroxyl group to a halogen, in a solvent such as chloroform, acetonitrile, dichloromethane or the like, which does not adversely affect the reaction. The reaction temperature is not particularly limited, but may be generally cold temperature to room temperature. Furthermore, the halogenated compound may be subjected to a general amination reaction to produce a compound of formula 9. This reaction is generally performed using alcohol such as methanol or ethanol, dichloromethane, chloroform, tetrahydrofuran, diethylether, toluene, N,N-dimethylformamide or the like, which does not adversely affect the reaction, in the presence of an organic amine such as pyridine, triethylamine or diethylisopropylamine, etc., or potassium carbonate, etc., which may be used as a base in amination reactions. The reaction temperature is not particularly limited, but may be generally cold temperature to heated temperature, preferably room temperature to heated temperature.

Preparation Method 3

In addition, according to the present invention, as shown in reaction scheme 3 below, the tricyclic derivative compounds of the present invention, optical isomers thereof, racemates thereof, or pharmaceutically acceptable salts thereof, may be prepared by a method comprising the steps of:

(1) removing the protection group of the compound of formula 7, prepared in step (4) of reaction scheme 1, by a deprotection reaction, thereby preparing a compound of formula 11;

(2) adding an aqueous solution of potassium hydroxide or sodium hydroxide slowly dropwise to the compound of formula 11, prepared in step (1), thereby preparing a compound of formula 12, which is a hydrolyzed carboxylic acid; and (3) subjecting the compound of formula 12, prepared in step (2), to a coupling reaction with an amine compound, thereby preparing a compound of formula 1b.

[Reaction Scheme 3]

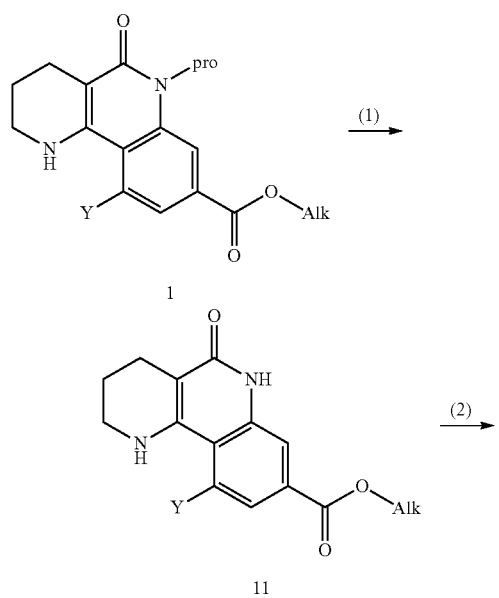

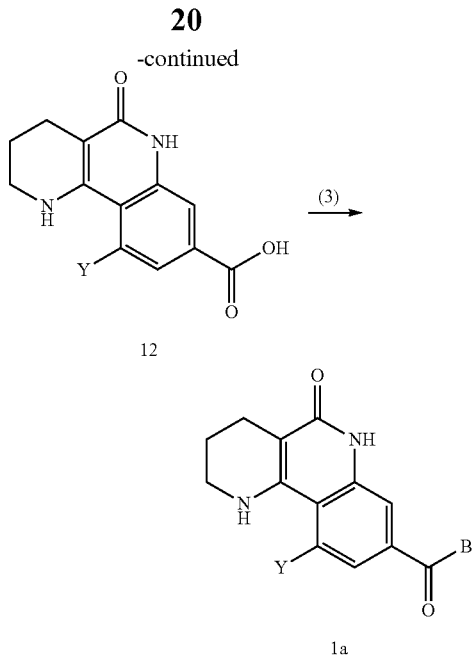

wherein the reaction scheme 3, Y and B are as defined in formula 1 above, Alk is a $C_1$-$C_{10}$ straight or branched chain alkyl, and pro is a protection group such as aryl group, benzyl group, benzyloxymethyl group, para-methoxybenzyl group (PMB), methoxymethyl group (MOM) or the like, preferably para-methoxybenzyl group (PMB) or methoxymethyl group (MOM).

Hereinafter, each step will be described in detail.

In step (1), the compound of formula 7, prepared in step (4) of reaction scheme 1, is deprotected by a method known in general organic synthesis, thereby preparing a compound of formula 11.

In step (2), an aqueous solution of potassium hydroxide or sodium hydroxide is added slowly dropwise to the compound of formula 11, prepared in step (1), thereby preparing a compound of formula (12), which is a hydrolyzed carboxylic acid. This reaction is performed in an alcohol solvent such as methanol or ethanol, which does not adversely affect the reaction. The reaction temperature is not particularly limited, but may be generally performed at cold temperature to heated temperature, preferably room temperature. This reaction may be performed under general ester hydrolysis conditions.

In step (3), the compound of formula 12, prepared in step (2), is subjected to a general amidation reaction with an amine compound in the presence of a coupling reagent, thereby preparing a compound of formula 1b. Generally, the coupling reagent used is 1-ethyl-3-(3-dimethylaminopropyl)-carbodiimide (EDCI), 1,3-dicyclohexyl carboimide (DCC), 1,1-carbonyl diimidazole or the like, which is commercially readily available. Although this reaction may be performed without using any base, it is generally performed using the solvent such as acetonitrile, dimethyl formamide, dichloromethane or the like, which does not adversely affect the reaction, in the presence of 4-dimethylaminopyridine, pyridine, triethylamine, diethylisopropylamine, N-methylmorpholine or dimethylphenylamine, which is a general base that may be used in amidation reactions. The reaction temperature is not particularly limited, but may be cold temperature to heated temperature, preferably cold temperature or room temperature.

The desired products produced according to the reaction schemes as described above may be isolated and purified using conventional methods such as column chromatography, recrystallization or the like.

The compounds of formula 1 according to the present invention may be prepared into pharmaceutically acceptable salts and solvates according to conventional methods known in the art.

Pharmaceutical Composition Comprising Tricyclic Derivative Compound, Use Thereof, and Treatment Method Using the Same The present invention provides a pharmaceutical composition for prevention or treatment of diseases caused by PARP-1, tankyrase-1 or tankyrase-2 activity, the composition containing, as an active ingredient, a tricyclic derivative compound represented by the following formula 1, an optical isomer thereof, a racemate thereof, or a pharmaceutically acceptable salt thereof:

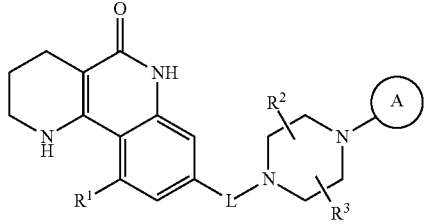

[Formula 1]

wherein L, ring A, $R^1$, $R^2$ and $R^3$ are as defined above.

The diseases caused by PARP-1, tankyrase-1 or tankyrase-2 activity include neuropathic pain, epilepsy, stroke, Alzheimer's disease, Parkinson's disease, amyotrophic lateral sclerosis (ALS), Huntington's disease, schizophrenia, chronic or acute pain, ischemic brain injury, neuronal loss after hypoxia, trauma and nerve damage, neurodegenerative diseases, cardiovascular diseases such as atherosclerosis, hyperlipidemia, cardiovascular tissue damage, coronary artery disease, myocardial infarction, angina pectoris, cardiac shock and the like, diabetic neuropathy, osteoarthritis, osteoporosis, and cancer and the like.

The tricyclic derivative compounds of the present invention or salts thereof can inhibit poly(ADP-ribose)polymerase activity, and thus can be effectively used for prevention or treatment of diseases caused by PARP-1, tankyrase-1 or tankyrase-2 activity, particularly neuropathic pain, neurodegenerative diseases, cardiovascular diseases, diabetic neuropathy, inflammatory diseases, osteoporosis, or cancer.

The pharmaceutical composition of the present invention may be administered by various routes to mammals, including rats, mice, livestock and humans, etc. In the present invention, routes of administration of the pharmaceutical composition according to the present invention include, but are not limited to, oral, intravenous, intramuscular, intraarterial, intramedullary, intradural, intracardiac, transdermal, subcutaneous, intraperitoneal, intranasal, enteral, topical, sublingual or rectal routes.

In addition, the pharmaceutical composition is preferably administered orally or parenterally. As used herein, the term "parenteral" includes subcutaneous, intradermal, intravenous, intramuscular, intra-articular, intra-synovial, intrasternal, intradural, intralesional and intracranial injection or infusion techniques.

The pharmaceutical composition according to the present invention may further contain one or more pharmaceutically acceptable carriers, one or more excipients and/or diluents.

Non-limiting examples of pharmaceutically suitable carriers include solids and/or liquids such as ethanol, glycerol, water and the like. The amount of carrier in the treatment composition can range from about 5 to about 99 wt % based on the total weight of the treatment composition or therapeutic combination. Non-limiting examples of suitable pharmaceutically acceptable excipients and diluents include non-toxic compatible fillers, binders, disintegrants, buffers, preservatives, wetting agents, extenders, antioxidants, lubricants, flavorings, thickeners, coloring agents, surfactant, emulsifiers, suspending agents and the like. Such excipients and diluents include, but are not limited to, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methylhydroxy benzoate, propylhydroxy benzoate, talc, magnesium stearate, and mineral oil, and it is obvious to those skilled in the art that other pharmaceutically acceptable all carriers, excipients and diluents may be used.

For use, the composition containing the compound of the present invention or a salt thereof may be formulated as oral dosage forms such as tablets, powders, granules, pills, capsules, suspensions, emulsions, solutions for internal use, syrups or the like, formulations for external use, suppositories or sterile injectable solutions according to conventional methods.

The pharmaceutical composition according to the present invention may be in the form of a sterile injectable preparation, for example, as a sterile injectable aqueous or oleaginous suspension. This suspension may be formulated according to techniques known in the art using suitable dispersing or wetting agents (e.g., Tween 80), and suspending agents. The sterile injectable formulation may be also a sterile injectable solution or suspension in a non-toxic parenterally-acceptable diluent or solvent, for example, a solution in 1,3-butanediol. Acceptable vehicles and solvents that can be employed are mannitol, water, Ringer's solution or isotonic sodium chloride solution, etc. In addition, sterile fixed oils are conventionally employed as a solvent or suspending medium. For this purpose, any bland fixed oil which has low irritation may be employed, including synthetic mono- or diglycerides. Fatty acids, such as oleic acid and its glyceride derivatives are useful in the preparation of injectable formulations as well as pharmaceutically acceptable natural oils (for example, olive oil or castor oil), especially their polyoxyethylated types.

The pharmaceutical composition according to the present invention may be orally administered in any orally acceptable dose including, but not limited to, capsules, tablets, aqueous suspensions and solutions.

The pharmaceutical composition of the present invention may be also administered in the form of suppositories for rectal administration. These compositions can be prepared by mixing a compound of this invention with a suitable non-irritating excipient which is solid at room temperature but liquid at the rectal temperature. Such materials include, but are not limited to, cocoa butter, beeswax and polyethylene glycols.

Topical administration of the pharmaceutical composition according to the present invention is useful when the desired treatment involves areas or organs readily accessible by topical application. For application topically to the skin, the pharmaceutical composition should be formulated with a suitable ointment containing the active component suspended or dissolved in a carrier. Carriers for topical administration of the compound of this invention include, but are not limited to, mineral oil, liquid paraffin, white petroleum, propylene glycol, polyoxyethylene, polyoxypropylene compound, emulsifying wax and water. Alternatively, the pharmaceutical composition may be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical composition of the present invention may be also topically applied to the lower intestinal tract by rectal suppository formulation or in a suitable enema formulation. Topically-applied transdermal patches are also included in the present invention.

The pharmaceutical composition of the present invention may be administered by nasal aerosol or inhalation. Such compositions are prepared according to techniques well-known in the art of the pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The novel compound described above is contained in the pharmaceutical composition of the present invention in a therapeutically effective amount or a prophylactically effective amount. Although the preferred dose of the compound according to the present invention varies depending on the patient's condition and weight, the severity of the disease, the type of drug, and the route and period of administration, it may be suitably selected by a person skilled in the art. However, for desired effects, the compound of formula 1 according to the present invention may be administered once or several times a day at a dose of 0.0001 to 1000 mg/kg, preferably 0.01 to 500 mg/kg. The composition of the present invention may contain the compound of formula 1 in an amount of 0.0001 to 50 wt % based on the total weight of the composition.

The pharmaceutical composition of the present invention may further contain one or more active ingredients that exhibit the same or similar efficacy, in addition to the compound represented by formula 1, an optical isomer thereof, a racemate thereof, or a pharmaceutically acceptable salt thereof.

In addition, the present invention also provides the use of the tricyclic derivative compound for preparation of a medicament for preventing or treating various diseases induced by PARP-1, tankyrase-1 or tankyrase-2 activity. For preparation of the medicament, the compound represented by formula 1 may be mixed with a pharmaceutically acceptable adjuvant, diluent, carrier or the like, and may also be combined with one or more other active ingredients to provide a combination formulation having synergistic effects.

The present invention also provides a method for prevention or treatment of various diseases induced by PARP-1, tankyrase-1 or tankyrase-2 activity, the method comprising administering an effective amount of the tricyclic derivative compound to mammals, including humans. The method for prevention or treatment according to the present invention includes inhibiting or averting symptom of the disease as well as addressing the disease itself, prior to the onset of symptoms by administering the compound represented by formula 1. In the management of diseases, a prophylactic or therapeutic dose of a particular active ingredient will vary with the nature and severity of the disease or condition, and may also vary according to the route by which the active ingredient is administered. The dose and the dose frequency will also vary according to the age, body weight, and response of the individual patient. Suitable dosing regimens may be readily selected by those skilled in the art with due consideration of such factors. In addition, the method of prevention or treatment according to the present invention may further comprise administering a therapeutically effective amount of an additional active agent helpful for the treatment of the disease together with the compound represented by formula 1, in which the additional active agent can exhibit a synergistic effect with the compound of formula 1 or an assistant effect.

The particulars mentioned in the pharmaceutical composition, use and treatment method of the present invention may be appropriately applied to one another unless contradictory to one another.

Advantageous Effects

The tricyclic derivative compounds according to the present invention can inhibit PARP-1, tankyrase-1 or tankyrase-2 activity, and thus can be effectively used for prevention or treatment of neuropathic pain, neurodegenerative diseases, cardiovascular diseases, diabetic neuropathy, inflammatory diseases, osteoporosis, or cancer.

MODE FOR INVENTION

Hereinafter, the present invention will be described in further detail with reference to examples. However, it will be obvious to those skilled in the art that these examples are for illustrative purposes only and are not intended to limit the scope of the present invention.

Example 1: Synthesis of 8-{[4-(4-methoxyphenyl)piperazin-1-yl]methyl}-1,2,3,4-tetrahydrobenzo[h][1,6]naphthyridin-5(6H)-one Dihydrochloride Step 1: Synthesis of ethyl 3-(2-chloronicotinamido)benzoate

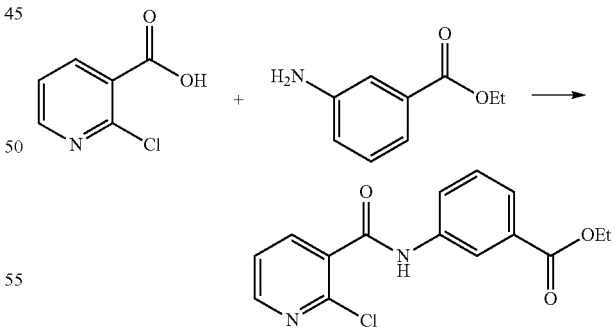

2-chloronicotinic acid (1.049 kg, 6.66 mol) was dissolved in dichloromethane (6 L), and then ethyl-3-aminobenzoate (1.000 kg, 6.05 mol) was added dropwise thereto. The mixture was cooled to 0° C., and 1-ethyl-3-(3-dimethylaminopropyl)-carbodiimide hydrochloride (EDC, 1.600 kg, 9.08 mol) and 1-hydroxy-benzotrizole hydrate (HOBt, 245 g, 1.82 mol) were added thereto, followed by stirring at room temperature for 16 hours. The reaction was stopped by addition of water, and then the organic solvent layer was separated from the aqueous layer and washed with a saturated aqueous solution of sodium chloride. It was dried with anhydrous magnesium sulfate, and concentrated under reduced pressure to remove the solvent, and the obtained solid was washed with ethyl acetate and hexane, and dried under reduced pressure to give the title compound (1.584 kg, 86%, yellow solid).

$^1$H NMR (400 MHz, CDCl$_3$); δ 8.53 (dd, J=1.6 Hz, 4.4 Hz, 1H), 8.41 (s, 1H), 8.21 (dd, J=2.0 Hz, 8.0 Hz, 1H), 8.14 (s, 1H), 8.08-8.05 (m, 1H), 7.89-7.87 (m, 1H), 7.49 (t, J=8.0 Hz, 1H), 7.42 (dd, J=4.8 Hz, 7.2 Hz, 1H), 4.37 (q, J=6.8 Hz, 2H), 1.38 (t, J=6.8 Hz, 3H).

Step 2: Synthesis of ethyl 3-[2-chloro-N-(methoxymethyl) nicotinamido]benzoate

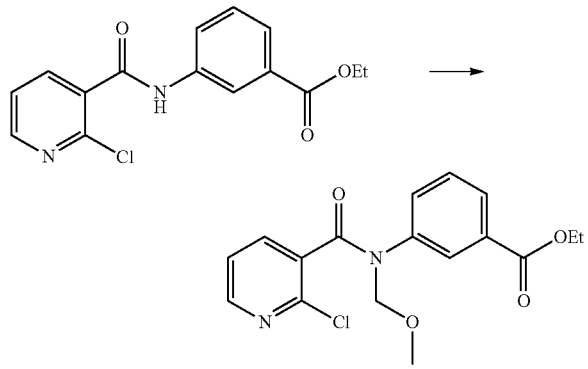

The compound (527 g, 1.73 mol) prepared in step 1 was dissolved in dichloromethane (5.27 L) and cooled to 0° C., and then methoxymethyl chloride (278 g, 3.46 mol) was added thereto. To the reaction solution, sodium iodide (39 g, 0.15 mol) and tetrabutylammonium bromide (223 g, 0.69 mol) were added dropwise. A solution of sodium hydroxide dissolved in water (100 ml) was added for 30 minutes, followed by stirring at room temperature for 10 hours. The reaction was stopped to addition of water, and then the organic solvent layer was separated and concentrated under reduced pressure. Ethyl acetate and water were added to the concentrated residue, and the organic solvent layer was separated, washed with a saturated aqueous solution of sodium chloride, dried with anhydrous magnesium sulfate, and then concentrated under reduced pressure to remove the solvent. The title compound (517 g, 86%, yellow solid) was obtained without further purification (517 g, 86%, yellow solid).

$^1$H NMR (400 MHz, CDCl$_3$); δ 8.24 (d, J=4.8 Hz 1H), 7.87-7.85 (m, 2H), 7.53-7.41 (m, 2H), 7.31 (t, J=8.0 Hz, 1H), 7.12-7.09 (m, 1H), 5.30 (s, 2H), 4.34 (q, J=6.8 Hz, 2H), 3.55 (s, 3H), 1.38 (t, J=6.8 Hz, 3H).

Step 3: Synthesis of ethyl 6-(methoxymethyl)-5-oxo-5,6-dihydrobenzo[h][1,6]naphthyridin-8-carboxylate

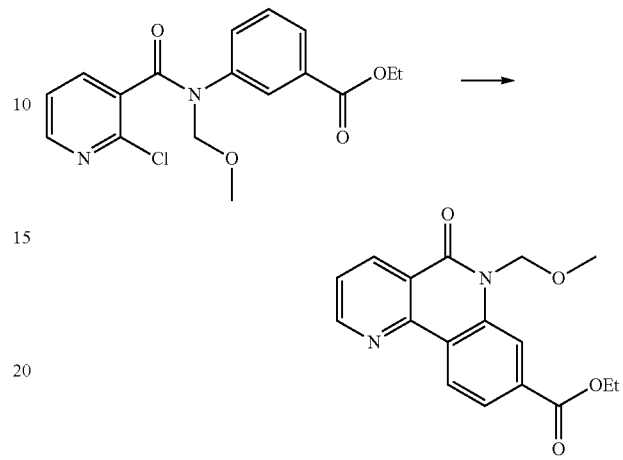

The compound (774 g, 2.22 mol) prepared in step 2 was dissolved in N,N-dimethylformamide (4.5 L), and then tributylphosphine (247 g, 1.23 mol), palladium(II) acetate (137 g, 0.61 mol) and potassium carbonate (676 g, 4.89 mol) were added thereto, followed by reaction at 120° C. for 1 hour. The temperature was lowered to 60° C., and then the reaction was stopped with ice water, followed by filtration to obtain a solid. Methanol was added dropwise to the obtained solid, followed by stirring for 1.5 hours, and then filtration to obtain the title compound (308 g, 44%, white solid).

$^1$H NMR (400 MHz, CDCl$_3$); δ 9.05 (dd, J=2.0 Hz, 4.4 Hz, 1H), 8.93-8.91 (m, 1H), 8.78-8.74 (m, 1H), 8.30 (s, 1H), 8.05-8.03 (m, 1H), 7.59 (dd, J=4.4 Hz, 8.0 Hz, 1H), 5.88 (s, 2H), 4.46 (q, J=6.8 Hz, 2H), 3.50 (s, 3H), 1.46 (t, J=6.8 Hz, 1H).

Step 4: Synthesis of ethyl 6-(methoxymethyl)-5-oxo-1,2,3,4,5,6-hexahydrobenzo[h][1,6]naphthyridin-8-carboxylate

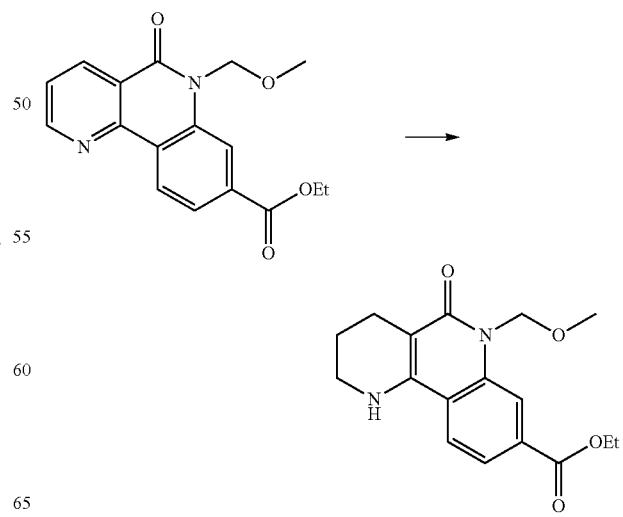

To the compound (257 g, 0.82 mol) prepared in step 3, tetrahydrofuran (3 L) and water (3 L) was added and then 10%-palladium (51 g, 20 wt %) was added. The mixture was stirred under hydrogen gas (4 bar) for 3 hours. The mixture was filtered through a celite filter to remove palladium, and was then extracted with dichloromethane. The extract was concentrated under reduced pressure, and when the remaining amount of dichloromethane reached 2 L, hexane (3 L) was added thereto, followed by stirring for 1.5 hours. The produced solid was filtered to give the title compound (325 g, 52%, white solid).

$^1$H NMR (400 MHz, CDCl$_3$); δ 8.22 (d, J=1.2 Hz, 1H), 7.86 (dd, J=1.2 Hz, 8.4 Hz, 1H), 7.49 (d, J=8.4 Hz, 1H), 5.78 (s, 2H), 4.42 (q, J=7.2 Hz, 2H), 3.49-3.46 (m, 1H), 3.43 (s, 3H), 2.72 (t, J=6.4 Hz, 1H), 2.00-1.98 (m, 1H), 1.43 (t, J=7.2 Hz, 3H).

Step 5: Synthesis of 8-(hydroxymethyl)-6-(methoxymethyl)-1,2,3,4-tetrahydrobenzo[h][1,6]naphthyridin-5-(6H)-one

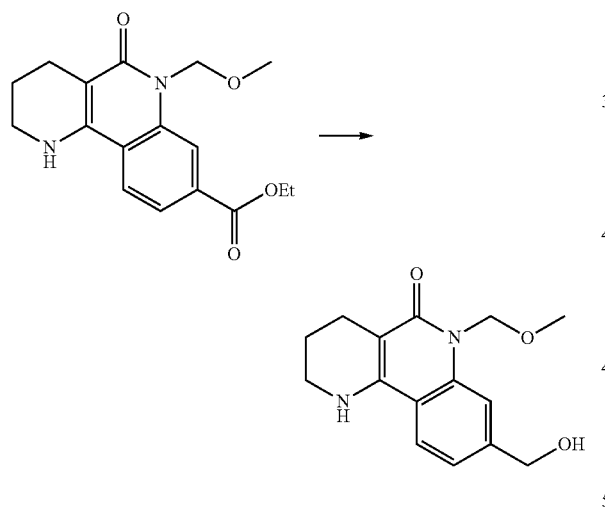

To the compound (50 g, 160 mmol) prepared in step 4, tetrahydrofuran (1 L) and methanol (0.3 L) were added, followed by cooling to 0° C. Sodium borohydride (36 g, 96 mmol) was added slowly to the solution which was then stirred at room temperature for 1 hour, followed by reaction at 60° C. for 12 hours. The reaction solution was cooled to room temperature, and then the reaction was stopped with water, after which the reaction solution was neutralized with 2N hydrochloric acid. The reaction solution was concentrated under reduced pressure, and the solid was filtered and washed with water and acetone, thereby obtaining the title compound (44 g, 99%, yellow solid).

$^1$H NMR (400 MHz, DMSO-d$_6$); δ 7.82 (d, J=8.0 Hz, 1H), 7.41 (s, 1H), 7.14 (d, J=8.0 Hz, 1H), 7.07 (s, 1H), 5.58 (s, 2H), 5.34 (s, 1H), 4.59 (s, 2H), 3.40-3.30 (m, 2H), 3.25 (s, 3H), 2.50-2.46 (m, 2H), 1.83-1.80 (m, 2H).

Step 6: Synthesis of 8-(chloromethyl)-6-(methoxymethyl)-1,2,3,4-tetrahydrobenzo[h][1,6]naphthyridin-5(6H)-one

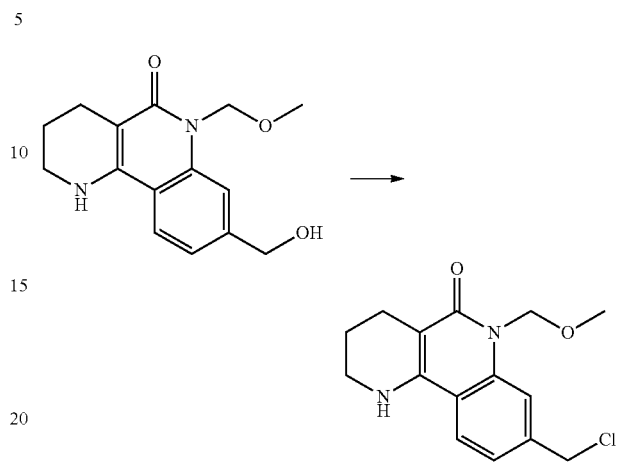

To the compound (54 mg, 0.19 mmol) prepared in step 5, dichloromethane (5 mL) was added, and then thionyl chloride (0.028 ml, 0.39 mmol) was added slowly dropwise at 0° C. The solution was stirred at room temperature for 4 hours. After completion of the reaction, dichloromethane and water at 0° C. were added to the reaction solution which was then dried with anhydrous magnesium sulfate. The resulting material was concentrated under reduced pressure to give the title compound (37 mg, yield: 44%, yellow solid). The obtained compound was used without further purification in the next step.

$^1$H NMR (400 MHz, CD$_3$OD); δ 7.72 (d, J=8. Hz, 1H), 7.30 (s, 1H), 7.21 (dd, J=8.8 Hz, 1.6 Hz, 1H), 4.68 (s, 2H), 3.41 (t, J=5.4 Hz, 2H), 2.59 (t, J=6.2 Hz, 2H), 1.92-1.88 (m, 2H).

Step 7: Synthesis of 6-(methoxymethyl)-8-{[4-(4-methoxyphenyl)piperazin-1-yl]methyl}-1,2,3,4-tetrahydrobenzo[h][1,6]naphthyridin-5(6H)-one

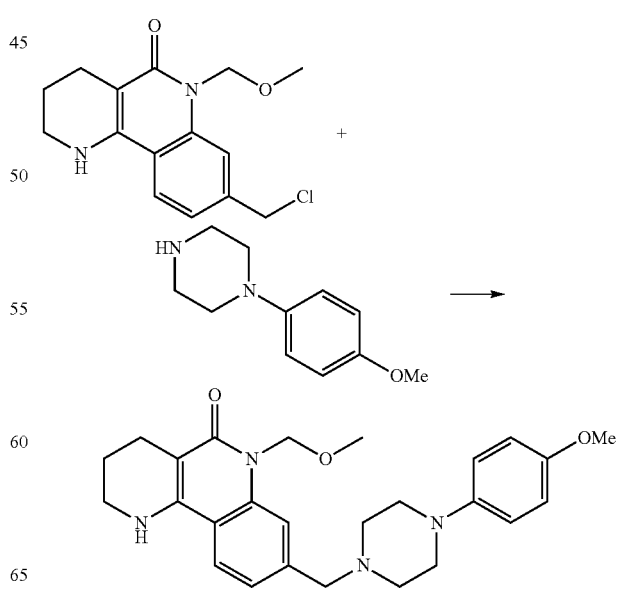

To the compound (100 mg, 0.34 mmol) prepared in step 6, methanol (5.0 ml) was added, and then 1-(4-methoxyphenyl)piperazine (108 mg, 0.41 mmol) and trimethylamine were added. The mixture was stirred at 80° C. for 24 hours. After completion of the reaction, the reaction solution was concentrated, and then extracted with dichloromethane, and the organic solvent layer was dried with anhydrous magnesium sulfate and concentrated under reduced pressure. The obtained residue was purified by column chromatography (hexane:ethyl acetate=1:9) to give the title compound (115 mg, yield: 75%).

$^1$H NMR (400 MHz, CDCl$_3$); δ 7.52 (s, 1H), 7.41-7.39 (m, 1H), 7.26-7.22 (m, 1H), 6.91-6.89 (m, 2H), 6.85-6.82 (m, 2H), 5.75 (s, 2H), 3.77 (s, 3H), 3.67 (s, 2H), 3.49-3.43 (m, 5H), 3.12-3.10 (m, 4H), 2.70-2.63 (m, 6H), 2.10-1.95 (m, 2H).

Step 8: Synthesis of 8-{[4-(4-methoxyphenyl)piperazin-1-yl]methyl}-1,2,3,4-tetrahydrobenzo[h][1,6]naphthyridin-5(6H)-one

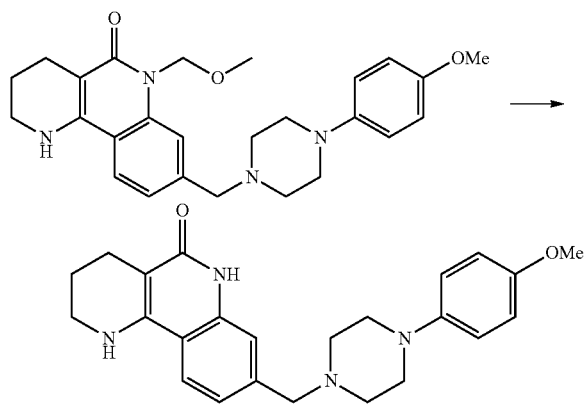

The compound (115 mg, 0.26 mmol) prepared in step 7 was dissolved in dichloromethane (10 ml), and then added to trifluoroacetic acid (2 ml) and heated with a reflux condenser for 24 hours. After completion of the reaction, the reaction solution was extracted with dichloromethane, and extracted once more with dichloromethane in a saturated aqueous solution of sodium hydrogen carbonate. The extract was dried with anhydrous magnesium sulfate and concentrated under reduced pressure, and the obtained residue was purified by column chromatography (dichloromethane:methanol=1:9) to give the title compound (68 mg, yield: 65%).

$^1$H NMR (400 MHz, CDCl$_3$); δ 7.40 (d, J=8.0 Hz, 1H), 7.312 (br, 1H), 7.25-7.20 (m, 1H), 6.90 (d, J=8.8 Hz, 2H), 6.83 (d, J=8.8 Hz, 2H), 4.99 (s, 1H), 3.77 (s, 1H), 3.70 (s, 2H), 3.49-3.46 (m, 2H), 3.14-3.09 (m, 6H), 2.73-2.71 (m, 4H), 1.98-1.97 (m, 2H).

Step 9: Synthesis of 8-{[4-(4-methoxyphenyl)piperazin-1-yl]methyl}-1,2,3,4-tetrahydrobenzo[h][1,6]naphthyridin-5(6H)-one dihydrochloride

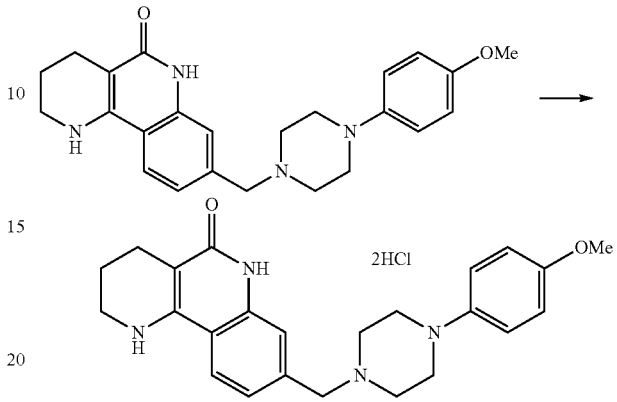

The compound (68 mg, 0.17 mmol) prepared in step 8 was dissolved in methanol (2 ml), and then 1.25M hydrochloric acid methanol solution (2 ml) was added thereto, followed by stirring for 12 hours. After completion of the reaction, the reaction solution was concentrated under reduced pressure to remove the solvent. Then, the solid was produced with ethyl acetate and filtered to give the title compound (83 mg, yield: 100%, solid).

$^1$H NMR (400 MHz, DMSO-d$_6$); δ 11.05 (s, 1H), 11.1-10.9 (br, 1H), 8.34 (d, J=8.4 Hz, 1H), 7.84-7.78 (m, 1H), 7.75 (s, 1H), 7.35 (d, J=9.2 Hz, 1H), 7.27 (d, J=9.6 Hz, 1H), 5.00-4.60 (m, 2H), 4.10 (s, 3H), 4.04 (d, J=13.2 Hz, 2H), 3.80-3.74 (m, 4H), 3.63-3.58 (m, 2H), 3.44-3.41 (m, 2H), 2.92-2.88 (m, 2H), 2.34-2.32 (m, 2H)

Example 2: Synthesis of 8-{[4-(4-fluorphenyl)piperazin-1-yl]methyl}-10-methoxy-1,2,3,4-tetrahydrobenzo[h][1,6]naphthyridin-5(6H)-one Dihydrochloride Using 8-chloromethyl-10-methoxy-6-methoxymethyl-2,3,4,6-tetrahydro-1H-benzo[h][1,6]naphthyridin-5-one and 1-(4-fluorophenyl)piperazine, the title compound (17 mg, yield: 64%, white solid) was obtained in the same manner as described in Example 1.

$^1$H NMR (400 MHz, DMSO-d$_6$); δ 11.91 (br, 1H), 11.66 (br, 1H), 7.45 (s, 1H), 7.15-6.95 (m, 5H), 4.40 (br, 2H), 4.01 (s, 3H), 3.80-3.65 (m, 2H), 3.45-3.30 (m, 2H), 3.30-3.15 (m, 4H), 2.70-2.30 (m, 4H), 1.90-1.70 (m, 2H).

Example 3: Synthesis of 10-ethoxy-8-{[4-(4-fluorophenyl)piperazin-1-yl]methyl}-1,2,3,4-tetrahydrobenzo[h][1,6]naphthyridin-5(6H)-one Trihydrochloride Using 8-chloromethyl-10-ethoxy-6-methoxymethyl-2,3,4,6-tetrahydro-1H-benzo[h][1,6]naphthyridin-5-one and 1-(4-fluorophenyl)piperazine, the compound (36 mg, 0.07 mmol, 87%) was obtained in the same manner as described in Example 1.

$^1$H NMR (400 MHz, DMSO-d$_6$); δ 11.03 (s, 1H), 10.60-10.45 (br, 1H), 7.42 (s, 1H), 7.12-7.08 (m, 2H), 7.04-6.98 (m, 2H), 6.88 (s, 1H), 4.35 (d, J=4.8 Hz, 2H), 4.26 (q, J=7.0

Hz, 2H), 3.73 (d, J=12.8 Hz, 2H), 3.21-3.17 (m, 4H), 3.17-3.06 (m, 4H), 1.80-1.70 (m, 2H), 1.45 (t, J=7.0 Hz, 3H).

Compounds of Examples 4 to 114 were prepared in the same manner as described in Examples 1 to 3, except that substituents were changed as shown in Table 1 below.

TABLE 1

| Example | Structure | NMR |
|---|---|---|
| 4 | 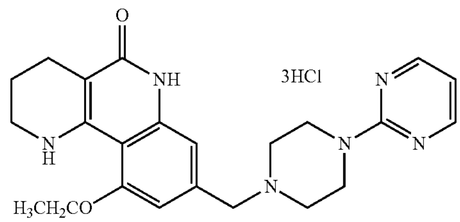 | $^1$H NMR(400 MHz, DMSO-d$_6$); δ 11.68(br s, 1H), 11.53(s, 1H), 8.44(s, 2H), 7.35(s, 1H), 6.95(s, 1H), 6.76(s, 1H), 4.69(d, J = 14.6 Hz, 2H), 4.32(s, 4H), 3.47(t, J = 12.4 Hz, 2H), 3.77(s, 4H), 3.07(s, 2H), 2.51(s, 2H), 1.78(s, 2H), 1.45(t, J = 5.3 Hz, 3H) |
| 5 | 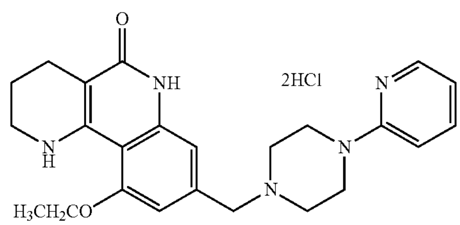 | $^1$H NMR(400 MHz, DMSO-d$_6$); δ 12.10-11.90(m, 1H), 11.62(s, 1H), 8.12(d, J = 4.8 Hz, 1H), 7.94-7.92(m, 2H), 7.39(s, 1H), 7.27(d, J = 8.4 Hz, 1H), 7.00-7.69(m, 2H), 4.48-4.45(m, 2H), 4.36-4.31(m, 4H), 3.70-3.60(m, 2H), 3.45-3.30(m, 4H), 3.30-3.10(m, 2H), 2.50-2.40(m, 2H), 1.85-1.70(m, 2H), 1.45(t, J = 3.8, 3H) |
| 6 | 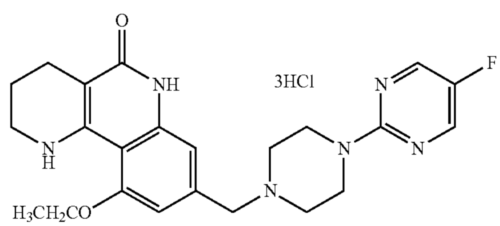 | $^1$H NMR(400 MHz, DMSO-d$_6$); δ 11.79(br, 1H), 11.69(br, 1H), 8.55(s, 2H), 7.41(s, 1H), 6.99(s, 1H), 4.62-4.50(m, 2H), 4.39-4.28(m, 4H), 3.33-3.51(m, 6H), 3.02-3.15(br, 2H), 2.38-2.50(m, 2H), 1.81-1.70(m, 2H), 1.47-1.44(m, 3H) |
| 7 | 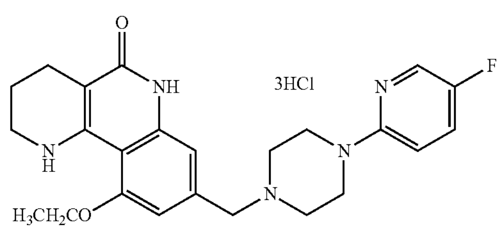 | $^1$H NMR(400 MHz, DMSO-d$_6$); δ 11.81(br, 2H), 8.15(s, 1H), 7.61(t, J = 7.6 Hz, 1H), 7.45(s, 1H), 7.02(s, 1H), 7.00(t, J = 7.6 Hz, 1H), 4.34-4.33(m, 4H), 4.27(d, J = 13.2 Hz, 4H), 3.40-3.31(m, 6H), 3.16-3.11(m, 2H), 1.79(br, 2H), 1.45(t, J = 6.6 Hz, 3H) |
| 8 | 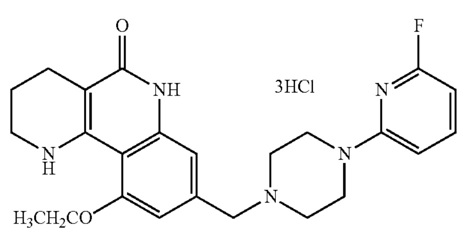 | $^1$H NMR(400 MHz, DMSO-d$_6$); δ 11.72(br, 1H), 11.56(s, 1H), 7.62-7.60(m, 1H), 7.24(s, 1H), 6.98-6.95(m, 2H), 6.76-6.71(m, 1H), 4.33-4.22(m, 6H), 3.48-3.37(m, 6H), 3.09(s, 2H), 2.51(s, 2H), 1.77(s, 2H), 1.43(t, J = 5.6 Hz, 3H) |
| 9 | 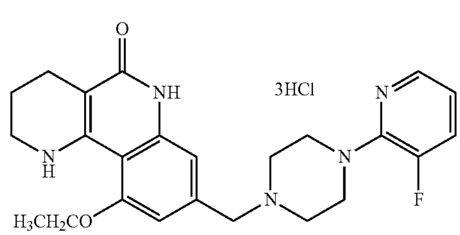 | $^1$H NMR(400 MHz, DMSO-d$_6$); δ 11.72(s, 1H), 11.65(br, 1H), 8.06(s, 1H), 7.62-7.57(m, 1H), 7.39(s, 1H), 7.00(s, 2H), 4.04-4.31(m, 4H), 3.49-3.33(m, 6H), 3.20-3.16(m, 2H), 1.78(s, 2H), 1.44(t, J = 6.8 Hz, 3H) |

TABLE 1-continued

| Example | Structure | NMR |
|---|---|---|
| 10 | 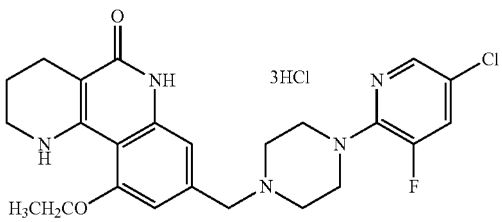 | ¹H NMR(400 MHz, DMSO-d₆): δ 10.65(s, 1H), 8.07(d, J = 2.0 Hz, 1H), 7.83(d, J = 2.0 Hz, 1H), 7.79(d, J = 2.4 Hz, 1H), 7.36(s, 1H), 6.79(s, 1H), 6.62(s, 1H), 4.18(q, J = 6.8 Hz, 2H), 3.47(s, 2H), 3.45-3.35(m, 4H), 3.35-3.25(m, 4H), 2.42(t, J = 6.2 Hz, 2H), 1.75(t, J = 5.4 Hz, 2H), 1.41(t, J = 6.8 Hz, 3H) |
| 11 | 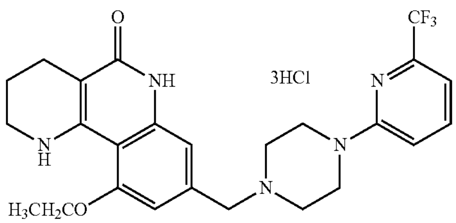 | ¹H NMR(400 MHz, DMSO-d₆); δ 11.55(br, 1H), 11.35(s, 1H), 7.84-7.82(m, 1H), 7.32(s, 1H), 7.28-7.21(m, 1H), 7.17(d, J = 7.3 Hz, 1H), 6.09(s, 1H), 4.42-4.30(m, 6H), 3.45-3.35(m, 6H), 3.12(s, 2H), 2.51(s, 2H), 1.98(s, 2H), 1.44(t, J = 6.3 Hz, 3H) |
| 12 | 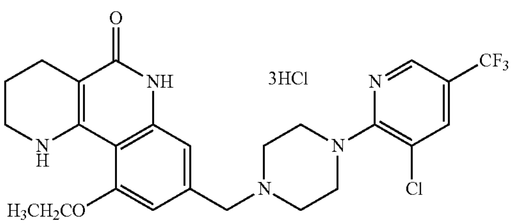 | ¹H NMR(400 MHz, DMSO-d₆); δ 11.72(br, 1H), 11.20(s, 1H), 8.61(s, 1H), 8.28(s, 1H), 7.32(s, 1H), 6.91(s, 1H), 4.34-4.28(m, 6H), 4.10-4.07(m, 2H), 3.35-3.21(m, 6H), 2.51(s, 2H), 1.98(s, 2H), 1.50-1.44(m, 3H) |
| 13 | 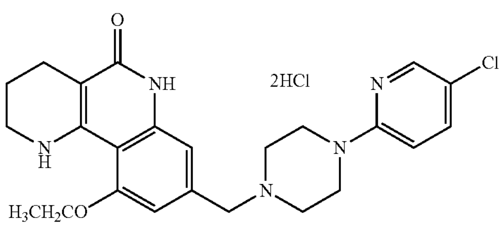 | ¹H NMR(400 MHz, DMSO-d₆); δ 11.19(s, 1H), 11.10-11.00(m, 1H), 8.18(s, 1H), 7.72(d, J = 8.8 Hz, 1H), 7.16(s, 1H), 6.98(d, J = 9.2 Hz, 1H), 6.87(s, 1H), 4.36-4.26(m, 4H), 3.35-3.29(m, 6H), 3.20-3.00(m, 4H), 2.50-2.40(m, 2H), 1.80-1.70(m, 2H), 1.45(t, J = 7.0 Hz, 3H) |
| 14 | 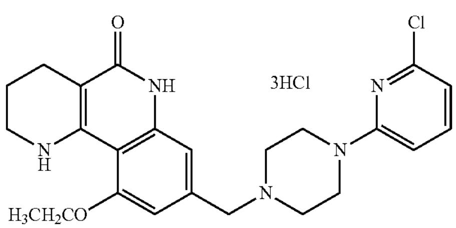 | ¹H NMR(400 MHz, DMSO-d₆); δ 11.49(br, 1H), 11.25(s, 1H), 7.64(t, J = 7.3 Hz, 1H), 7.26(s, 1H), 6.89-6.87(m, 2H), 6.78(d, J = 6.8 Hz, 1H), 4.31-4.29(m, 6H), 3.44-3.35(m, 6H), 3.10(s, 2H), 2.51(s, 2H), 1.77(s, 2H), 1.44(t, J = 6.3 Hz, 3H) |
| 15 | 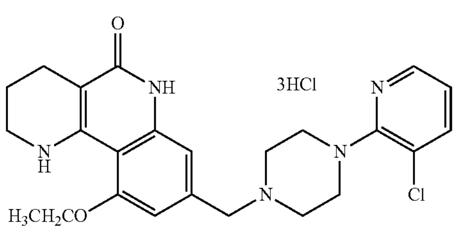 | ¹H NMR(400 MHz, CD₃OD); δ 8.23(dd, J = 4.8, 1.2 Hz, 1H), 7.83(dd, J = 8.0, 1.6 Hz, 1H), 7.36(s, 1H), 7.31(s, 1H), 7.08(q, J = 2.8 Hz, 1H), 4.52(s, 2H), 4.47(q, J = 6.8 Hz, 2H), 4.00(br, 2H), 3.60(t, J = 5.6 Hz, 4H), 3.43(br, 4H), 2.72(t, J = 6.8 Hz, 2H), 2.00-1.96(m, 2H), 1.58(t, J = 6.8 Hz, 3H) |
| 16 | 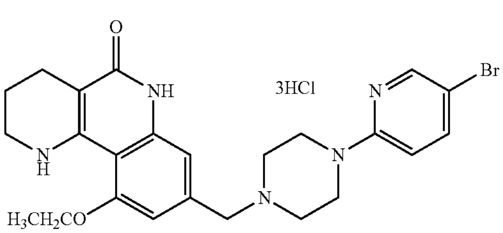 | ¹H NMR(400 MHz, DMSO-d₆); δ 11.49(s, 1H), 10.87(br, 1H), 8.23(s, 1H), 8.12(s, 1H), 7.80(dd, J = 6.8, 1.9 Hz, 1H), 7.54(d, J = 8.8 Hz, 1H), 7.19(s, 1H), 4.36-4.24(m, 6H), 3.38-3.22(m, 6H), 3.11(s, 2H), 2.51(s, 2H), 1.78(s, 2H), 1.45(t, J = 6.8 Hz, 3H) |

TABLE 1-continued

| Example | Structure | NMR |
|---|---|---|
| 17 | 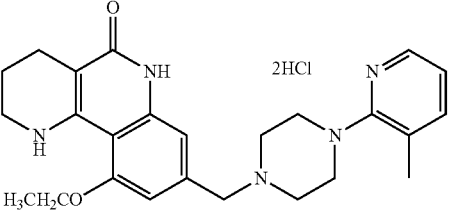 | $^1$H NMR(400 MHz, DMSO-d$_6$); δ 11.71(s, 1H), 11.59(br, 1H), 8.14(s, 1H), 7.81(s, 1H), 7.39(s, 1H), 7.15(s, 1H), 7.04(s, 1H), 4.39(s, 2H), 4.34-4.33(m, 4H), 3.38-3.34(m, 6H), 2.28(s, 3H), 1.77(s, 2H), 1.44(t, J = 6.3 Hz, 3H) |
| 18 | 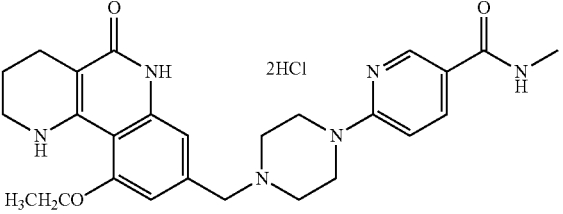 | $^1$H NMR(400 MHz, DMSO-d$_6$); δ 11.73(br, 1H), 11.55(s, 1H), 8.62(s, 1H), 8.39(br s, 1H), 8.07(d, J = 8.7 Hz, 1H), 7.35(s, 1H), 7.02(d, J = 8.7 Hz, 1H), 6.94(s, 1H), 4.32-4.26(m, 6H), 3.49-3.46(m, 2H), 3.36-3.33(m, 4H), 3.11-3.08(m, 2H), 2.76(s, 3H), 2.37-2.32(m, 2H), 1.77(s, 2H), 1.44(t, J = 6.8 Hz, 3H) |
| 19 | 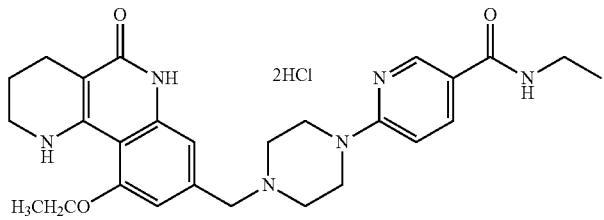 | $^1$H NMR(400 MHz, DMSO-d$_6$); δ 12.11(br, 1H), 12.02(s, 1H), 8.62(s, 1H), 8.16(d, J = 8.3 Hz, 1H), 7.49(s, 1H), 7.10(d, J = 8.3 Hz, 1H), 7.05(s, 1H), 4.55-4.52(m, 4H), 4.37-4.25(m, 6H), 3.59-3.56(m, 2), 3.41-3.14(m, 8H), 1.79(s, 2H), 1.45(t, J = 6.1 Hz, 3H), 1.10(t, J = 7.0 Hz, 3H) |
| 20 | 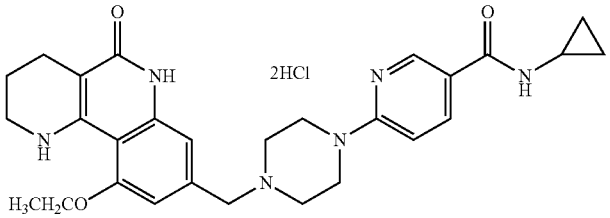 | $^1$H NMR(400 MHz, DMSO-d$_6$); δ 11.76(br, 1H), 11.55(s, 1H), 8.67(s, 1H), 8.06-8.04(m, 1H), 7.36(s, 1H), 7.00(d, J = 8.7 Hz, 1H), 6.94(s, 1H), 4.45-4.48(m, 2H), 4.33-4.25(m, 4H), 3.51-3.49(m, 2H), 3.37-3.33(m, 4H), 3.11-3.08(m, 2H), 1.77(s, 2H), 1.44(t, J = 6.83 Hz, 3H), 0.69(s, 2H), 0.67(s, 2H), 0.55(s, 1H) |
| 21 | 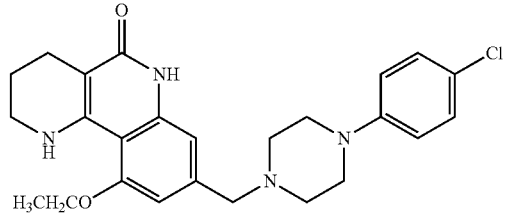 | $^1$H NMR(400 MHz, DMSO-d$_6$); δ 11.90-11.70(m, 2H), 7.44(s, 1H), 7.29(s, 1H), 7.27(s, 1H), 7.01-6.98(m, 3H), 4.80-4.10(m, 6H), 3.80(d, J = 12.0 Hz, 2H), 3.40-3.17(m, 6H), 2.60-2.40(m, 2H), 1.85-1.17(m, 2H), 1.52-1.40(m, 3H) |
| 22 | 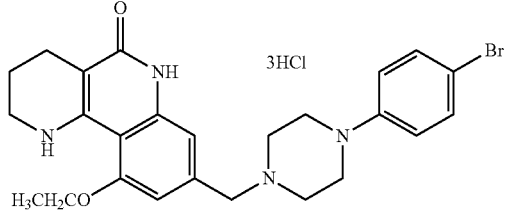 | $^1$H NMR(400 MHz, DMSO-d$_6$); δ 11.50(s, 2H), 7.41(s, 1H), 7.39(s, 1H), 7.34(s, 1H), 6.95-6.93(m, 3H), 4.52-4.29(m, 6H), 3.80(d, J = 12.4 Hz, 2H), 3.37-3.14(m, 6H), 2.50-2.47(m, 2H), 1.80-1.70(m, 2H), 1.44(t, J = 7.0 Hz, 3H) |
| 23 | 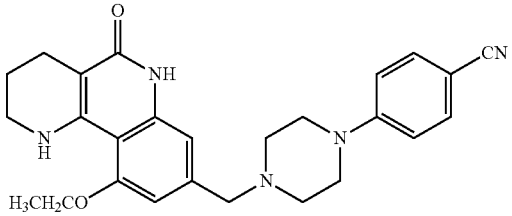 | $^1$H NMR(400 MHz, DMSO-d$_6$); δ 10.66(s, 1H), 7.78(d, J = 8.7 Hz, 1H), 7.58(d, J = 8.7 Hz, 1H), 7.36(s, 1H), 7.02(d, J = 8.7 Hz, 1H), 6.98(d, J = 8.7 Hz, 1H), 6.79(s, 1H), 6.26(s, 1H), 4.24-4.15(m, 6H), 3.48(s, 2H), 3.17(d, J = 8.3(Hz, 2H), 2.42(t, J = 5.8 Hz, 2H), 1.75(s, 2H), 1.41(t, J = 6.8 Hz, 3H) |

TABLE 1-continued

| Example | Structure | NMR |
|---|---|---|
| 24 | 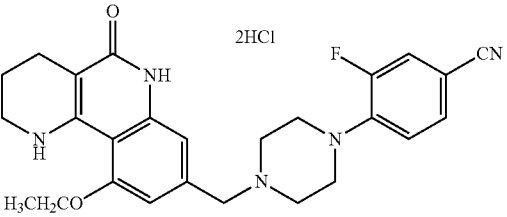 | ¹H NMR(400 MHz, DMSO-d₆); δ 11.59(br, 1H), 11.38(s, 1H), 7.79(d, J = 13.1 Hz, 1H), 7.63(d, J = 8.3 Hz, 1H), 7.31(s, 1H), 7.21(d, J = 8.5 Hz, 1H), 6.93(s, 1H), 4.36-4.29(m, 6H), 3.70-3.67(m, 2H), 3.43-3.36(m, 6H), 3.24(s, 2H), 1.76(s, 2H), 1.44(t, J = 6.5 Hz, 3H) |
| 25 | 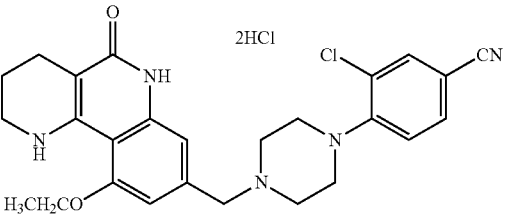 | ¹H NMR(400 MHz, DMSO-d₆); δ 11.60(br, 1H), 11.40(s, 1H), 7.81(d, J = 13.3 Hz, 1H), 7.66(d, J = 8.5 Hz, 1H), 7.31(s, 1H), 7.24(d, J = 8.5 Hz, 1H), 6.93(s, 1H), 4.33-4.29(m, 6H), 3.71-3.62(m, 2H), 3.43-3.36(m, 6H), 3.22(s, 2H), 1.76(s, 2H), 1.45(t, J = 6.7 Hz, 3H) |
| 26 | 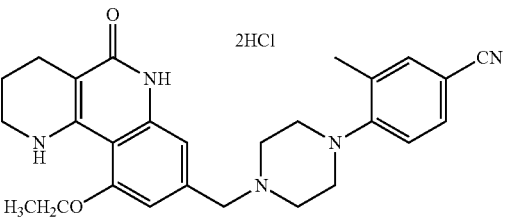 | ¹H NMR(400 MHz, DMSO-d₆); δ 11.43(br, 1H), 11.41(s, 1H), 7.96(s, 1H), 7.64-7.62(m, 2H), 7.35(s, 1H), 7.15(d, J = 8.3 Hz, 1H), 6.95(s, 1H), 4.38(s, 2H), 4.32(d, J = 6.8 Hz, 2H), 3.67-3.64(m, 2H), 3.38-3.23(m, 10H), 2.31(s, 2H), 2.27(s, 3H), 1.77(s, 2H), 1.44(t, J = 6.8 Hz, 3H) |
| 27 | 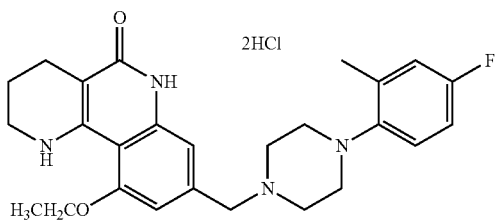 | ¹H NMR(400 MHz, DMSO-d₆); δ 11.30(s, 1H), 11.09(s, 1H), 7.25(s, 1H), 7.07-6.93(m, 4H), 4.36(s, 2H), 4.29(d, J = 7.2 Hz, 1H), 3.35-3.32(m, 4H), 3.30-3.18(m, 2H), 3.12(br, 4H), 2.50-2.46(m, 2H), 2.26(s, 3H), 1.80-1.70(m, 2H), 1.45(t, J = 6.6 Hz, 3H) |
| 28 | 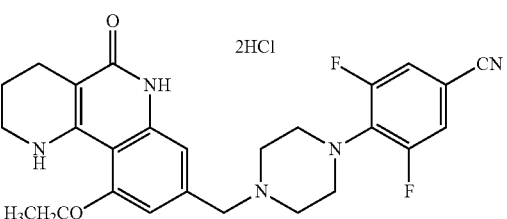 | ¹H NMR(400 MHz, DMSO-d₆); δ 11.28(br, 2H), 7.78(s, 1H), 7.75(s, 1H), 7.24(s, 1H), 6.91(s, 1H), 4.35(br, 2H), 4.29(q, J = 6.8 Hz, 2H), 3.60-3.40(m, 6H), 3.40-3.30(m, 2H), 2.55-2.40(m, 4H), 1.80-1.70(m, 2H), 1.44(t, J = 6.8 Hz, 3H) |
| 29 | 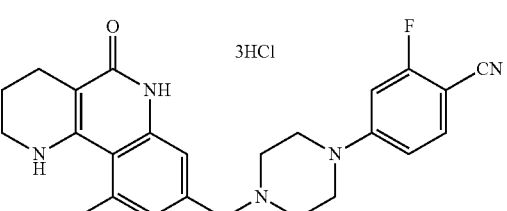 | ¹H NMR(400 MHz, DMSO-d₆); δ 11.62(br, 1H), 11.15(s, 1H), 7.78(d, J = 8.7 Hz, 1H), 7.19(d, J = 8.7 Hz, 1H), 7.03(s, 1H), 6.92(d, J = 8.7 Hz, 1H), 6.86(s, 1H), 4.32-4.27(m, 6H), 4.13-4.01(m, 2H), 3.43-3.34(m, 6H), 3.16(s, 2H), 1.76(s, 2H), 1.44(t, J = 6.8 Hz, 3H) |

TABLE 1-continued

| Example | Structure | NMR |
|---|---|---|
| 30 | 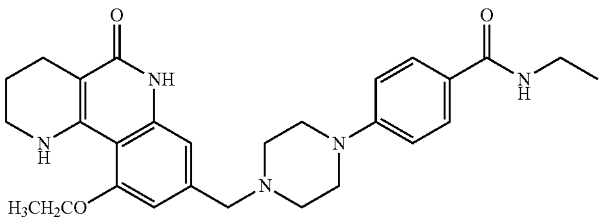 | ¹H NMR(400 MHz, DMSO-d₆); δ 10.64(s, 1H), 8.14(s, 1H), 7.69(d, J = 8.8 Hz, 2H), 7.35(s, 1H), 6.92(d, J = 8.8 Hz, 2H), 6.78(s, 1H), 6.61(s, 1H), 4.16(q, J = 7.2 Hz, 2H), 4.08-4.07(m, 2H), 3.24-3.15(m, 8H), 2.41(t, J = 5.6 Hz, 2H), 1.74(br, 2H), 1.56(s, 2H), 1.40(t, J = 6.8 Hz, 3H), 1.07(t, J = 7.6 Hz, 3H) |
| 31 | 2HCl | ¹H NMR(400 MHz, DMSO-d₆); δ 11.86-11.75(m, 1H), 11.52(s, 1H), 7.84(s, 1H), 7.60(t, 1H, 8.4), 7.41(s, 1H), 7.00-6.97(m, 1H), 6.86-6.78(m, 1H), 4.36-4.32(m, 4H), 3.38-3.30(m, 4H), 3.15(s, 3H), 2.80-2.70(m, 2H), 2.60-2.40(m, 4H), 2.35-2.34(m, 2H), 1.85-1.75(m, 2H), 1.45(t, J = 6.2 Hz, 3H) |
| 32 | 2HCl | ¹H NMR(400 MHz, DMSO-d₆); δ 11.55-11.40(br, 1H), 11.30(s, 1H), 7.89-7.81(m, 2H), 7.32(s, 1H), 6.93(s, 1H), 6.83-6.80(m, 1H), 4.35-4.30(m, 4H), 3.36-3.17(m, 6H), 2.81(t, J = 6.2 Hz, 2h), 2.5(br, 4H), 1.85-1.70(m, 2H), 1.50-1.40(m, 3H), 1.15(t, J = 7.0 Hz, 3H) |
| 33 | 2HCl | ¹H NMR(400 MHz, DMSO-d₆); δ 11.32(s, 1H), 8.51(s, 1H), 7.90(s, 1H), 7.83(d, J = 8.3 Hz, 1H), 7.28(s, 1H), 7.30(d, J = 8.3 Hz, 1H), 6.95(s, 1H), 4.39(s, 2H), 4.33(d, J = 6.8 Hz, 2H), 3.52-3.41(m, 4H), 3.41-3.33(m, 6H), 3.26-3.24(m, 4H), 2.75(s, 3H), 1.77(s, 2H), 1.45(t, J = 6.8 Hz, 3H) |
| 34 | 2HCl | ¹H NMR(400 MHz, DMSO-d₆); δ 11.65(br, 1H), 11.54(s, 1H), 8.49(s, 1H), 7.90(s, 1H), 7.80(d, J = 7.8 Hz, 1H), 7.39(s, 1H), 7.24(d, J = 8.3 Hz, 1H), 6.99(s, 2H), 4.40(s, 2H), 4.33(s, 2H), 3.49(d, J = 9.7 Hz, 2H), 3.37-3.27(m, 8H), 2.82(s, 1H), 1.77(s, 2H), 1.44(t, J = 6.8 Hz, 3H), 0.68(s, 2H), 0.55(s, 2H) |
| 35 | 2HCl | ¹H NMR(400 MHz, DMSO-d₆); δ 11.34(s, 1H), 8.51(s, 1H), 7.90(s, 1H), 7.82(d, J = 8.3 Hz, 1H), 7.28(s, 1H), 7.26(d, J = 8.3 Hz, 1H), 6.95(s, 1H), 4.39(s, 2H), 4.31(d, J = 6.8 Hz, 2H), 3.56-3.45(m, 4H), 3.40-3.36(m, 6H), 3.26-3.24(m, 4H), 2.75(s, 3H), 1.77(s, 2H), 1.44(t, J = 6.8 Hz, 3H) |
| 36 | 2HCl | ¹H NMR(400 MHz, DMSO-d₆); δ 11.50(s, 1H), 11.44(br s, 1H), 8.33(d, J = 3.9 Hz, 1H), 7.68(s, 1H), 7.66(d, J = 8.7 Hz, 1H), 7.37(s, 1H), 7.06(d, J = 7.8 Hz, 1H), 6.98(s, 1H), 4.38(s, 2H), 4.34-4.29(m, 8H), 2.74(s, 3H), 2.27(s, 3H), 1.77(s, 2H), 1.45(t, J = 6.8 Hz, 3H) |

TABLE 1-continued

| Example | Structure | NMR |
|---|---|---|
| 37 | (structure with tetrahydropyridoquinolinone core, H₃CH₂CO substituent, CH₂-piperazine linker, methyl-benzamide with N-ethyl, 2HCl) | ¹H NMR(400 MHz, DMSO-d₆); δ 11.58 (s, 2H), 8.36(s, 1H), 7.68-7.65(m, 2H), 7.42(s, 1H), 7.05(d, J = 7.8 Hz, 1H), 7.00(s, 1H), 4.39(s, 2H), 4.34-4.32(m, 2H), 3.56-3.33(m, 10H), 2.27(s, 3H), 1.77(s, 2H), 1.45(s, 3H), 1.10(s, 3H) |
| 38 | (structure with tetrahydropyridoquinolinone core, H₃CH₂CO substituent, CH₂-piperazine linker, methyl-benzamide with N-cyclopropyl, 2HCl) | ¹H NMR(400 MHz, DMSO-d₆); δ 11.32(s, 2H), 11.22(br, 1H), 8.31(s, 1H), 7.66(s, 1H), 7.63(s, 1H), 7.28(s, 1H), 7.05(d, J = 8.3 Hz, 1H), 6.94(s, 1H), 4.37(s, 2H), 4.32(d, J = 6.9 Hz, 2H), 3.49-3.45(m, 2H), 3.38-3.19(m, 8H), 2.81(s, 1H), 2.26(s, 3H), 1.76(s, 2H), 1.44(t, J = 6.8 Hz, 3H), 0.67(d, J = 6.8 Hz, 2H), 0.53(s, 2H) |
| 39 | (structure with tetrahydropyridoquinolinone core, H₃CO substituent, CH₂-piperazine-2-pyridyl, 2HCl) | ¹H NMR(400 MHz, DMSO-d₆); δ 11.21(br, 2H), 8.13(d, J = 4.0 Hz, 1H), 7.80-7.65(m, 1H), 7.16(s, 1H), 7.10-7.00(m, 1H), 6.87(s, 1H), 6.90-6.80(m, 1H), 4.40-4.20(m, 4H), 3.95(s, 3H), 3.45-3.25(m, 4H), 3.20-3.05(m, 2H), 2.55-2.40(m, 4H), 1.80-1.70(m, 2H) |
| 40 | (structure with tetrahydropyridoquinolinone core, H₃CO substituent, CH₂-piperazine-(3-methyl-2-pyridyl), 2HCl) | ¹H NMR(400 MHz, DMSO-d₆); δ 11.72(br, 2H), 8.13(d, J = 5.2 Hz, 1H), 7.75(d, J = 6.8 Hz, 1H), 7.40(s, 1H), 7.12(t, J = 7.2 Hz, 1H), 7.01(s, 1H), 4.60-4.10(m, 6H), 3.98(s, 3H), 3.70-3.60(m, 2H), 3.60-3.40(m, 2H), 3.40-3.20(m, 4H), 2.26(s, 3H), 1.80-1.70(m, 2H) |
| 41 | (structure with tetrahydropyridoquinolinone core, H₃CO substituent, CH₂-piperazine-(5-fluoro-2-pyridyl), 3HCl) | ¹H NMR(400 MHz, DMSO-d₆); δ 11.68(br, 2H), 8.17(d, J = 5.2 Hz, 1H), 7.72(d, J = 6.9 Hz, 1H), 7.40(s, 1H), 7.12(t, J = 7.2 Hz, 1H), 7.01(s, 1H), 4.64-4.07(m, 6H), 3.99(s, 3H), 3.73-3.24(m, 2H), 3.63-3.41(m, 2H), 3.42-3.22(m, 4H), 1.81-1.73(m, 2H) |
| 42 | (structure with tetrahydropyridoquinolinone core, H₃CO substituent, CH₂-piperazine-(4-cyanophenyl), 2HCl) | ¹H NMR(400 MHz, DMSO-d₆); δ 12.02(br, 2H), 7.70-7.60(m, 2H), 7.55-7.40(br, 1H), 7.10-6.95(m, 3H), 4.39(br, 2H), 4.30-3.90(m, 9H), 3.50-3.20(m, 4H), 3.20-3.10(m, 2H), 1.85-1.70(m, 2H) |

TABLE 1-continued

| Example | Structure | NMR |
|---|---|---|
| 43 | 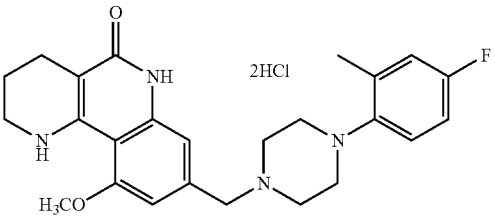 [SMILES: COc1cc(CN2CCN(c3ccc(F)cc3C)CC2)cc2[nH]c(=O)c3c(c12)NCCC3] | $^1$H NMR(400 MHz, DMSO-d$_6$); δ 12.09(br, 1H), 11.74(br, 1H), 7.50(s, 1H), 7.09(s, 1H), 7.05-6.90(m, 3H), 4.37(br, 2H), 3.96(s, 3H), 3.40-3.30(m, 2H), 3.25-3.10(m, 4H), 3.10-2.95(m, 4H), 2.45-2.40(m, 2H), 1.80-1.65(m, 2H) |
| 44 | 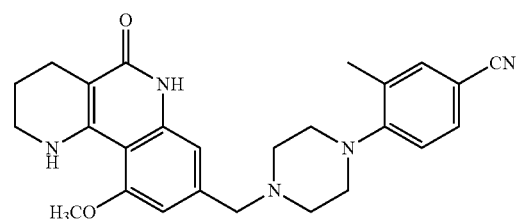 | $^1$H NMR(400 MHz, CD$_3$OD); δ 7.53-7.51(m, 2H), 7.37-7.34(m, 2H), 7.18-7.16(m, 1H), 4.63(S, 2H), 4.13(s, 3H), 3.61-3.55(m, 4H), 3.46-3.27(m, 2H), 2.72-2.67(m, 2H), 2.34(S, 3H), 2.05-1.90(m, 2H) |
| 45 | 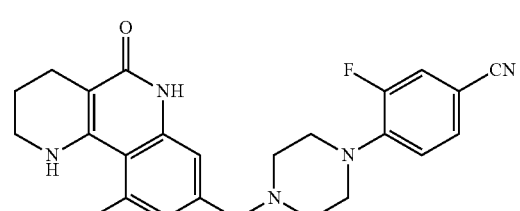 | $^1$H NMR(400 MHz, DMSO-d$_6$); δ 10.68(br, 1H), 7.70(d, J = 13.2 Hz, 1H), 7.57(d, J = 8.4 Hz, 1H), 7.42(s, 1H), 7.12(t, J = 8.8 Hz, 1H), 6.79(s, 1H), 6.61(s, 1H), 4.07(s, 3H), 3.88(br, 2H), 3.45-3.25(m, 6H), 3.25-3.15(m, 4H), 2.45-2.35(m, 2H), 1.80-1.70(m, 2H) |
| 46 | 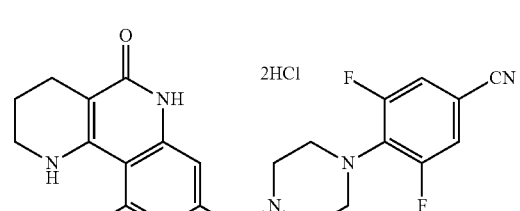 | $^1$H NMR(400 MHz, DMSO-d$_6$); δ 11.89(br, 1H), 11.81(s, 1H), 7.77(s, 1H), 7.74(s, 1H), 7.45(s, 1H), 7.04(s, 1H), 4.40(br, 2H), 4.00(s, 3H), 3.80-3.60(m, 2H), 3.60-3.25(m, 6H), 3.30-3.10(m, 2H), 2.55-2.45(m, 4H), 1.77(m, 2H) |
| 47 | 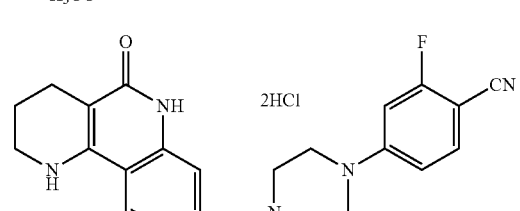 | $^1$H NMR(400 MHz, DMSO-d$_6$); δ 11.74(br, 1H), 11.53(br, 1H), 7.69(t, J = 8.8 Hz, 1H), 7.33(s, 1H), 7.07(d, J = 14 Hz, 1H), 7.00-6.90(m, 2H), 4.35(br, 2H), 4.15-4.05(m, 2H), 3.98(s, 3H), 3.90-3.60(m, 2H), 3.20-3.10(m, 4H), 2.65-2.45(m, 4H), 1.80-1.70(m, 2H) |
| 48 | 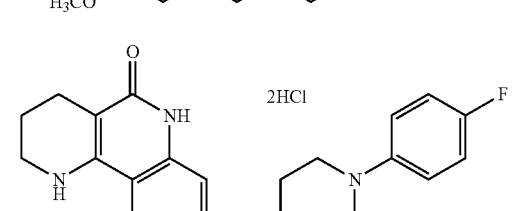 | $^1$H NMR(400 MHz, DMSO-d$_6$); δ 11.76(br, 1H), 11.37(br, 1H), 8.06(d, J = 8.4 Hz, 1H), 7.59(d, J = 8.4 Hz, 1H 7.48(s, 1H), 7.15-7.05(m, 2H), 7.05-6.95(m, 2H), 4.44(br, 2H), 3.75-3.65(m, 2H), 3.40-3.30(m, 2H), 3.30-3.10(m, 4H), 2.60-2.45(m, 4H), 1.85-1.75(m, 2H) |
| 49 | 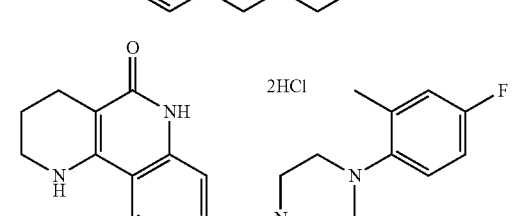 | $^1$H NMR(400 MHz, DMSO-d$_6$); δ 11.44(br, 1H), 11.00(br, 1H), 7.97(d, J = 8.4 Hz, 1H), 7.51(d, J = 8.4 Hz, 1H), 7.40(s, 1H), 7.10-6.95(m, 3H), 4.44(d, J = 4.0 Hz, 2H), 4.20-3.80(m, 2H), 3.30-3.20(m, 2H), 3.15-3.00(m, 4H), 2.60-2.40(m, 4H), 2.25(s, 3H), 1.90-1.70(m, 2H) |

TABLE 1-continued

| Example | Structure | NMR |
|---|---|---|
| 50 | 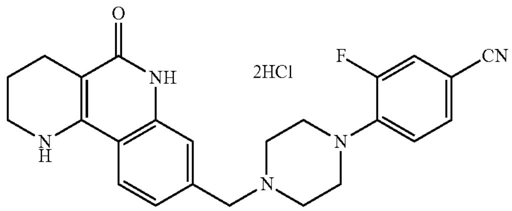 | $^1$H NMR(400 MHz, CD$_3$OD); δ 8.15(d, J = 8.4 Hz, 1H), 7.88(S, 1H), 7.67(d, J = 8.4 Hz, 1H), 7.45-7.43(m, 2H), 7.15-7.11(m, 1H), 4.57(S, 2H), 3.72(d, J = 12.0 Hz, 2H), 3.65-3.48(m, 4H), 3.53-3.24(m, 4H), 2.70-2.68(m, 2H), 1.97-1.96(m, 2H) |
| 51 | 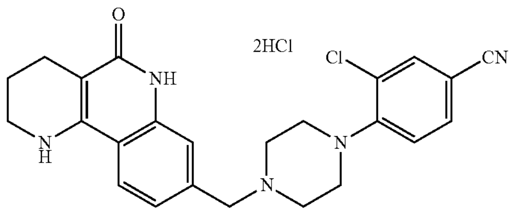 [SMILES: N#Cc1ccc(N2CCN(Cc3ccc4c5c(c(=O)[nH]c4c3)CCCN5)CC2)c(Cl)c1] | $^1$H NMR(400 MHz, CD$_3$OD); δ 8.17(d, J = 8.4 Hz, 1H), 7.86(s, 1H), 7.83(s, 1H), 7.68(d, J = 8.4 Hz, 2H), 7.30(d, J = 8.4 Hz, 1H), 4.62(s, 2H), 3.70-3.56(m, 4H), 3.46(t, J = 10.8 Hz, 2H), 3.34-3.25(m, 4H), 2.74(t, J = 5.8 Hz, 2H), 2.03-2.00(m, 2H) |
| 52 | 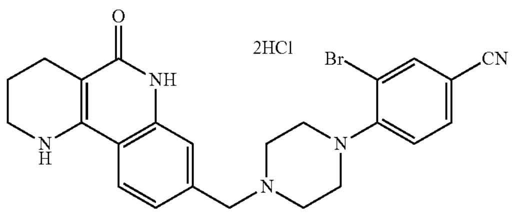 [SMILES: N#Cc1ccc(N2CCN(Cc3ccc4c5c(c(=O)[nH]c4c3)CCCN5)CC2)c(Br)c1] | $^1$H NMR(400 MHz, CD$_3$OD); δ 7.92(d, J = 2.0 Hz, 1H), 7.72(d, J = 8.4 Hz, 1H), 7.65(dd, J = 8.4, 2.0 Hz, 1H), 7.30(s, 1H), 7.24-7.19(m, 2H), 3.67(s, 2H), 3.43(t, J = 3.4 Hz, 2H), 3.17(br, 4H), 2.69(br, 4H), 2.61(t, J = 6.4 Hz, 2H), 1.93(t, J = 5.6 Hz, 2H) |
| 53 | 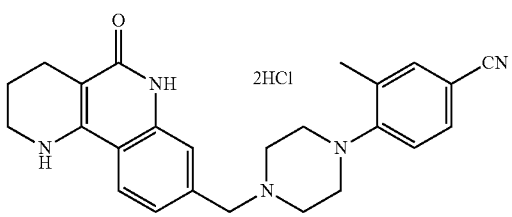 [SMILES: Cc1cc(C#N)ccc1N1CCN(Cc2ccc3c4c(c(=O)[nH]c3c2)CCCN4)CC1] | $^1$H NMR(400 MHz, CD$_3$OD); δ 7.46-7.44(m, 2H), 7.07(d, J = 9.2 Hz, 1H), 6.85(s, 1H), 6.77(s, 1H), 3.94(s, 3H), 3.58(s, 2H), 3.38-3.36(m, 2H), 2.99(br, 4H), 2.63(br, 4H), 2.55(t, J = 6.2 Hz, 2H), 2.27(s, 3H), 1.85-1.82(m, 2H) |
| 54 | 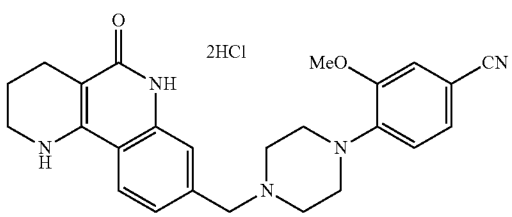 [SMILES: COc1cc(C#N)ccc1N1CCN(Cc2ccc3c4c(c(=O)[nH]c3c2)CCCN4)CC1] | $^1$H NMR(400 MHz, DMSO-d$_6$); δ 11.08(s, 1H), 10.73(br, 1H), 7.87(d, J = 8.8 Hz, 1H), 7.37-7.35(m, 3H), 7.30(s, 1H), 7.01(d, J = 8.0 Hz, 1H), 4.39(s, 1H), 3.82(s, 3H), 3.66-3.05(m, 12H), 1.82-1.70(m, 2H) |
| 55 | 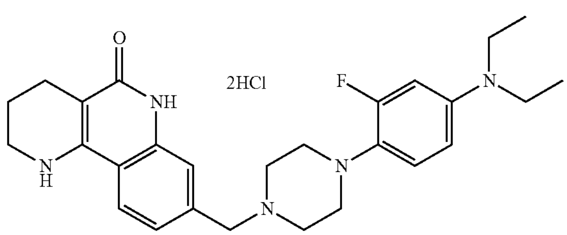 [SMILES: CCN(CC)c1ccc(N2CCN(Cc3ccc4c5c(c(=O)[nH]c4c3)CCCN5)CC2)c(F)c1] | $^1$H NMR(400 MHz, DMSO-d$_6$); δ 10.99(s, 1H), 7.06-7.02(m, 2H), 6.95-6.92(m, 2H), 6.84(d, J = 14.4 Hz, 1H), 6.54(d, J = 13.2 Hz, 1H), 3.52(s, 2H), 3.50-3.30(m, 4H), 3.12-3.02(m, 2H), 2.72-2.65(m, 2H), 2.60-2.38(m, 4H), 2.38-2.30(m, 2H), 1.80-1.70(m, 2H) |
| 56 | 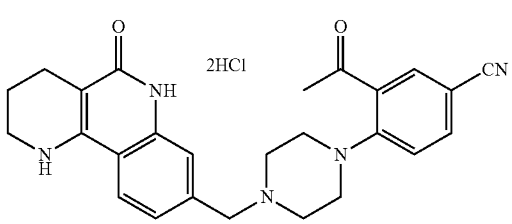 [SMILES: CC(=O)c1cc(C#N)ccc1N1CCN(Cc2ccc3c4c(c(=O)[nH]c3c2)CCCN4)CC1] | $^1$H NMR(400 MHz, DMSO-d$_6$); δ 11.19(s, 1H), 10.73(br, 1H), 7.94(s, 1H), 7.90-7.85(m, 2H), 7.37(d, J = 8.6 Hz, 1H), 7.29(s, 1H), 7.25(d, J = 8.6 Hz, 1H), 4.42(br, 2H), 3.42-3.15(m, 12H), 2.57(s, 3H), 1.78(br, 2H) |

TABLE 1-continued

| Example | Structure | NMR |
|---|---|---|
| 57 | (structure with 2HCl) | ¹H NMR(400 MHz, DMSO-$d_6$); δ 11.47(s, 1H), 11.38(br, 1H), 7.98(s, 1H), 7.83(s, 1H), 7.53(s, 1H), 7.40(s, 2H), 7.14(s, 2H), 7.00(s, 1H), 4.42(s, 2H), 3.64-3.62(m, 2H), 3.40-3.23(m, 10H), 1.80(s, 2H) |
| 58 | (structure) | ¹H NMR(400 MHz, CD$_3$OD); δ 8.15(d, J = 8.4 Hz, 1H), 7.82(s, 1H), 7.64(d, J = 8.4 Hz, 1H), 7.44(s, 1H), 7.42(s, 1H), 4.57(s, 2H), 3.60-3.50(m, 8H), 3.37-2.27(m, 2H), 2.71(t, J = 5.8 Hz, 2H), 2.00-1.98(m, 2H) |
| 59 | (structure with 2HCl) | ¹H NMR(400 MHz, DMSO-$d_6$); δ 11.26(s, 2H), 8.10-8.00(m, 2H), 7.94(d, J = 8.4 Hz, 2H), 7.47(d, J = 8.8 Hz, 1H), 7.35(s, 1H), 7.28-7.24(m, 1H), 4.42(s, 2H), 3.87-3.79(m, 4H), 3.50-3.20(m, 6H), 2.50-2.47(m, 2H), 1.82-1.79(m, 2H) |
| 60 | (structure with 2HCl) | ¹H NMR(400 MHz, DMSO-$d_6$); δ 11.38(br, 2H), 7.95(d, J = 8.4 Hz, 1H), 7.69(t, J = 8.4 Hz, 1H), 7.48(d, J = 8.4 Hz, 1H), 7.34(s, 1H), 7.06(d, J = 13.6 Hz, 1H), 6.92(dd, J = 9.2 Hz, 1.6 Hz, 1H), 4.39(br, 2H), 4.18-4.05(m, 2H), 3.48-3.25(m, 4H), 3.20-3.05(m, 2H), 2.50-2.40(m, 4H), 1.85-1.70(m, 2H) |
| 61 | (structure with 2HCl) | ¹H NMR(400 MHz, DMSO-$d_6$); δ 11.38-11.31(m, 2H), 7.95(d, J = 8.3 Hz, 1H), 7.76(d, J = 8.3 Hz, 1H), 7.47(d, J = 8.3 Hz, 1H), 7.32(s, 1H), 7.26(s, 1H), 7.05(d, J = 8.7 Hz, 1H), 4.38(s, 2H), 4.15(d, J = 13.6 Hz, 2H), 3.43-3.29(m, 6H), 3.16-3.04(m, 4H), 1.80(s, 2H) |
| 62 | (structure with 2HCl) | ¹H NMR(400 MHz, DMSO-$d_6$); δ 11.18(s, 1H), 11.10-10.95(br, 1H), 7.93-7.88(m, 2H), 7.39-7.36(m, 2H), 7.30-7.27(m, 2H), 4.37(s, 2H), 4.21(d, J = 13.6 Hz, 2H), 3.41-3.01(m, 4H), 3.14-3.12(m, 2H), 2.50(br, 4H), 1.79-1.78(m, 2H) |
| 63 | (structure with 2HCl) | ¹H NMR(400 MHz, DMSO-$d_6$); δ 11.24(s, 1H), 11.01(m, 1H), 7.91(d, J = 8.0 Hz, 1H), 7.58(d, J = 8.4 Hz, 1H), 7.48-7.36(m, 1H), 7.30(s, 1H), 7.01(s, 1H), 6.91(d, J = 8.8 Hz, 1H), 4.40-4.39(m, 2H), 4.08-4.01(m, 2H), 3.80-3.50(m, 2H), 3.32-3.25(m, 4H), 3.16-3.11(m, 2H), 2.50-2.47(m, 2H), 2.40(S, 3H), 1.85-1.75(m, 2H) |

TABLE 1-continued

| Example | Structure | NMR |
|---|---|---|
| 64 | 2HCl | ¹H NMR(400 MHz, DMSO-d$_6$); δ 11.27(s, 1H), 10.82(br, 1H), 8.34(s, 1H), 7.94(d, J = 8.3 Hz, 1H), 7.68-7.65(m, 2H), 7.46(d, J = 8.3 Hz, 1H), 7.35(s, 1H), 7.06(d, J = 8.3 Hz, 1H), 4.44(s, 2H), 3.38-3.23(m, 8H), 3.12-3.06(m, 2H), 2.27(s, 3H), 1.80(s, 2H), 1.09(t, J = 7.0 Hz, 3H) |
| 65 | 2HCl | ¹H NMR(400 MHz, DMSO-d$_6$); δ 11.37(s, 1H), 11.10(br, 1H), 8.32(s, 1H), 7.97(d, J = 7.8 Hz, 1H), 7.66-7.63(m, 2H), 7.52(d, J = 7.8 Hz, 1H), 7.39(s, 1H), 7.04(d, J = 8.3 Hz, 1H), 4.44(s, 2H), 3.33-3.22(m, 8H), 3.16-3.13(m, 2H), 2.80(s, 1H), 2.27(s, 3H), 1.80(s, 2H), 0.66(d, J = 5.8 Hz, 3H), 0.54(s, 2H) |
| 66 | 2HCl | ¹H NMR(400 MHz, DMSO-d$_6$); δ 11.14(s, 1H), 10.55(m, 1H), 8.43-8.34(m, 1H), 7.66-7.62(m, 2H), 7.36-7.31(m, 1H), 7.14-.12(m, 1H), 4.43(S, 2H), 3.41-3.16(m, 10H), 2.75(s, 3H), 2.50-2.46(m, 2H), 1.22-1.20(m, 2H) |
| 67 | 2HCl | ¹H NMR(400 MHz, DMSO-d$_6$); δ 11.41(s, 1H), 11.26(br s, 1H), 8.47(s, 1H), 7.97(s, 1H), 7.66-7.63(m, 2H), 7.51(s, 1H), 7.39(s, 1H), 7.13(s, 1H), 4.43(s, 2H), 3.58(s, 2H), 3.34-3.16(m, 8H), 1.80(s, 2H), 1.09(s, 3H) |
| 68 | 2HCl | ¹H NMR(400 MHz, DMSO-d$_6$); δ 11.33(s, 1H), 11.10-11.00(m, 1H), 7.94(d, J = 8.4 Hz, 1H), 7.51-7.44(m, 1H), 7.37(s, 1H), 7.25-7.00(m, 3H), 4.42(s, 2H), 3.96-3.82(m, 2H), 3.47-3.12(m, 10H), 2.60-2.40(m, 2H), 1.90-1.75(m, 2H), 1.06(t, J = 7.6 Hz, 3H) |
| 69 | 2HCl | ¹H NMR(400 MHz, CD$_3$OD); δ 8.17(d, J = 8.0 Hz, 1H), 7.90(s, 1H), 7.69(d, J = 8.4 Hz, 1H), 7.57-7.49(m, 2H), 7.08-7.04(m, 1H), 4.58(s, 1H), 3.67-3.64(m, 2H), 3.54(s, 4H), 3.40-3.38(m, 2H), 2.75-2.69(m, 3H), 1.96-1.94(m, 2H), 0.74-0.71(m, 2H), 0.56-0.55(m, 2H) |
| 70 | 2HCl | ¹H NMR(400 MHz, DMSO-d$_6$); δ 11.18(s, 1H), 10.62(br, 1H), 8.50(s, 1H), 7.91-7.89(m, 2H), 7.81(d, J = 8.3 Hz, 1H), 7.39(d, J = 8.3 Hz, 1H), 7.33(s, 1H), 7.26(d, J = 8.7 Hz, 1H), 4.46(s, 2H), 3.57-3.53(m, 2H), 3.49-3.43(m, 2H), 3.41-3.23(m, 8H, 3.13-3.10(m, 2H), 2.76(s, 3H), 1.79(s, 2H) |

TABLE 1-continued

| Example | Structure | NMR |
|---|---|---|
| 71 | (structure) 2HCl | ¹H NMR(400 MHz, DMSO-d₆); δ 11.17(s, 1H), 10.66(br, 1H), 8.51(s, 1H), 7.94-7.89(m, 2H), 7.82(d, J = 8.3 Hz, 1H), 7.39(d, J = 7.8 Hz, 1H), 7.33(s, 1H), 7.25(d, J = 8.3 Hz, 1H), 4.46(s, 2H), 3.52-3.49(m, 2H), 3.43-3.41(m, 2H), 3.32-3.24(m, 8H), 3.16-3.14(m, 2H), 1.80(s, 2H), 1.09(t, J = 7.0 Hz, 3H) |
| 72 | (structure) 2HCl | ¹H NMR(400 MHz, DMSO-d₆); δ 11.16(s, 1H), 10.65(s, 1H), 8.47(d, J = 4.0 Hz, 1H), 7.90(s, 1H), 7.79(d, J = 9.6 Hz, 1H), 7.38(d, J = 8.4 Hz, 1H), 7.32(s, 1H), 7.24(d, J = 8.8 Hz, 1H), 4.45(s, 2H), 3.51(d, J = 11.6 Hz, 2H), 3.42(d, J = 11.6 Hz, 2H), 3.32(s, 2H), 3.26(d, J = 10.0 Hz, 2H), 3.16-3.10(m, 3H), 2.84-2.81(m, 1H), 2.50-2.45(m, 2H), 1.60-190(m, 2H), 0.71-0.67(m, 2H), 0.50-0.60(m, 2H) |
| 73 | (structure) 2HCl | ¹H NMR(400 MHz, CDCl₃); δ 8.84(br, 1H), 7.96(d, J = 2.0 Hz, 1H), 7.66(dd, J = 8.0, 2.0 Hz, 1H), 7.35(d, J = 8.4 Hz, 1H), 7.17(d, J = 8.0 Hz, 1H), 7.07(s, 1H), 7.04(d, J = 8.4 Hz, 1H), 3.64(s, 2H), 3.46(br, 2H), 3.14-3.13(m, 4H), 2.99(s, 3H), 2.80-2.67(m, 6H), 2.17-1.96(m, 2H) |
| 74 | (structure) 2HCl | ¹H NMR(400 MHz, DMSO-d₆); δ 11.46(s, 1H), 11.27(br s, 1H), 8.55(t, J = 5.1, 1H), 8.09(s, 1H), 7.99(d, J = 8.3 Hz, 1H), 7.87(d, J = 6.8 Hz, 1H), 7.54(d, J = 8.3 Hz, 1H), 7.42(s, 1H), 7.25(d, J = 8.3 Hz, 1H), 4.46(s, 2H), 3.48-3.16(m, 14H), 1.80(s, 2H), 1.09(t, J = 7.3 Hz, 3H) |
| 75 | (structure) 2HCl | ¹H NMR(400 MHz, DMSO-d₆); δ 11.12(br, 1H), 8.48(d, J = 3.6 Hz, 1H), 8.07(s, 1H), 7.89(d, J = 8.4 Hz, 1H), 7.84(d, J = 8.8 Hz, 1H), 7.32(s, 1H), 7.24(d, J = 8.4 Hz, 1H), 4.47(s, 2H), 3.39(br, 4H), 3.40-3.30(m, 2H), 2.70-2.60(m, 2H), 2.5(br, 4H), 1.99(s, 1H), 1.85-1.70(m, 2H), 0.69-0.67(m, 2H), 0.55(br, 1H) |
| 76 | (structure) 2HCl | ¹H NMR(400 MHz, DMSO-d₆); δ 11.40-11.30(m, 2H), 7.94(d, J = 8.4 Hz, 1H), 7.90-7.80(m, 1H), 7.62-7.57(m, 1H), 7.49(d, J = 8.4 Hz, 1H), 6.86-6.83(m, 2H), 4.40(s, 1H), 4.00-3.90(m, 2H), 3.38-3.27(m, 4H), 3.15-3.00(m, 2H), 2.75(s, 3H), 2.50-2.47(m, 4H), 1.90-1.80(m, 2H) |
| 77 | (structure) 2HCl | ¹H NMR(400 MHz, DMSO-d₆); δ 11.53(s, 1H), 11.39(br, 1H), 8.00(d, J = 8.3 Hz, 1H), 7.94-7.90(m, 1H), 7.57(d, J = 9.2 Hz, 1H), 7.54(d, J = 8.7 Hz, 1H), 7.39(s, 1H), 6.86-6.82(m, 2H), 4.41(s, 2H), 4.00(d, J = 13.1 Hz, 1H) 3.34-3.13(m, 12H), 1.80(s, 2H), 1.08(t, J = 7.3 Hz, 3H) |

TABLE 1-continued

| Example | Structure | NMR |
|---|---|---|
| 78 | (structure) 2HCl | $^1$H NMR(400 MHz, DMSO-d$_6$); δ 11.15(s, 1H), 10.69(br, 1H), 7.95(br, 1H), 7.88(d, J = 8.0 Hz, 1H), 7.50(br, 1H), 7.34(d, J = 8.0 Hz, 1H), 7.27(s, 1H), 6.83-6.79(m, 2H), 4.39(br, 2H), 3.97 (d, J = 11.2 Hz, 2H), 3.34-3.31(m, 4H), 3.18-3.14(m, 2H), 2.65(br, 1H), 1.78(br, 2H), 0.65-0.64(m, 2H), 0.51(br, 2H) |
| 79 | (structure) 2HCl | $^1$H NMR(400 MHz, DMSO-d$_6$); δ 11.66(s, 1H), 11.46(br s, 1H), 8.03(d, J = 8.2 Hz, 1H), 7.57(d, J = 8.2 Hz, 1H), 7.42(s, 1H), 7.20-7.19(m, 1H), 6.87-6.82(m, 2H), 4.44(s, 2H), 3.93(d, J = 11.7 Hz, 2H), 3.42-3.14(m, 12H), 1.79(s, 2H), 1.09-1.06(m, 3H) |
| 80 | (structure) 2HCl | $^1$H NMR(400 MHz, DMSO-d$_6$); δ 11.27(s, 1H), 10.92(br s, 1H), 8.14-8.13(m, 1H), 7.93(d, J = 8.7 Hz, 1H), 7.43(d, J = 8.3 Hz, 1H), 7.34-7.32(m, 2H), 7.03 (s, 2H), 6.95(d, J = 8.7 Hz, 1H), 4.40(s, 2H), 3.96(d, J = 10.2 Hz, 1H), 3.38-3.27(m, 4H), 3.23-3.16(m, 4H), 2.71(s, 3H), 1.80(s, 2H) |
| 81 | (structure) 2HCl | $^1$H NMR(400 MHz, DMSO-d$_6$); δ 1.15(s, 1H), 10.70-10.50(m, 1H), 8.20-8.18(m, 1H), 7.90(d, J = 8.8 Hz, 1H), 7.35-7.29(m, 2H), 7.04(s, 1H), 6.94(d, J = 10.0 Hz, 1H), 4.40(s, 2H), 3.96-3.94(m, 2H), 3.35-3.30(m, 4H), 3.22-3.13(m, 6H), 2.50-2.40(m, 2H), 1.85-1.70(m, 2H), 1.08(t, J = 7.0 Hz, 3H) |
| 82 | (structure) 2HCl | $^1$H NMR(400 MHz, DMSO-d$_6$); δ 11.13(s, 1H), 10.49(br, 1H), 8.25(d, J = 4.0 Hz, 1H), 7.88(d, J = 8.4 Hz, 1H), 7.32-7.27(m, 2H), 7.02(s, 1H), 6.92(d, J = 7.2 Hz, 1H), 4.39(br, 2H), 3.93(d, J = 9.6 Hz, 4H), 3.33-3.30(m, 2H), 3.15(br, 5H), 2.75-2.65(m, 2H), 1.78(br, 2H), 0.65-0.64(m, 2H), 0.47(br, 2H) |
| 83 | (structure) 2HCl | $^1$H NMR(400 MHz, DMSO-d$_6$); δ 11.24(s, 1H), 11.01(m, 1H), 7.91(d, J = 8.0 Hz, 1H), 7.58(d, J = 8.4 Hz, 1H), 7.48-7.36(m, 1H), 7.30(s, 1H), 7.01(s, 1H), 6.91(d, J = 8.8 Hz, 1H), 4.40-4.39(m, 2H), 4.21(d, 2H), 4.08-4.01(m, 2H), 3.80-3.50(m, 2H), 3.32-3.25(m, 4H), 3.16-3.11(m, 2H), 2.50-2.47(m, 2H), 1.85-1.75(m, 2H), 1.52(t, J = 6.9 Hz, 3H) |
| 84 | (structure) 2HCl | $^1$H NMR(400 MHz, DMSO-d$_6$); δ 11.53(s, 1H), 11.39(br, 1H), 8.00(d, J = 8.3 Hz, 1H), 7.94-7.90(m, 1H), 7.57(d, J = 9.2 Hz, 1H), 7.54(d, J = 8.7 Hz, 1H), 7.39(s, 1H), 6.86-6.82(m, 2H), 4.41(s, 2H), 4.00(d, J = 13.1 Hz, 1H) 3.34-3.13(m, 12H), 1.80(s, 2H), 1.08(t, J = 7.3 Hz, 3H) |

TABLE 1-continued

| Example | Structure | NMR |
|---|---|---|
| 85 | 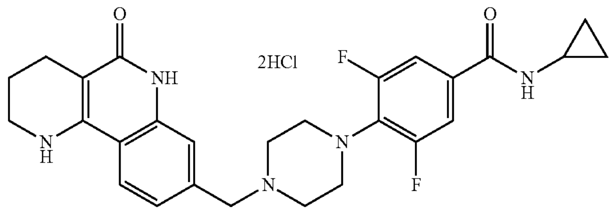 [SMILES: O=C(NC1CC1)c1cc(F)c(N2CCN(Cc3ccc4c5c(c(=O)[nH]c4c3)CCCN5)CC2)c(F)c1] | ¹H NMR(400 MHz, DMSO-d₆); δ 11.22(s, 1H), 11.03(br, 1H), 8.48(d, J = 3.2 Hz, 1H), 7.71(d, J = 8.4 Hz, 1H), 7.53(d, J = 10.0 Hz, 1H), 7.44(d, J = 8.0 Hz, 1H), 7.34(s, 1H), 4.40(s, 2H), 3.57-3.51(m, 4H), 3.41-3.31(m, 6H), 3.19-3.16(m, 2H), 2.80-2.79(m, 1H), 1.80-1.70(m, 2H), 0.67(d, J = 6.0 Hz, 2H), 0.541(s, 2H) |
| 86 | 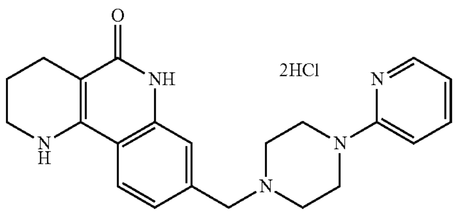 [SMILES: O=c1[nH]c2cc(CN3CCN(c4ccccn4)CC3)ccc2c2c1CCCN2] | ¹H NMR(400 MHz, DMSO-d₆); δ 11.13(s, 1H), 10.75-10.60(br, 1H), 8.15(d, J = 4.4 Hz, 1H), 7.89(d, J = 8.4 Hz, 1H), 7.74-7.64(m, 1H), 7.34(d, J = 8.0 Hz, 1H), 7.28(s, 1H), 7.04-7.70(m, 1H), 6.81-6.80(m, 1H), 4.38(s, 2H), 3.44(br, 4H), 3.32(br, 2H), 2.70-2.65(m, 2H), 2.50(br, 4H), 2.40-2.30(m, 2H) |
| 87 | 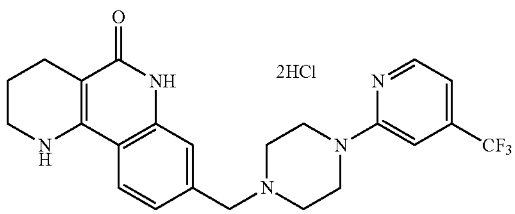 [SMILES: O=c1[nH]c2cc(CN3CCN(c4cc(C(F)(F)F)ccn4)CC3)ccc2c2c1CCCN2] | ¹H NMR(400 MHz, DMSO-d₆); δ 11.67(s, 1H), 11.45-1.35(br, 1H), 8.80(d, J = 5.2 Hz, 1H), 8.34(d, J = 8.4 Hz, 1H), 7.83(d, J = 8.4 Hz, 1H), 7.72(s, 1H), 7.66(s, 1H), 7.43(d, J = 5.6 Hz, 1H), 4.94(d, J = 13.2 Hz, 2H), 4.80-4.79(m, 2H), 3.78-3.75(m, 8H), 3.54-3.51(m, 2H), 2.25-2.15(m, 2H) |
| 88 | 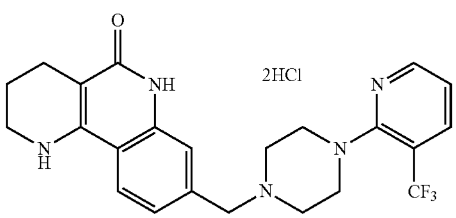 [SMILES: O=c1[nH]c2cc(CN3CCN(c4ncccc4C(F)(F)F)CC3)ccc2c2c1CCCN2] | ¹H NMR(400 MHz, DMSO-d₆); δ 11.73(s, 1H), 11.43(br, 1H), 8.55(s, 1H), 8.12(d, J = 7.8 Hz, 1H), 8.04(d, J = 8.6 Hz, 1H), 7.60(d, J = 8.2 Hz, 1H), 7.48(s, 1H), 7.30-7.27(m, 1H), 4.44(s, 2H), 3.54-3.34(m, 10H), 3.31-3.18(m, 2H), 1.79(s, 2H) |
| 89 | 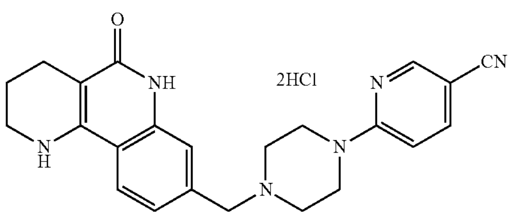 [SMILES: N#Cc1ccc(N2CCN(Cc3ccc4c5c(c(=O)[nH]c4c3)CCCN5)CC2)nc1] | ¹H NMR(400 MHz, DMSO-d₆); δ 11.19(s, 1H), 10.93(s, 1H), 8.60(s, 1H), 7.98(d, J = 9.2 Hz, 1H), 7.90(d, J = 8.4 Hz, 1H), 7.37(d, J = 8.4 Hz, 1H), 7.28(s, 1H), 7.04(d, J = 9.2 Hz, 1H), 4.56(d, J = 13.6 Hz, 2H), 4.37(s, 2H), 3.38-3.32(m, 2H), 3.20-3.00(m, 2H), 2.50-2.47(m, 2H), 1.90-1.70(m, 2H) |
| 90 | 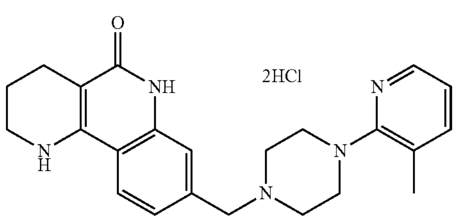 [SMILES: Cc1cccnc1N1CCN(Cc2ccc3c4c(c(=O)[nH]c3c2)CCCN4)CC1] | ¹H NMR(400 MHz, DMSO-d₆); δ 11.78(br, 1H), 11.67(br, 1H), 8.16(d, J = 5.2 Hz, 1H), 8.08(d, J = 8.4 Hz, 1H), 7.88(d, J = 6.8 Hz, 1H), 7.62(d, J = 8.0 Hz, 1H), 7.49(s, 1H), 7.20(t, J = 6.0 Hz, 1H), 4.47(br, 2H), 3.80-3.70(m, 2H), 3.60-3.45(m, 2H), 3.45-3.25(m, 4H), 2.60-2.45(m, 4H), 2.31(s, 3H), 1.85-1.75(m, 2H) |
| 91 | 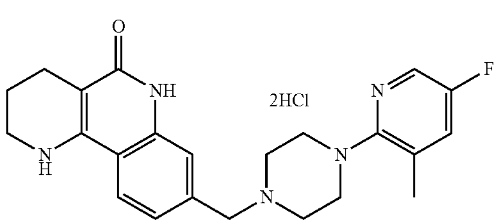 [SMILES: Cc1cc(F)cnc1N1CCN(Cc2ccc3c4c(c(=O)[nH]c3c2)CCCN4)CC1] | ¹H NMR(400 MHz, DMSO-d₆); δ 11.78(s, 1H), 11.36(br, 1H), 8.11(s, 1H), 8.07(d, J = 8.7 Hz, 1H), 7.62-7.57(m, 2H), 7.49(s, 1H), 4.44(s, 2H), 3.44-3.28(m, 12H), 2.25(s, 3H), 1.81(s, 2H) |

TABLE 1-continued

| Example | Structure | NMR |
|---|---|---|
| 92 | (structure with 2HCl) | ¹H NMR(400 MHz, DMSO-d$_6$); δ 12.13(s, 1H), 11.78(br, 1H), 8.47(br, 1H), 8.20(s, 1H), 8.16(d, J = 8.2 Hz, 1H), 7.97(br s, 1H), 7.66(d, J = 8.2 Hz, 1H), 7.56(s, 1H), 4.43(s, 2H), 3.54-3.25(m, 8H), 3.13-3.09(s, 2H), 2.55(s, 2H), 1.80(s, 2H) |
| 93 | (structure with 2HCl) | ¹H NMR(400 MHz, DMSO-d$_6$); δ 11.36(s, 1H), 11.16(br, 1H), 7.94(d, J = 8.2 Hz, 1H), 7.66(d, J = 9.3 Hz, 1H), 7.48-7.42(m, 2H), 7.32(s, 1H), 4.44-4.36(m, 4H), 3.43-3.33(m, 8H), 3.14-3.11(m, 2H), 1.78(s, 2H) |
| 94 | (structure with 2HCl) | 1H NMR(400 MHz, DMSO-d$_6$); δ 11.28(s, 1H), 10.92(br, 1H), 8.30(s, 1H), 8.12(s, 1H), 7.92(d, J = 8.2 Hz, 1H), 7.42(d, J = 8.6 Hz, 1H), 7.33(s, 1H), 4.40(s, 2H), 3.83(d, J = 12.1 Hz, 1H), 3.38-3.18(m, 10H), 1.78(s, 2H) |
| 95 | (structure with 2HCl) | ¹H NMR(400 MHz, CD$_3$OD); δ 8.56(s, 1H), 7.93(d, J = 9.0 Hz, 1H), 7.74(d, J = 8.2 Hz, 1H), 7.31(s, 1H), 7.24(d, J = 8.2 Hz, 1H), 6.81(d, J = 9.0 Hz, 1H), 3.68(br, 6H), 3.43(t, J = 4.8 Hz, 2H), 2.88(s, 3H), 2.63-2.62(m, 6H), 1.97-1.92(m, 2H) |
| 96 | (structure with 2HCl) | ¹H NMR(400 MHz, CD$_3$OD); δ 8.56(d, J = 1.2 Hz, 1H), 7.83(dd, J = 9.0, 2.0 Hz, 1H), 7.73(d, J = 8.2 Hz, 1H), 7.30(s, 1H), 7.23(d, J = 8.2 Hz, 1H), 6.80(d, J = 9.0 Hz, 1H), 3.68(br, 6H), 3.44-3.34(m, 4H), 2.63-2.61(m, 6H), 1.93(t, J = 5.2 Hz, 2H) 1.20(t, J = 7.2 Hz, 3H) |
| 97 | (structure with 2HCl) | ¹H NMR(400 MHz, CD$_3$OD); δ 8.54(d, J = 2.0 Hz, 1H), 7.91(dd, J = 8.8, 2.4 Hz, 1H), 7.73(d, J = 7.9 Hz, 1H), 7.30(s, 1H), 7.22(d, J = 7.9 Hz, 1H), 6.78(d, J = 8.8 Hz, 1H), 3.66-3.64(m, 6H), 3.43 (t, J = 5.2 Hz, 2H), 2.81-2.79(m, 1H), 2.63-2.57(m, 6H), 1.92(t, J = 5.2 Hz, 2H), 0.78-0.75(m, 2H), 0.62-0.58(m, 2H) |
| 98 | (structure with 2HCl) | ¹H NMR(400 MHz, DMSO-d$_6$); δ 11.46(br, 2H), 7.98(d, J = 8.4 Hz, 1H), 7.50(d, J = 8.4 Hz, 1H), 7.37(s, 1H), 7.27(d, J = 3.6 Hz, 1H), 7.02(d, J = 3.6 Hz, 1H), 4.42(s, 2H), 4.08-3.14(m, 12H), 1.81(br, 2H) |

TABLE 1-continued

| Example | Structure | NMR |
|---|---|---|
| 99 | 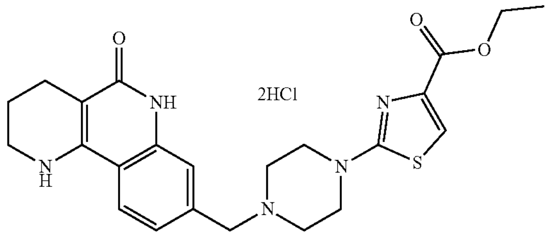 [SMILES: CCOC(=O)c1csc(N2CCN(Cc3ccc4c5c(c(=O)[nH]c4c3)CCCN5)CC2)n1] | ¹H NMR(400 MHz, DMSO-d₆); δ 11.64(s, 1H), 11.60(br, 1H), 8.01(d, J = 8.4 Hz, 1H), 7.81(s, 1H), 7.54(d, J = 8.4 Hz, 1H), 7.41(s, 1H), 4.41(s, 2H), 4.22(q, J = 7.2 Hz, 2H), 4.10-3.30(m, 10H), 2.50-1.75(m, 4H), 1.24(t, J = 7.2 Hz, 3H) |
| 100 | 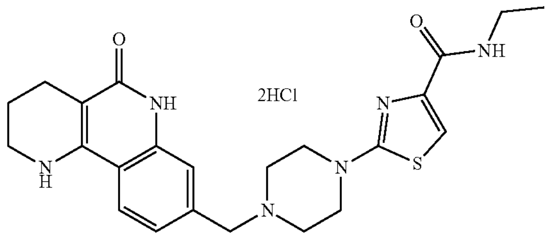 [SMILES: CCNC(=O)c1csc(N2CCN(Cc3ccc4c5c(c(=O)[nH]c4c3)CCCN5)CC2)n1] | ¹H NMR(400 MHz, CD₃OD); δ 7.70(d, J = 8.0 Hz, 1H), 7.34(s, 1H), 7.27(s, 1H), 7.20(d, J = 8.0 Hz, 1H), 3.62(s, 1H), 3.51-3.50(m, 4H), 3.40-3.27(m, 8H), 2.13(s, 2H), 1.90-1.89(m, 2H), 1.16-1.14(m, 3H), 0.88-0.84(m, 1H) |
| 101 | 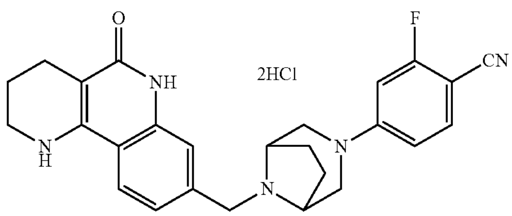 [SMILES: N#Cc1ccc(N2CC3CCC(C2)N3Cc2ccc3c4c(c(=O)[nH]c3c2)CCCN4)cc1F] | ¹H NMR(400 MHz, DMSO-d₆); δ 11.37(br, 1H), 11.32(s, 1H), 7.95(d, J = 8.2 Hz, 1H), 7.65(t, J = 8.4 Hz, 1H), 7.56(d, J = 8.2 Hz, 1H), 7.45(s, 1H), 6.94(d, J = 13.7 Hz, 1H), 6.80(d, J = 9.4 Hz, 1H), 4.28(s, 3H), 3.96(s, 2H), 3.86(d, J = 12.2 Hz, 2H), 3.36-3.32(m, 4H), 2.30(s, 2H), 1.93-1.91(m, 2H), 1.78(s, 2H) |
| 102 | 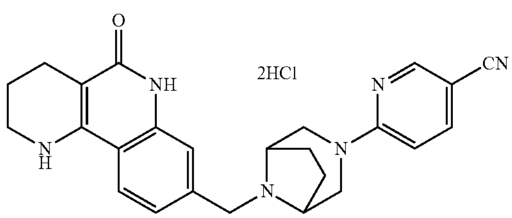 [SMILES: N#Cc1ccc(N2CC3CCC(C2)N3Cc2ccc3c4c(c(=O)[nH]c3c2)CCCN4)nc1] | ¹H NMR(400 MHz, DMSO-d₆); δ 11.24(s, 1H), 11.17(br, 1H), 8.52(s, 1H), 7.93(t, J = 8.0 Hz, 1H), 7.51(d, J = 7.5 Hz, 1H), 7.41(s, 1H), 6.92(d, J = 9.0 Hz, 1H), 4.28(s, 3H), 3.98(s, 1H), 3.31-3.30(m, 4H), 2.30-2.15(m, 4H), 1.84-1.78(m, 4H) |
| 103 | 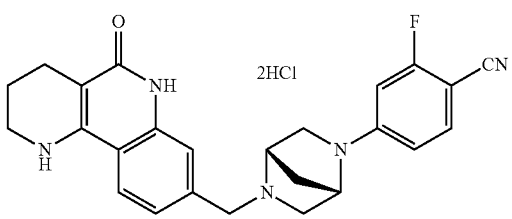 [SMILES: N#Cc1ccc(N2C[C@@H]3C[C@H]2CN3Cc2ccc3c4c(c(=O)[nH]c3c2)CCCN4)cc1F] | ¹H NMR(400 MHz, DMSO-d₆); δ 11.09(m, 2H), 7.90-7.87(m, 1H), 7.61(t, J = 8.0 Hz, 1H), 7.50-7.30(m, 2H), 6.82-6.70(m, 1H), 6.70-6.50(m, 1H), 4.65-4.58(m, 1H), 4.53-4.41(m, 3H), 4.38-4.30(m, 1H), 3.70-3.60(m, 2H), 3.60-3.26(m, 2H), 2.67-2.59(m, 1H), 2.59-2.50(m, 1H), 2.19-2.17(m, 1H), 1.85-1.79(m, 2H) |
| 104 | 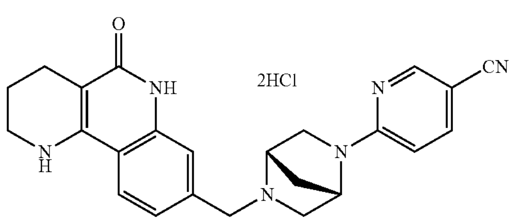 [SMILES: N#Cc1ccc(N2C[C@@H]3C[C@H]2CN3Cc2ccc3c4c(c(=O)[nH]c3c2)CCCN4)nc1] | ¹H NMR(400 MHz, DMSO-d₆); δ 11.70(br, 1H), 11.44(s, 1H), 10.68(br, 1H), 8.55(s, 1H), 7.98-7.50(m, 3H), 7.42(s, 1H), 5.20-3.97(m, 5H), 3.65-3.36(m, 5H), 2.63-1.76(m, 6H) |
| 105 | 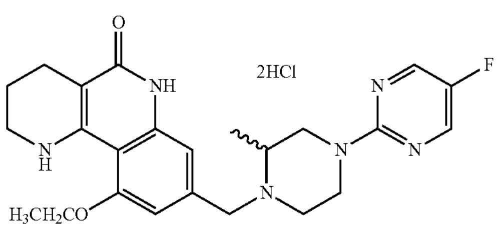 | ¹H NMR(400 MHz, DMSO-d₆); δ 11.81(br, 1H), 11.52(s, 1H), 8.54-8.52(m, 2H), 7.53(s, 1H), 7.03(s, 1H), 4.82-4.78(m, 2H), 4.80(d, J = 12.0 Hz, 1H), 4.58(d, J = 9.6 Hz, 1H), 4.51-4.24(m, 3H), 3.47-3.33(m, 2H), 3.32-3.24(m, 2H), 2.50(br, 2H), 1.90-1.78(m, 2H), 1.57(s, 3H), 1.46-1.43(m, 3H) |

TABLE 1-continued

| Example | Structure | NMR |
|---|---|---|
| 106 | 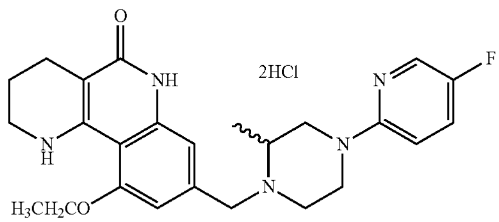 | $^1$H NMR(400 MHz, DMSO-d$_6$); δ 11.90-11.80(br, 1H), 11.72(s, 1H), 8.14(s, 1H), 7.62-7.61(m, 2H), 7.44(s, 1H), 7.02-6.99(m, 2H), 4.79(d, J = 12.8 Hz, 1H), 4.38-4.19(m, 4H), 4.06-4.01(m, 2H), 3.56-3.29(m, 6H), 3.05-2.90(m, 2H), 1.85-1.70(m, 2H), 1.57(d, J = 6.0 Hz, 2H), 1.46-1.43(m, 3H) |
| 107 | 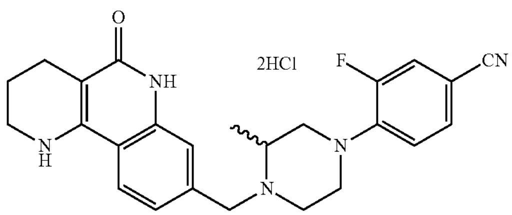 [SMILES: CC1CN(c2ccc(C#N)cc2F)CCN1Cc1ccc2c3c(c(=O)[nH]c2c1)CCCN3] | $^1$H NMR(400 MHz, DMSO-d$_6$); δ 11.07(s, 1H), 10.63(s, 1H), 7.89(d, J = 8.0 Hz, 1H), 7.78(d, J = 13.2 Hz, 1H), 7.63(d, J = 6.8 Hz, 1H), 7.35(d, J = 7.6 Hz, 1H), 7.21(d, J = 8.8 Hz, 1H), 7.05-7.03(m, 1H), 4.81-4.78(m, 1H), 4.44-4.39(m, 1H), 4.21-4.17(m, 1H), 3.86-3.65(m, 2H), 3.30-2.95(m, 4H), 2.45-2.33(m, 2H), 1.85-1.60(m, 2H), 1.54-1.53(m, 3H) |
| 108 | 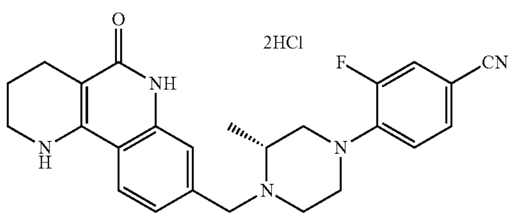 [SMILES: C[C@@H]1CN(c2ccc(C#N)cc2F)CCN1Cc1ccc2c3c(c(=O)[nH]c2c1)CCCN3] | $^1$H NMR(400 MHz, DMSO-d$_6$); δ 11.17(s, 1H), 10.98(br, 1H), 7.90(d, J = 7.8 Hz, 1H), 7.77(d, J = 13.3 Hz, 1H), 7.61(d, J = 8.6 Hz, 1H), 7.41(d, J = 8.2 Hz, 1H), 7.31(s, 1H), 7.22(d, J = 9.0 Hz, 1H), 4.78-4.76(m, 2H), 4.26(s, 2H), 3.66-3.12(m, 8H), 1.77(s, 2H), 1.53-1.52(m, 3H) |
| 109 | 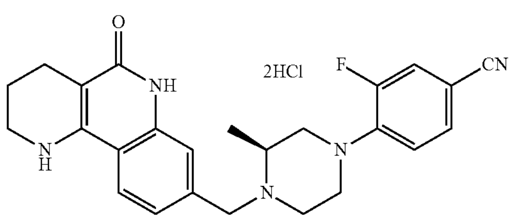 [SMILES: C[C@H]1CN(c2ccc(C#N)cc2F)CCN1Cc1ccc2c3c(c(=O)[nH]c2c1)CCCN3] | $^1$H NMR(400 MHz, DMSO-d$_6$); δ 11.26(s, 1H), 11.14(br, 1H), 7.92-7.09(m, 6H), 4.79(d, J = 12.1 Hz, 2H), 4.15(s, 2H), 3.25-3.05(m, 8H), 1.78(s, 2H), 1.54-1.53(m, 3H) |
| 110 | 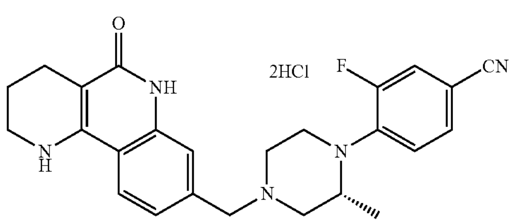 [SMILES: C[C@@H]1CN(Cc2ccc3c4c(c(=O)[nH]c3c2)CCCN4)CCN1c1ccc(C#N)cc1F] | $^1$H NMR(400 MHz, DMSO-d$_6$); δ 11.36(s, 1H), 10.79(br, 1H), 7.94-7.15(m, 6H), 4.49-4.33(m, 4H), 3.66-3.12(m, 8H), 1.77(s, 2H), 1.53-1.52(m, 3H) |
| 111 | 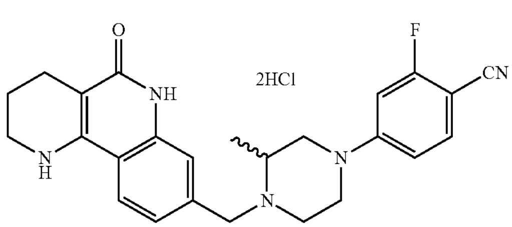 [SMILES: CC1CN(c2ccc(C#N)c(F)c2)CCN1Cc1ccc2c3c(c(=O)[nH]c2c1)CCCN3] | $^1$H NMR(400 MHz, CD$_3$OD); δ 7.99(s, 1H), 7.62(d, J = 8.4 Hz, 1H), 7.37-7.33(m, 1H), 7.12(d, J = 8.0 Hz, 1H), 6.71-6.67(m, 1H), 4.82(s, 2H), 4.57(d, J = 19.6 Hz, 1H), 4.07(d, J = 13.6 Hz, 1H), 3.64-3.52(m, 1H), 3.35-3.31(m, 2H), 3.00-2.95(m, 1H), 2.83-2.72(m, 1H), 2.52(t, J = 6.2 Hz, 2H), 2.40-2.20(m, 1H), 1.85-1.84(m, 1H), 0.81-0.78(m, 3H) |

TABLE 1-continued

| Example | Structure | NMR |
|---|---|---|
| 112 | 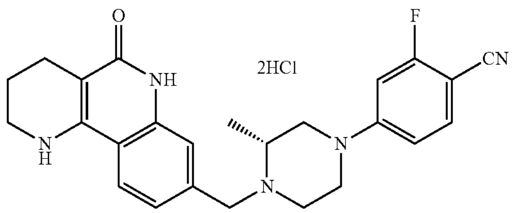 [SMILES: C[C@@H]1CN(c2ccc(C#N)c(F)c2)CCN1Cc1ccc2c3c(c(=O)[nH]c2c1)CCCN3] | ¹H NMR(400 MHz, CD₃OD); δ 7.99(s, 1H), 7.61-6.64(m, 4H), 4.82(s, 2H), 4.55(d, J = 19.1 Hz, 1H), 4.07(d, J = 13.6 Hz, 1H), 3.61-3.33(m, 3H), 3.04-2.70(m, 2H), 2.50(t, J = 6.3 Hz, 2H), 2.41-2.23(m, 1H), 1.83-1.82(m, 1H), 0.81-0.78(m, 3H) |
| 113 | 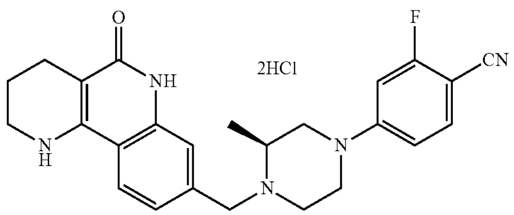 [SMILES: C[C@H]1CN(c2ccc(C#N)c(F)c2)CCN1Cc1ccc2c3c(c(=O)[nH]c2c1)CCCN3] | ¹H NMR(400 MHz, DMSO-d₆); δ 11.08(s, 1H), 10.59(br, 1H), 7.88(d, J = 9.4 Hz, 1H), 7.67(t, J = 8.6H, 1H), 7.31(s, 1H), 7.08-7.04(m, 2H), 6.92(d, J = 9.0 Hz, 1H), 4.77-4.75(m, 2H), 3.45-3.22(m, 8H), 3.01(s, 2H), 1.77(s, 2H), 1.53-1.52(m, 3H) |
| 114 | 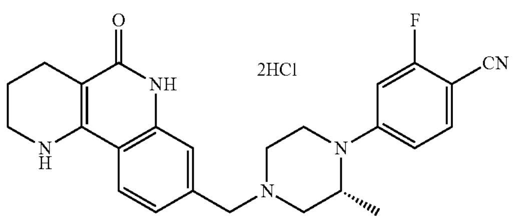 [SMILES: C[C@@H]1CN(Cc2ccc3c4c(c(=O)[nH]c3c2)CCCN4)CCN1c1ccc(C#N)c(F)c1] | ¹H NMR(400 MHz, DMSO-d₆); δ 11.37(s, 1H), 10.82(br, 1H), 7.91-7.06(m, 6H), 4.49-4.33(m, 4H), 3.66-3.12(m, 8H), 1.77(s, 2H), 1.53-1.52(m, 3H) |

Example 115: Synthesis of 8-({4-[4-(trifluoromethyl)phenyl]piperazin-1-yl}methyl)-1,2,3,4-tetrahydrobenzo[h][1,2]naphthyridin-5(6H)-one Dihydrochloride

Step 1: Synthesis of 8-(hydroxymethyl)-1,2,3,4-tetrahydrobenzo[h][1,6]naphthyridin-5-(6H)-one

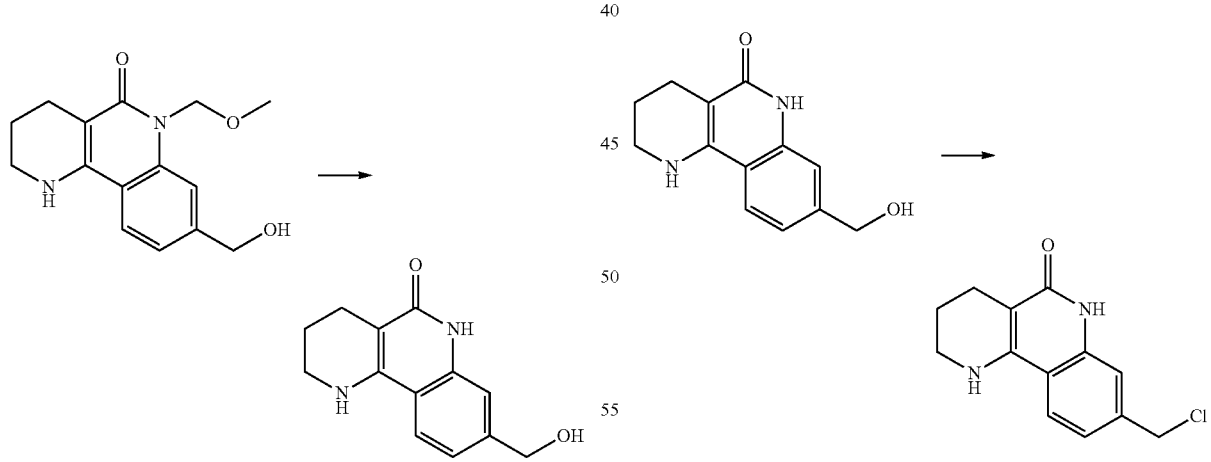

To the compound (34 g, 123 mmol) prepared in step (5) of Example 1, ethanol (0.38 L) was added and then 12N hydrochloric acid (0.34 L, 419 mmol) was added slowly dropwise. The mixture was allowed to react at 90° C. for 4 hours. The reaction mixture was cooled to 0° C., and then neutralized with 4N sodium hydroxide solution. After stirring for 1 hour, the produced solid was filtered and washed with water and ethanol to give the title compound (26 g, 92%, yellow solid).

¹H NMR (400 MHz, DMSO-d₆); δ 10.75 (s, 1H), 7.71 (d, J=8.4 Hz, 1H), 7.17 (s, 1H), 6.99 (d, J=8.4 Hz, 1H), 6.86 (s, 1H), 5.26 (br, 1H), 4.52 (s, 2H), 3.35-3.25 (m, 2H), 2.44 (d, J=6.4 Hz, 2H), 1.84-1.74 (m, 2H).

Step 2: Synthesis of 8-(chloromethyl)-1,2,3,4-tetrahydrobenzo[h][1,6]naphthyridin-5-(6H)-one To the compound (25 g, 110 mmol) prepared in step (1), dichloromethane (0.66 L) was added, and then thionyl chloride (14.5 ml, 199 mmol) was added slowly dropwise at room temperature. The mixture was stirred at room temperature for 12 hours, and then concentrated under reduced pressure to remove the solvent. Water (200 ml) was added at 0° C., followed by neutralization with 4N sodium hydroxide solution. The reaction mixture was stirred for 1 hour, and the produced solid was washed with ethanol, thereby obtaining the title compound (27 g, 99%, yellow solid).

¹H NMR (400 MHz, DMSO-d₆); δ 10.98 (s, 1H), 7.80 (d, J=8.4 Hz, 1H), 7.26 (s, 1H), 7.14 (d, J=8.4 Hz, 1H), 7.00 (br, 1H), 4.79 (s, 2H), 3.32-3.29 (m, 2H), 2.46 (d, J=6.0 Hz, 2H), 1.83-1.75 (m, 2H).

Step 3: Synthesis of 8-({4-[4-(trifluoromethyl)phenyl]piperazin-1-yl}methyl)-1,2,3,4-tetrahydrobenzo[h][1,2]naphthyridin-5(6H)-one

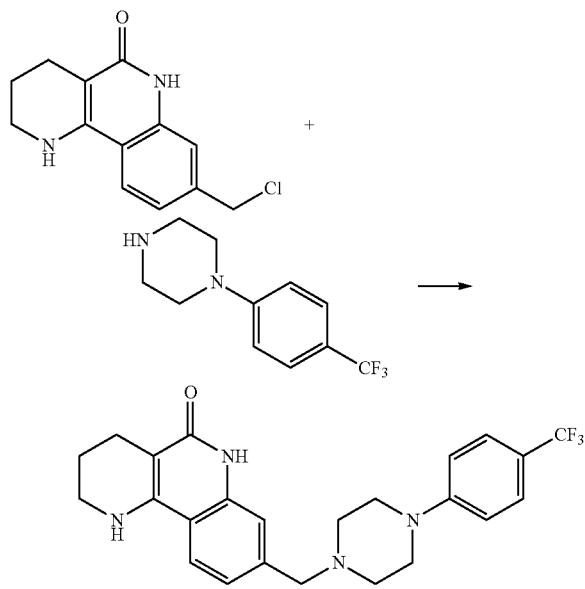

Using 8-(chloromethyl)-1,2,3,4-tetrahydrobenzo[h][1,6]naphthyridin-5-(6H)-one (50 mg, 0.20 mmol) prepared in step 2, the title compound (41 mg, yield: 46%, yellow solid) was obtained in the same manner as step 7 of Example 1.

¹H NMR (400 MHz, CD₃OD); δ 7.73 (d, J=8.4 Hz, 1H), 7.46 (d, J=8.8 Hz, 2H), 7.30 (s, 1H), 7.23 (d, J=8.4 Hz, 1H), 7.03 (d, J=8.8 Hz, 2H), 3.65 (s, 2H), 3.45-3.41 (m, 2H), 3.33-3.30 (m, 4H), 2.66-2.60 (m, 6H), 1.95-1.89 (m, 2H)

Step 4: Synthesis of 8-({4-[4-(trifluoromethyl)phenyl]piperazin-1-yl}methyl)-1,2,3,4-tetrahydrobenzo[h][1,2]naphthyridin-5(6H)-one dihydrochloride

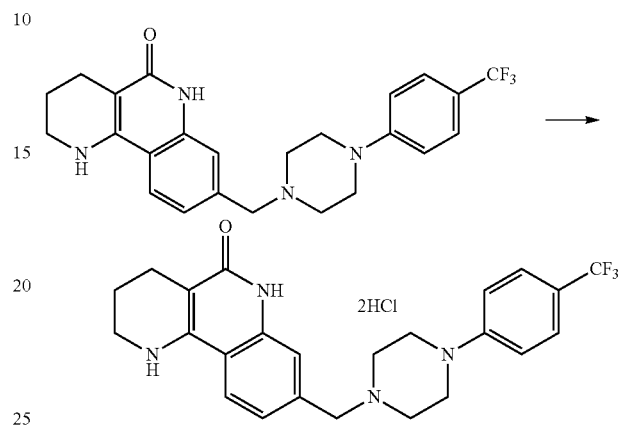

Using 8-({4-[4-(trifluoromethyl)phenyl]piperazin-1-yl}methyl)-1,2,3,4-tetrahydrobenzo[h][1,2]naphthyridin-5(6H)-one (40 mg, 0.09 mmol) prepared in step 3, the title compound (20 mg, yield: 43%, yellow solid) was obtained in the same manner as step 9 of Example 1.

¹H NMR (400 MHz, DMSO-d6); δ 11.81 (s, 1H), 11.70-11.50 (br, 1H), 8.05 (d, J=8.8 Hz, 1H), 7.58 (d, J=8.0 Hz, 1H), 7.52 (d, J=8.8 Hz, 2H), 7.47 (s, 1H), 7.08 (d, J=8.4 Hz, 2H), 4.41 (sS, 2H), 3.94 (br, 4H), 3.33-3.30 (m, 6H), 2.52-2.46 (m, 2H), 1.80-1.78 (m, 2H).

Compounds of Examples 116 to 165 were prepared in the same manner as described in Examples 115, except that substituents were changed as shown in Table 2 below.

TABLE 2

| Example | Structure | NMR |
|---|---|---|
| 116 | [structure with ethoxy group and pyridine-CN piperazine, 2HCl] | ¹H NMR (400 MHz, DMSO-d₆); δ 11.14 (s, 1H), 11.06 (br, 1H), 8.62 (s, 1H), 7.98 (d, J = 9.2 Hz, 1H), 7.45 (br, 1H), 7.05-7.03 (m, 2H), 6.85 (s, 1H), 4.57-4.54 (m, 2H), 4.31-4.26 (m, 6H), 3.45-3.34 (m, 4H), 3.09 (br, 2H), 2.45 (br, 2H), 1.76 (br, 2H), 1.45 (t, J = 6.8 Hz, 3H) |
| 117 | [structure with 2-Cl-4-CF₃-phenyl piperazine, 2HCl] | ¹H NMR (400 MHz, DMSO-d₆); δ 11.15 (s, 1H), 11.00-10.90 (br, 1H), 7.91 (d, J = 8.0 Hz, 1H), 7.84 (s, 1H), 7.70 (d, J = 8.8 Hz, 1H), 7.41 (d, J = 7.6 Hz, 1H), 7.38 (s, 1H), 7.36-7.34 (m, 1H), 4.46 (s, 2H), 3.56 (d, J = 11.6 Hz, 2H), 3.44-3.42 (m, 2H), 3.36-3.18 (m, 8H), 1.85-1.75 (m, 2H) |

TABLE 2-continued

| Example | Structure | NMR |
|---|---|---|
| 118 | [structure with 2HCl, Cl, CF3 substituents] | $^1$H NMR (400 MHz, DMSO-d$_6$); δ 11.17 (s, 1H), 11.10-10.90 (br, 1H), 7.91 (d, J = 8.0 Hz, 1H), 7.64 (d, J = 9.2 Hz, 1H), 7.40 (d, J = 8.0 Hz, 1H), 7.30 (s, 1H), 7.25 (s, 1H), 7.03 (d, J = 8.0 Hz, 1H), 4.39 (s, 2H), 4.08 (d, J = 13.2 Hz, 2H), 3.23 (br, 8H), 3.20-3.10 (m, 2H), 1.81-1.80 (m, 2H) |
| 119 | [structure with 2HCl, F, NO2 substituents] | $^1$H NMR (400 MHz, DMSO-d$_6$); δ 11.24 (s, 1H), 11.10-10.90 (m, 1H), 7.91 (d, J = 8.0 Hz, 1H), 7.58 (d, J = 8.4 Hz, 1H), 7.48-7.36 (m, 1H), 7.30 (s, 1H), 7.01 (s, 1H), 6.91 (d, J = 8.8 Hz, 1H), 4.40-4.39 (m, 2H), 4.08-4.01 (m, 2H), 3.80-3.50 (m, 2H), 3.32-3.25 (m, 4H), 3.16-3.11 (m, 2H), 2.50-2.47 (m, 2H), 2.40 (s, 3H), 1.85-1.75 (m, 2H) |
| 120 | [structure with 2HCl, pyridyl-Cl substituent] | $^1$H NMR (400 MHz, DMSO-d$_6$); δ 11.26 (s, 1H), 10.88 (br, 1H), 8.18 (s, 1H), 7.92 (d, J = 8.4 Hz, 1H), 7.73-7.70 (m, 1H), 7.40 (d, J = 8.0 Hz, 1H), 7.31 (s, 1H), 6.98 (d, J = 13.2 Hz, 1H), 4.90-4.33 (m, 6H), 3.33-3.24 (m, 6H), 3.09 (d, J = 9.6 Hz, 2H), 1.90-1.80 (m, 2H) |
| 121 | [structure with 2HCl, pyridyl-CF3 substituent] | $^1$H NMR (400 MHz, DMSO-d$_6$); δ 11.26 (s, 1H), 11.04 (br, 1H), 8.48 (s, 1H), 7.92 (d, J = 7.6 Hz, 2H), 7.41 (d, J = 7.6 Hz, 1H), 7.31 (s, 1H), 7.07 (d, J = 9.2 Hz, 1H), 4.53 (d, J = 13.2 Hz, 2H), 4.39 (s, 2H), 3.38-3.35 (m, 8H), 3.20-3.05 (m, 2H), 1.90-1.75 (m, 2H) |
| 122 | [structure with 2HCl, pyridyl-SO2Me substituent] | $^1$H NMR (400 MHz, DMSO-d$_6$); δ 11.21 (br, 1H), 11.06 (br, 1H), 8.57 (s, 1H), 8.01 (d, J = 6.8 Hz, 1H), 7.92 (d, J = 8.0 Hz, 1H), 7.40 (d, J = 8.0 Hz, 1H), 7.31 (s, 1H), 7.08 (d, J = 9.2 Hz, 1H), 4.62-4.50 (m, 2H), 4.45-4.30 (m, 2H), 3.50-3.30 (m, 6H), 3.25-3.00 (m, 5H), 2.70-2.30 (m, 2H), 1.85-1.70 (m, 2H) |
| 123 | [structure with 2HCl, pyridyl-CN substituent] | $^1$H NMR (400 MHz, DMSO-d$_6$); δ 12.02 (br, 1H), 11.89 (br, 1H), 8.47 (s, 1H), 8.13 (d, J = 8.4 Hz, 1H), 7.84 (d, J = 8.8 Hz, 1H), 7.66 (d, J = 8.4 Hz, 1H), 7.53 (s, 1H), 7.45 (d, J = 8.8 Hz, 1H), 4.45 (s, 21H), 4.18-3.32 (m, 10H), 2.56 (br, 2H), 1.82 (br, 2H) |
| 124 | [structure with 2HCl, pyridyl-CN substituent] | $^1$H NMR (400 MHz, DMSO-d$_6$); δ 11.27 (br, 1H), 10.94 (br, 1H), 8.35 (d, J = 5.2 Hz, 1H), 7.92 (d, J = 8.4 Hz, 1H), 7.45 (s, 1H), 7.45-7.35 (m, 1H), 7.31 (s, 1H), 7.09 (d, J = 5.2 Hz, 1H), 4.50-4.40 (m, 2H), 4.40-4.35 (m, 2H), 3.40-3.25 (m, 6H), 3.20-3.00 (m, 2H), 1.85-1.70 (m, 2H) |

TABLE 2-continued

| Example | Structure | NMR |
| --- | --- | --- |
| 125 | 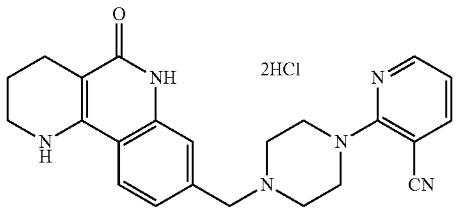 | $^1$H NMR (400 MHz, DMSO-d$_6$); δ 11.63 (s, 2H), 8.46-8.44 (m, 1H), 8.16-8.13 (m, 1H), 8.01 (d, J = 8.4 Hz, 1H), 7.56 (d, J = 8.0 Hz, 1H), 7.44 (s, 1H), 7.06-7.03 (m, 1H), 4.42 (s, 2H), 4.21 (d, J = 13.2 Hz, 2H), 3.54 (t, J = 12.4 Hz, 2H), 3.40-3.31 (m, 4H), 3.3-3.1 (m, 2H), 2.48-2.47 (m, 2H), 1.81-1.80 (m, 2H) |
| 126 | 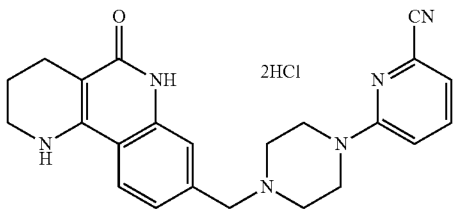 [SMILES: N#Cc1cccc(N2CCN(Cc3ccc4c5c(c(=O)[nH]c4c3)CCCN5)CC2)n1] | $^1$H NMR (400 MHz, DMSO-d$_6$); δ 11.20 (s, 1H), 11.09 (br s, 1H), 7.91 (d, J = 7.5 Hz, 1H), 7.78-7.67 (m, 1H), 7.42 (d, J = 7.5 Hz, 1H), 7.30-7.25 (m, 2H), 4.42-4.36 (m, 4H), 3.37-3.29 (m, 8H), 3.17-3.09 (m, 2H), 1.78 (s, 2H) |
| 127 | 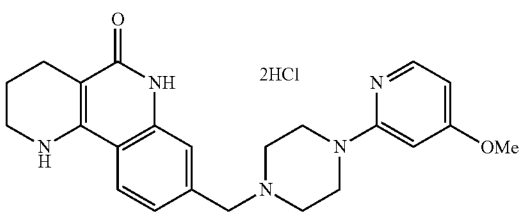 [SMILES: COc1ccnc(N2CCN(Cc3ccc4c5c(c(=O)[nH]c4c3)CCCN5)CC2)c1] | $^1$H NMR (400 MHz, DMSO-d$_6$); δ 11.74 (br, 1H), 11.34 (br, 1H), 7.99 (d, J = 6.8 Hz, 1H), 7.96 (d, J = 8.8 Hz, 1H), 7.49 (d, J = 7.6 Hz, 1H), 7.33 (s, 1H), 6.76 (s, 1H), 6.72 (d, J = 6.4 Hz, 1H), 4.55-4.42 (m, 2H), 4.40 (s, 2H), 3.97 (s, 3H), 3.75-3.55 (m, 2H), 3.45-3.10 (m, 6H), 2.50-2.40 (m, 2H), 1.75-1.85 (m, 2H) |
| 128 | 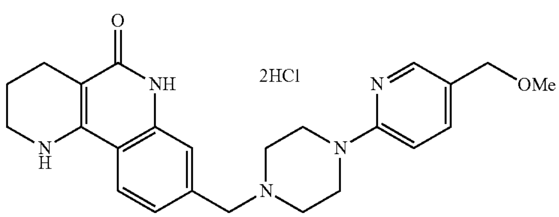 [SMILES: COCc1ccc(N2CCN(Cc3ccc4c5c(c(=O)[nH]c4c3)CCCN5)CC2)nc1] | $^1$H NMR (400 MHz, CD$_3$OD); δ 8.09-8.06 (m 2H), 8.00 (s, 1H), 7.76 (s, 1H), 7.60 (d, J = 8.0 Hz, 1H), 7.42 (d, J = 9.6 Hz, 1H), 4.57 (s, 2H), 4.41 (s, 2H), 3.58-3.51 (m, 6H), 3.39 (s, 3H), 3.28-3.27 (m, 4H), 2.68-2.67 (m, 2H), 1.99-1.95 (m, 2H) |
| 129 | 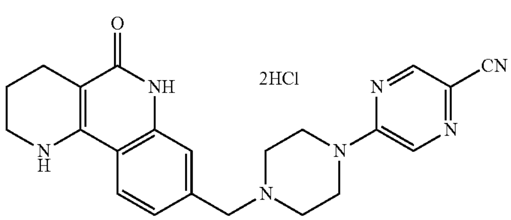 [SMILES: N#Cc1cnc(N2CCN(Cc3ccc4c5c(c(=O)[nH]c4c3)CCCN5)CC2)cn1] | $^1$H NMR (400 MHz, DMSO-d$_6$); δ 11.15 (s, 1H), 10.98 (br s, 1H), 8.65 (s, 2H), 8.50 (s, 1H), 7.90 (d, J = 8.2 Hz, 1H), 7.35 (d, J = 8.2 Hz, 1H), 7.26 (s, 1H), 4.63-4.60 (m, 2H), 4.35 (s, 2H), 3.49-3.31 (m, 8H), 3.15 (s, 3H), 1.78 (s, 2H) |
| 130 | 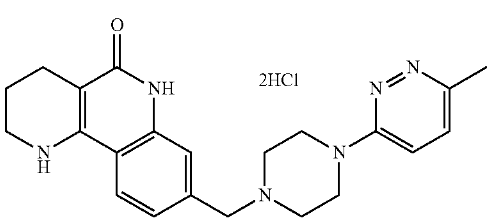 [SMILES: Cc1ccc(N2CCN(Cc3ccc4c5c(c(=O)[nH]c4c3)CCCN5)CC2)nn1] | $^1$H NMR (400 MHz, DMSO-d$_6$); δ 11.18 (s, 1H), 10.04 (br s, 1H), 8.03-8.01 (m, 2H), 7.92 (d, J = 8.2 Hz, 1H), 7.47 (d, J = 7.9 Hz, 1H), 7.31 (s, 1H), 4.36 (s, 2H), 3.54-3.25 (m, 10H), 2.61 (s, 3H), 1.77 (s, 2H) |
| 131 | 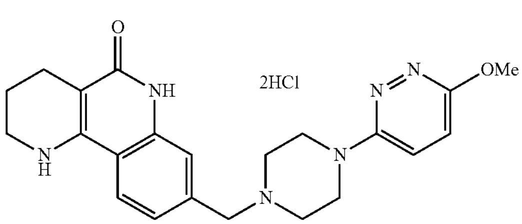 [SMILES: COc1ccc(N2CCN(Cc3ccc4c5c(c(=O)[nH]c4c3)CCCN5)CC2)nn1] | $^1$H NMR (400 MHz, DMSO-d$_6$); δ 11.14 (s, 1H), 9.78 (br, 1H), 7.90-7.88 (m, 1H), 7.64 (d, J = 9.4 Hz, 1H), 7.47 (d, J = 9.4 Hz, 1H), 7.39 (s, 1H), 7.29 (s, 1H), 4.44-4.36 (m, 4H), 3.54-3.25 (m, 8H), 1.78 (s, 2H) |

TABLE 2-continued

| Example | Structure | NMR |
|---|---|---|
| 132 | (structure) | ¹H NMR (400 MHz, DMSO-d₆); δ 11.51 (s, 1H), 11.37 (s, 1H), 8.02-7.45 (m, 4H), 7.36 (s, 1H), 4.65 (d, J = 13.6 Hz, 2H), 4.39 (s, 2H), 3.63-3.12 (m, 8H), 2.46 (d, J = 6.0 Hz, 2H), 2.52-2.47 (m, 2H), 1.86-1.78 (m, 2H) |
| 133 | (structure) | ¹H NMR (400 MHz, DMSO-d₆); δ 11.15 (s, 1H), 10.94 (br, 1H), 8.68 (s, 1H) 8.39 (s, 1H), 7.90 (d, J = 8.4 Hz, 1H), 7.38 (d, J = 8.4 Hz, 1H), 7.31 (s, 1H), 4.40 (s, 2H), 4.19 (d, J = 13.2 Hz, 2H), 3.45-3.39 (m, 4H), 3.35-3.30 (m, 2H), 3.22-3.15 (m, 4H), 1.85-1.75 (m, 2H) |
| 134 | (structure) | ¹H NMR (400 MHz, DMSO-d₆); δ 11.56 (br, 1H), 11.46 (br, 1H), 8.56 (s, 1H), 7.98 (d, J = 8.8 Hz, 1H), 7.51 (d, J = 8.0 Hz, 1H), 7.39 (s, 1H), 7.29 (s, 1H), 4.50-4.35 (m, 2H), 4.30-3.80 (m, 4H), 3.70-3.60 (m, 2H), 3.45-3.30 (m, 4H), 3.30-3.20 (m, 2H), 1.90-1.80 (m, 2H) |
| 135 | (structure) | ¹H NMR (400 MHz, DMSO-d₆); δ 11.21 (br, 1H), 11.06 (br, 1H), 8.57 (s, 1H), 8.01 (d, J = 6.8 Hz, 1H), 7.92 (d, J = 8.0 Hz, 1H), 7.40 (d, J = 8.0 Hz, 1H), 7.31 (s, 1H), 7.08 (d, J = 9.2 Hz, 1H), 4.62-4.50 (m, 2H), 4.45-4.30 (m, 2H), 3.50-3.30 (m, 6H), 3.25-3.00 (m, 5H), 2.70-2.30 (m, 2H), 1.85-1.70 (m, 2H) |
| 136 | (structure) | 1H NMR (400 MHz, DMSO-d₆); δ 11.12 (s, 1H), 10.80 (br, 1H), 8.46 (s, 1H), 7.89 (d, J = 8.8 Hz, 1H), 7.62 (s, 1H), 7.35 (d, J = 8.8 Hz, 1H), 7.27 (s, 1H), 4.44-4.36 (m, 4H), 3.38-3.31 (m, 6H), 3.12-3.09 (m, 2H), 2.47-2.45 (m, 2H), 1.80 (br, 2H) |
| 137 | (structure) | ¹H NMR (400 MHz, DMSO-d₆); δ 11.52 (br, 2H), 8.37 (s, 1H), 7.99 (d, J = 8.0 Hz, 1H), 7.51 (d, J = 8.4 Hz, 1H), 7.37 (s, 1H), 6.56 (s, 1H), 4.65-4.50 (m, 2H), 4.38 (s, 2H), 3.94 (s, 3H), 3.50-3.30 (m, 6H), 3.10-3.00 (m, 2H), 2.55-2.45 (m, 2H), 1.80-1.70 (m, 2H) |
| 138 | (structure) | ¹H NMR (400 MHz, DMSO-d₆); δ 11.53 (br, 1H), 11.44 (br, 1H), 8.10 (s, 1H), 7.98 (d, J = 8.0 Hz, 1H), 7.51 (d, J = 8.4 Hz, 1H), 7.37 (s, 1H), 6.60 (s, 1H), 4.50-4.35 (m, 6H), 3.91 (s, 3H), 3.40-3.25 (m, 6H), 3.15-3.00 (m, 2H), 1.85-1.70 (m, 2H) |

TABLE 2-continued

| Example | Structure | NMR |
|---|---|---|
| 139 | 2HCl | $^1$H NMR (400 MHz, DMSO-d$_6$); δ 11.29 (s, 1H), 11.28 (br, 1H), 8.11 (s, 1H), 7.93 (d, J = 8.4 Hz, 1H), 7.43 (d, J = 8.4 Hz, 1H), 7.31 (s, 1H), 4.40 (s, 2H), 4.09-3.16 (m, 12H), 2.51-2.46 (m, 2H), 1.83-1.76 (m, 2H) |
| 140 | 2HCl | $^1$H NMR (400 MHz, DMSO-d$_6$); δ 11.18 (s, 1H), 10.93 (br, 1H), 7.90 (d, J = 8.4 Hz, 1H), 7.69 (d, J = 4.4 Hz, 1H), 7.37 (d, J = 8.4 Hz, 1H), 7.29 (s, 1H), 7.14 (br, 1H), 6.37 (d, J = 4.4 Hz, 1H), 4.41 (s, 2H), 3.84-3.16 (m, 10H), 2.50-1.76 (m, 4H) |
| 141 | 2HCl | $^1$H NMR (400 MHz, DMSO-d$_6$); δ 11.76 (br, 2H), 8.05 (d, J = 8.0 Hz, 1H), 7.91 (s, 1H), 7.58 (d, J = 8.0 Hz, 1H), 7.45 (s, 1H), 4.43 (s, 2H), 4.26-3.17 (m, 12H), 2.59-1.77 (m, 4H), 1.25 (t, J = 7.2 Hz, 3H) |
| 142 | 2HCl | $^1$H NMR (400 MHz, DMSO-d$_6$); δ 11.77 (br, 1H), 11.51 (s, 1H), 8.10 (s, 1H), 8.00 (d, J = 8.4 Hz, 1H), 7.53 (d, J = 8.4 Hz, 1H), 7.39 (s, 1H), 4.50 (s, 2H), 4.18-3.17 (m, 10H), 2.56-1.77 (m, 4H) |
| 143 | 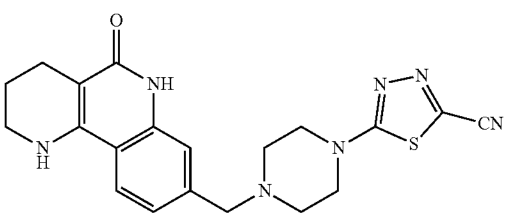 [SMILES: N#Cc1nnc(N2CCN(Cc3ccc4c5c(c(=O)[nH]c4c3)CCCN5)CC2)s1] | $^1$H NMR (400 MHz, DMSO-d$_6$); δ 8.71 (s, 1H), 7.74 (d, J = 8.4 Hz, 1H), 7.32 (s, 1H), 7.24 (d, J = 7.6 Hz, 1H), 3.68 (s, 2H), 3.62-3.54 (m, 4H), 3.48-3.42 (m, 2H), 2.68-2.58 (m, 6H), 2.0-1.90 (m, 2H) |
| 144 | 2HCl | $^1$H NMR (400 MHz, DMSO-d$_6$); δ 11.79 (br, 1H), 11.48 (s, 1H), 8.10 (s, 1H), 8.02 (d, J = 8.5 Hz, 1H), 7.51 (d, J = 8.3 Hz, 1H), 7.39 (s, 1H), 4.50 (s, 2H), 4.16-3.14 (m, 10H), 2.57-1.79 (m, 4H) |
| 145 | 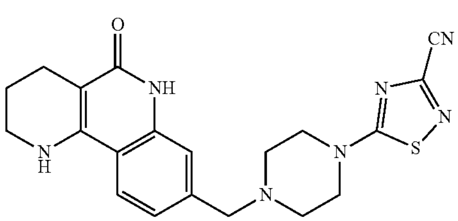 [SMILES: N#Cc1nsc(N2CCN(Cc3ccc4c5c(c(=O)[nH]c4c3)CCCN5)CC2)n1] | $^1$H NMR (400 MHz, DMSO-d$_6$); δ 10.89 (br, 1H), 7.71 (d, J = 8.0 Hz, 1H), 7.14 (s, 1H), 7.02 (d, J = 8.0 Hz, 1H), 6.86 (br, 1H), 3.54 (s, 2H), 3.59-3.40 (m, 6H), 3.40-3.20 (m, 4H), 3.20-3.10 (m, 1H), 2.60-2.38 (m, 2H), 1.80-1.70 (m, 2H) |

TABLE 2-continued

| Example | Structure | NMR |
|---|---|---|
| 146 | 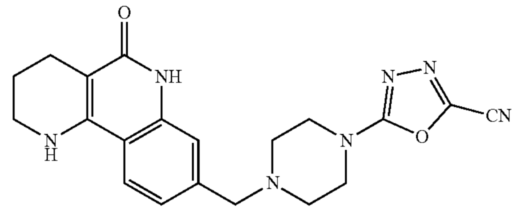 [SMILES: N#Cc1nnc(N2CCN(Cc3ccc4c5c(c(=O)[nH]c4c3)CCCN5)CC2)o1] | $^1$H NMR (400 MHz, CD$_3$OD); δ 7.71 (d, J = 8.4 Hz, 1H), 7.29 (s, 1H), 7.21 (d, J = 8.4 Hz, 1H), 3.94 (s, 2H), 3.66-3.62 (m, 4H), 3.44-3.40 (m, 2H), 2.61 (t, J = 5.2 Hz, 4H), 1.96-1.91 (m, 2H), 1.34-1.32 (m, 2H) |
| 147 | 2HCl | $^1$H NMR (400 MHz, DMSO-d$_6$); δ 11.41 (br, 1H), 11.40 (s, 1H), 9.67 (s, 1H), 7.98-7.00 (m, 6H), 4.44-4.18 (m, 4H), 3.70-3.20 (m, 8H), 2.56-1.77 (m, 4H) |
| 148 | 2HCl | $^1$H NMR (400 MHz, CD$_3$OD); δ 7.76-7.73 (m, 1H), 7.56-7.54 (m, 1H), 7.32 (s, 1H), 7.26-7.23 (m, 1H), 7.17-7.12 (m, 1H), 6.96 (s, 1H), 3.67 (s, 2H), 3.48-3.46 (m, 4H), 3.13 (s, 2H), 2.67-2.62 (m, 4H), 2.06-2.02 (s, 2H), 1.92 (s, 2H), 1.47 (s, 3H) |
| 149 | 2HCl | $^1$H NMR (400 MHz, DMSO-d$_6$); δ 11.19 (s, 1H), 10.62 (br s, 1H), 7.91 (d, J = 8.2 Hz, 1H), 7.59 (d, J = 9.0 Hz, 1H), 7.47-7.38 (m, 1H), 7.31 (s, 1H), 7.26 (s, 1H), 4.42 (s, 2H), 3.40-3.11 (m, 12H), 1.78 (s, 2H) |
| 150 | 2HCl | $^1$H NMR (400 MHz, DMSO-d$_6$); δ 11.24 (s, 1H), 1.91 (s, 1H), 10.62 (br, 1H), 7.93 (d, J = 8.8 Hz, 1H), 7.43-7.40 (m, 2H), 7.35 (s, 1H), 7.20 (s, 1H), 6.91 (s, 1H), 6.81 (d, J = 8.8 Hz, 1H), 6.31 (s, 1H), 4.44 (s, 2H), 3.70 (d, J = 12.0 Hz, 2H), 3.43-3.40 (m, 2H), 3.33-3.20 (m, 8H), 3.12-3.0 (m, 2H), 1.85-1.75 (m, 2H) |
| 151 | 2HCl | $^1$H NMR (400 MHz, DMSO-d$_6$); δ 11.37 (s, 1H), 10.86 (br, 1H), 7.99-7.44 (m, 4H), 7.38 (s, 1H), 7.22-7.17 (m, 2H), 4.44 (s, 2H), 3.44-3.05 (m, 10H), 2.50-1.77 (m, 4H) |
| 152 | 2HCl | $^1$H NMR (400 MHz, DMSO-d$_6$); δ 11.18-11.14 (m, 1H), 7.90 (s, 1H), 7.61 (d, J = 8.8 Hz, 1H), 7.33 (s, 2H), 6.93 (d, J = 9.2 Hz, 1H), 6.85 (s, 1H), 4.51 (s, 2H), 3.86 (d, J = 12.8 Hz, 1H), 3.40-3.33 (m, 4H), 3.26-3.24 (m, 4H), 3.17-3.12 (m, 4H), 1.85-1.75 (m, 2H) |

TABLE 2-continued

| Example | Structure | NMR |
|---|---|---|
| 153 | 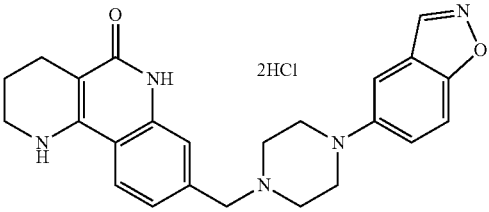 [SMILES: O=c1[nH]c2cc(CN3CCN(c4ccc5oncc5c4)CC3)ccc2c2c1CCCN2] | $^1$H NMR (400 MHz, DMSO-d$_6$); δ 11.14 (s, 1H), 10.56 (br s, 1H), 7.89 (d, J = 8.6 Hz, 1H), 7.35 (d, J = 7.8 Hz, 1H), 7.29 (s, 1H), 7.19-7.15 (m, 3H), 6.94 (d, J = 9.0 Hz, 1H), 4.47-4.42 (m, 4H), 3.65 (d, J = 12.5 Hz, 1H), 3.35-3.32 (m, 4H), 3.17-3.14 (m, 2H), 3.02-2.99 (m, 2H), 1.78 (s, 2H) |
| 154 | 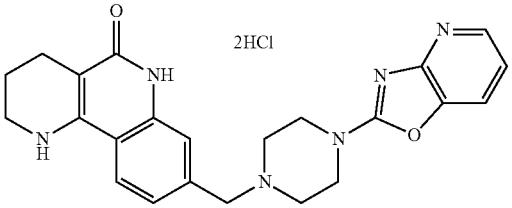 [SMILES: O=c1[nH]c2cc(CN3CCN(c4nc5ncccc5o4)CC3)ccc2c2c1CCCN2] | $^1$H NMR (400 MHz, DMSO-d$_6$); δ 11.77 (br, 1H), 11.34 (s, 1H), 9.61 (br, 1H), 8.21 (d, J = 5.6 Hz, 1H), 8.07-7.92 (m, 2H), 7.49 (d, J = 8.8 Hz, 1H), 7.34 (s, 1H), 7.23-7.12 (m, 1H), 4.50-4.20 (m, 4H), 4.00-3.92 (m, 2H), 3.92-3.60 (m, 2H), 3.50-3.15 (m, 6H), 1.90-1.87 (m, 2H) |
| 155 | 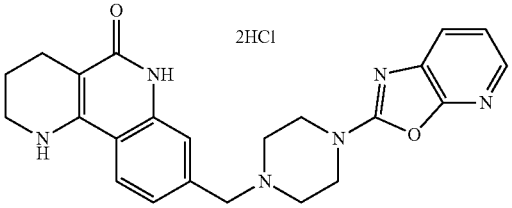 [SMILES: O=c1[nH]c2cc(CN3CCN(c4nc5cccnc5o4)CC3)ccc2c2c1CCCN2] | $^1$H NMR (400 MHz, DMSO-d$_6$); δ 10.72 (br, 1H), 7.88 (d, J = 5.2 Hz, 1H), 7.74 (d, J = 8.0 Hz, 1H), 7.63 (d, J = 8.0 Hz, 1H), 7.23-7.15 (m, 2H), 7.05 (d, J = 8.0 Hz, 1H), 6.87 (br, 1H), 3.70-3.60 (m, 4H), 3.56 (s, 2H), 3.40-3.20 (m, 2H), 2.55-2.40 (m, 6H), 1.85-1.70 (m, 2H) |
| 156 | 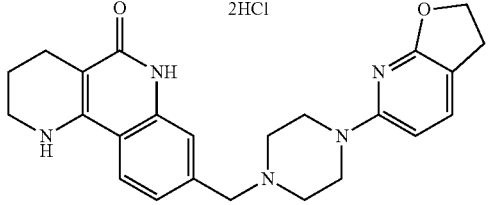 [SMILES: O=c1[nH]c2cc(CN3CCN(c4ccc5c(n4)OCC5)CC3)ccc2c2c1CCCN2] | $^1$H NMR (400 MHz, CD$_3$OD); δ 7.71 (d, J = 8.0 Hz, 1H), 7.37 (d, J = 8.4 Hz, 1H), 7.29 (s, 1H), 7.22 (d, J = 8.4 Hz, 1H), 6.20 (d, J = 8.4 Hz, 1H), 4.53 (t, J = 8.8 Hz, 2H), 3.64 (s, 2H), 3.43-3.40 (m, 6H), 3.11 (t, J = 8.4 Hz, 2H), 2.63-2.57 (m, 6H), 1.94-1.91 (m, 2H) |
| 157 | 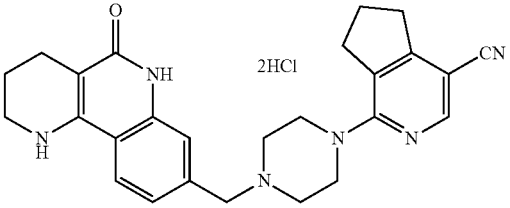 [SMILES: N#Cc1cnc(N2CCN(Cc3ccc4c5c(c(=O)[nH]c4c3)CCCN5)CC2)c2c1CCC2] | $^1$H NMR (400 MHz, DMSO-d$_6$); δ 11.40 (br, 1H), 11.28 (br, 1H), 8.42 (s, 1H), 7.95 (d, J = 8.4 Hz, 1H), 7.47 (d, J = 8.4 Hz, 1H), 7.35 (s, 1H), 4.50-4.20 (m, 6H), 3.50-3.40 (m, 2H), 3.40-3.30 (m, 2H), 3.20-3.05 (m, 2H), 3.00-2.90 (m, 4H), 2.55-2.45 (m, 2H), 2.10-2.00 (m, 2H), 1.85-1.75 (m, 2H) |
| 158 | 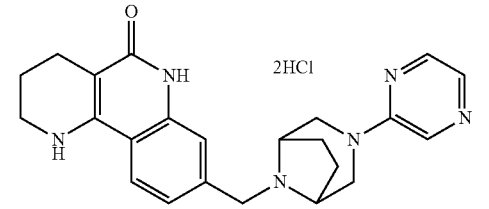 [SMILES: O=c1[nH]c2cc(CN3C4CCC3CN(c3cnccn3)C4)ccc2c2c1CCCN2] | $^1$H NMR (400 MHz, DMSO-d$_6$); δ 11.10 (s, 1H), 11.10-10.90 (br, 1H), 8.30 (s, 1H), 8.12 (s, 1H), 7.95-7.90 (m, 2H), 7.57-7.44 (m, 1H), 7.46-7.38 (m, 1H), 4.35-4.30 (m, 2H), 4.20-4.16 (m, 2H), 3.55-3.40 (m, 2H), 3.33 (br, 4H), 2.40-2.30 (m, 2H), 1.94-1.91 (m, 2H), 1.85-1.75 (m, 2H) |
| 159 | 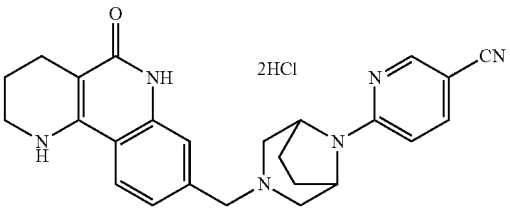 [SMILES: N#Cc1ccc(N2C3CCC2CN(Cc2ccc4c5c(c(=O)[nH]c4c2)CCCN5)C3)nc1] | $^1$H NMR (400 MHz, DMSO-d$_6$); δ 11.49 (s, 1H), 10.79 (br, 1H), 8.57 (s, 1H), 8.02-7.65 (m, 3H), 7.37 (s, 1H), 6.97 (d, J = 9.2 Hz, 1H), 4.82 (br, 2H), 4.30 (s, 2H), 3.35 (br, 2H), 3.32 (br, 4H), 2.51-1.76 (m, 8H) |

TABLE 2-continued

| Example | Structure | NMR |
|---|---|---|
| 160 | (structure: tetrahydro-pyrido-quinolinone with diazabicyclic-methyl linker to 6-chloropyridazine; 2HCl) | ¹H NMR (400 MHz, DMSO-d₆); δ 11.11 (s, 1H), 10.77 (br, 1H), 7.91 (d, J = 8.4 Hz, 1H), 7.64 (d, J = 10.0 Hz, 1H), 7.43-7.37 (m, 3H), 4.30 (d, J = 5.6 Hz, 2H), 4.20 (d, J = 14.0 Hz, 2H), 4.08-4.00 (m, 2H), 3.49-3.46 (m, 2H), 3.36-3.30 (m, 2H), 2.50-2.47 (m, 2H), 2.38-2.30 (m, 2H), 1.96-1.91 (m, 2H), 1.84-1.76 (m, 2H) |
| 161 | (structure: tetrahydro-pyrido-quinolinone with diazabicyclic-methyl linker to 3-fluoro-4-cyanophenyl; 2HCl) | ¹H NMR (400 MHz, DMSO-d₆); δ 11.12 (s, 1H), 10.10-9.90 (br, 1H), 7.87 (d, J = 8.0 Hz, 1H), 7.69-7.65 (m, 1H), 7.47 (d, J = 8.4 Hz, 1H), 7.38 (d, J = 8.0 Hz, 1H), 7.31 (s, 1H), 6.95-6.91 (m, 1H), 4.73 (s, 2H), 4.60-4.57 (m, 1H), 4.41 (s, 1H), 4.37-4.32 (m, 1H), 3.89-3.78 (m, 2H), 3.60-3.40 (m, 1H), 3.20-3.40 (m, 2H), 2.60-2.57 (m, 2H), 2.50-2.40 (m, 2H), 2.19-2.16 (m, 1H), 1.90-1.70 (m, 2H) |
| 162 | (structure: tetrahydro-pyrido-quinolinone with diazabicyclic-methyl linker to 2-fluoro-4-nitrophenyl; 2HCl) | ¹H NMR (400 MHz, CDCl₃); δ 11.14 (s, 1H), 10.16 (s, 1H), 8.00-8.04 (m, 1H), 7.92-7.95 (m, 1H), 7.87 (d, J = 8.0 Hz, 1H), 7.40 (d, J = 8.0 Hz, 1H), 7.32 (s, 1H), 7.06-6.94 (m, 1H), 4.85 (s, 1H), 4.53-4.61 (m, 1H), 4.45 (s, 1H), 4.34-4.39 (m, 1H), 3.95 (m. 1H), 3.87 (m, 1H), 3.62 (s, 2H), 3.31 (m, 2H), 2.60-2.63 (m, 1H), 2.44-2.45 (m, 2H), 2.20-2.22 (m, 1H), 1.78 (m, 2H) |
| 163 | (structure: fluoro-tetrahydro-pyrido-quinolinone with diazabicyclic-methyl linker to 6-chloropyridazine; 2HCl) | ¹H NMR (400 MHz, DMSO-d₆); δ 11.22 (s, 1H), 10.30-10.20 (br, 1H), 7.89 (d, J = 8.4 Hz, 1H), 7.60 (d, J = 9.6 Hz, 1H), 7.45-7.42 (m, 1H), 7.35 (s, 1H), 7.19 (d, J = 10.0 Hz, 1H), 4.97 (s, 1H), 4.60-4.56 (m, 1H), 4.78 (s, 1H), 4.40-4.35 (m, 1H), 4.30-4.10 (m, 2H), 3.96-3.93 (m, 1H), 3.65 (d, J = 10.8 Hz, 1H), 3.45-3.41 (m, 1H), 3.35-3.31 (m, 1H), 2.60 (d, J = 10.8 Hz, 1H), 2.20 (d, J = 11 Hz, 1H), 1.85-1.75 (m, 1H) |
| 164 | (structure: fluoro-tetrahydro-pyrido-quinolinone with diazabicyclic-methyl linker to pyrazine; 2HCl) | ¹H NMR (400 MHz, DMSO-d₆); δ 11.1136 (s, 1H), 10.03 (br, 1H), 8.07 (d, J = 13.2 Hz, 1H), 7.87-7.85 (m, 2H), 7.36 (d, J = 9.6 Hz, 1H), 7.31 (s, 1H), 4.95 (s, 1H), 4.61-4.56 (m, 1H), 4.45 (s, 2H), 4.38-4.30 (m, 1H), 3.84 (d, J = 12.4 Hz, 1H), 3.61 (d, J = 10.4 Hz, 1H), 3.37-3.35 (m, 1H), 3.32-3.22 (m, 2H), 2.48-2.44 (m, 2H), 1.85-1.70 (m, 2H) |
| 165 | (structure: tetrahydro-pyrido-quinolinone with methylpiperazine-methyl linker to 2-fluoro-4-cyanophenyl; 2HCl) | ¹H NMR (400 MHz, DMSO-d₆); δ 11.20 (s, 1H), 10.75-10.60 (m, 1H), 7.90 (d, J = 8.4 Hz, 1H), 7.68 (t, J = 8.4 Hz, 1H), 7.46 (d, J = 8.4 Hz, 1H), 7.31 (s, 1H), 7.01 (d, J = 14.4 Hz, 1H), 6.85 (d, J = 8.4 HZ, 1H), 4.60-4.40 (m, 2H), 4.40-4.25 (m, 1H), 4.20-3.80 (m, 2H), 3.42-3.38 (m, 2H), 3.35-3.30 (m, 2H), 3.30-3.10 (m, 2H), 2.50-2.40 (m, 2H), 1.85-1.75 (m, 2H), 1.23 (d, J = 6.4 Hz, 2H) |

Example 166: Synthesis of 10-fluoro-8-{[4-(2-fluoro-4-nitrophenyl)piperazin-1-yl]methyl}-1,2,3,4-tetrahydrobenzo[h][1,6]naphthyridin-5(6H)-one Dihydrochloride Step 1: Synthesis of ethyl 3-amino-5-fluorobenzoate

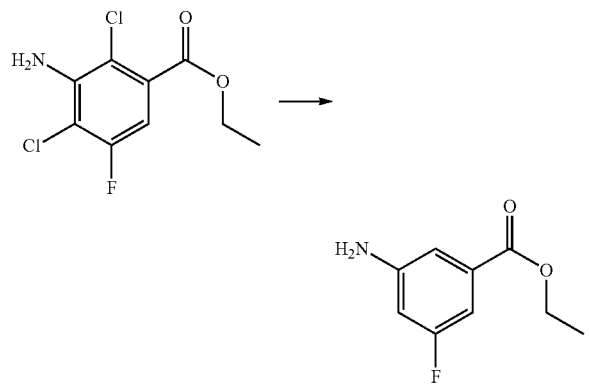

Ethyl 3-amino-2,4-dichloro-5-fluorobenzoate (5.0 g, 17.73 mmol) was dissolved in methanol (70 ml), and then 10%-palladium (500 mg) was added thereto under hydrogen gas, followed by stirring at room temperature for 1 day. After completion of the reaction, the solution was filtered through celite and concentrated under reduced pressure. The residue was purified by column chromatography (dichloromethane:methanol=10:1) to give the title compound (2266.6 mg, yield: 70%, white solid).

$^1$H NMR (400 MHz, CDCl$_3$); δ 7.13 (s, 1H), 7.09 (d, J=8.8 Hz, 1H), 6.56-6.53 (m, 1H), 4.35 (q, J=6.8 Hz, 2H), 1.38 (t, J=6.8 Hz, 3H).

Step 2: Synthesis of ethyl 3-(2-chloronicotinamido)-5-fluorobenzoate

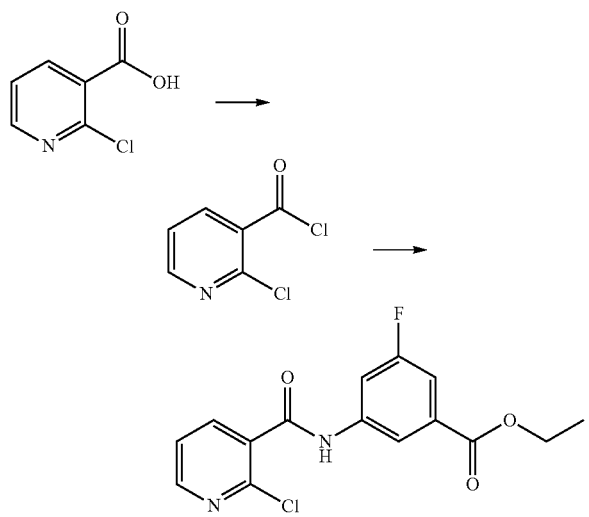

2-chloronicotinic acid (3 g, 18.68 mmol) was dissolved in dichloromethane and cooled to 0° C., and oxalyl chloride was added dropwise thereto. Next, a catalytic amount of N,N-dimethylformamide was added, and the mixture was stirred under reflux for 3 hours. After completion of the reaction, the solution was concentrated under reduced pressure. The obtained 2-chloropyridine-3-carbonyl chloride was dissolved in dichloromethane and cooled to 0° C., and the compound (2.63 g, 14.37 mmol) obtained in step 1 and trimethylamine were added thereto, followed by stirring at room temperature for 12 hours. Then, the reaction solution was concentrated under reduced pressure, and ethyl acetate was added to the residue obtained by concentration under recued pressure, followed by filtration under reduced pressure to remove the solid. After filtration, the obtained filtrate was concentrated under reduced pressure, and then purified by column chromatography (hexane:ethyl acetate=2:1) to give the title compound (4.20 g, yield: 91%, white solid).

$^1$H NMR (400 MHz, CDCl$_3$); δ 8.36-8.35 (m, 1H), 7.84-7.82 (m, 2H), 7.73-7.71 (m, 1H), 7.34-7.32 (m, 1H), 7.24-7.22 (m, 1H), 4.37 (q, J=7.2 Hz, 2H), 1.40-1.36 (m, 3H).

Step 3: Synthesis of ethyl 3-{2-chloro-N-(methoxymethyl)nicotinamido}-5-fluorobenzoate

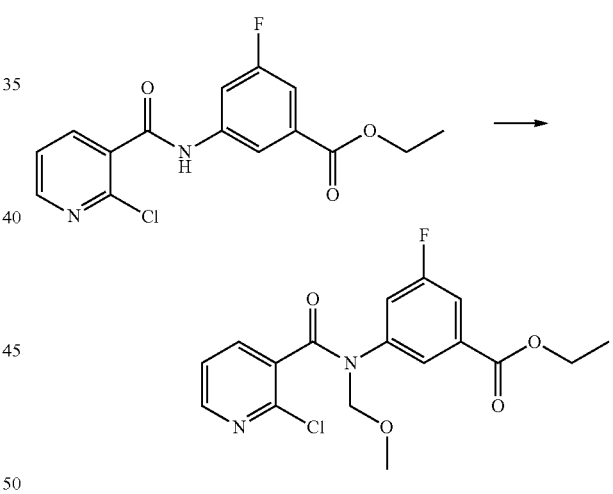

The compound (4.2 g, 13.01 mmol) prepared in step 2 was dissolved in tetrahydrofuran and cooled to 0° C., and then potassium t-butoxide (1844.3 mg, 15.61 mmol) was added thereto, followed by stirring for 30 minutes. Methoxymethyl chloride was added slowly dropwise to the reaction solution, followed by stirring for 1 hour. Then, water was slowly added to stop the reaction. Next, the reaction solution was extracted with dichloromethane, and the organic solvent layer was dried with anhydrous magnesium sulfate and concentrated under reduced pressure. The obtained residue was purified by column chromatography (hexane:ethyl acetate=10:1) to give the title compound (2.05 g, yield: 46%, yellow solid).

$^1$H NMR (400 MHz, CDCl$_3$); δ 8.28 (s, 1H), 7.62-7.56 (m, 3H), 7.19-7.15 (m, 2H), 5.28 (s, 2H), 4.35 (s, 2H), 3.59 (s, 3H), 1.37 (br, 3H).

Step 4: Synthesis of ethyl 10-fluoro-6-(methoxymethyl)-5-oxo-5,6-dihydrobenzo[h][1,6]naphthyridin-8-carboxylate

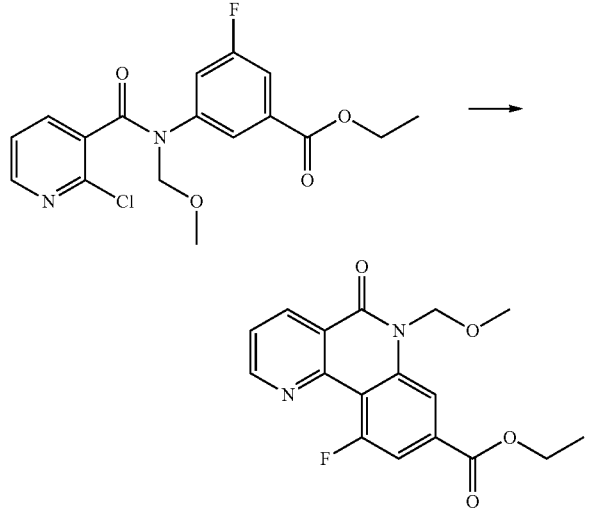 [SMILES: CCOC(=O)c1cc(F)cc(N(COC)C(=O)c2cccnc2Cl)c1 ; CCOC(=O)c1cc(F)c2c3ncccc3c(=O)n(COC)c2c1]

The compound (2.05 g, 5.93 mmol) prepared in step 3 was dissolved in N,N-dimethylformamide, and then palladium (II) acetate (399.4 mg, 1.78 mmol), bis-diphenylphosphinopropane (733.8 mg, 1.78 mmol), tributylphosphine (1.46 ml, 5.93 mmol) and potassium carbonate (1639.2 mg, 11.86 mmol) were sequentially added to the solution which was then stirred under reflux for 5 hours. Water was added to the reaction solution to stop the reaction, and the reaction solution was extracted with dichloromethane. The organic solvent layer was dried with anhydrous magnesium sulfate and concentrated under reduced pressure. Methanol was added to the residue obtained by concentration under reduced pressure, followed by filtration under reduced pressure. Dichloromethane was added to the filtrate, followed by filtration under reduced pressure to give the title compound (1145.3 mg, yield: 58%, yellow solid).

$^1$H NMR (400 MHz, CDCl$_3$); δ 9.17 (s, 1H), 8.83 (d, J=7.6 Hz, 1H), 8.16 (s, 1H), 7.77 (d, J=12.4 Hz, 1H), 7.63-7.60 (m, 1H), 5.87 (s, 2H), 4.46 (q, J=6.8 Hz, 2H), 3.50 (s, 3H), 1.45 (t, J=7.2 Hz, 3H).

Step 5: Synthesis of ethyl 10-fluoro-6-(methoxymethyl)-5-oxo-1,2,3,4,5,6-hexahydrobenzo[h][1,6]naphthyridin-8-carboxylate

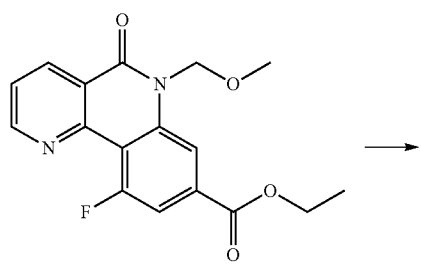

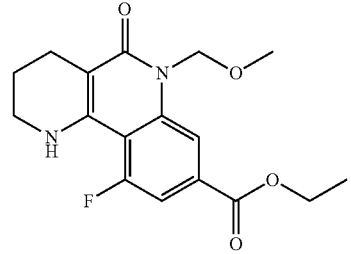

The compound (945.3 mg, 2.86 mmol) prepared in step 4 was dissolved in dichloromethane/methanol (15 ml), and then 10%-palladium (4 mg) was added thereto under hydrogen gas, followed by stirring at room temperature for 1 day. After completion of the reaction, the solution was filtered through celite and concentrated under reduced pressure. The residue was purified by column chromatography (hexane:ethyl acetate=1:1) to give the title compound (841.2 mg, yield: 90%, white solid).

$^1$H NMR (400 MHz, CDCl$_3$); δ 8.01 (s, 1H), 7.49 (d, J=14.8 Hz, 1H), 6.08 (d, J=19.6 Hz, 1H), 5.73 (s, 2H), 4.42 (q, J=6.8 Hz, 2H), 3.42 (s, 5H), 2.70 (t, J=6.0 Hz, 2H), 1.98-1.92 (m, 2H), 1.42 (t, J=6.8 Hz, 3H).

Step 6: Synthesis of 10-fluoro-8-(hydroxymethyl)-6-(methoxymethyl)-1,2,3,4-tetrahydrobenzo[h][1,6]naphthyridin-5(6H)-one

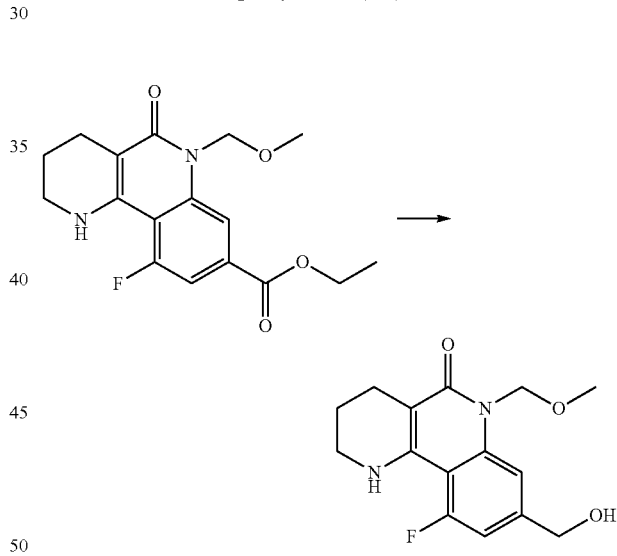

The compound (200 mg, 0.60 mmol) prepared in step 5 was dissolved in anhydrous tetrahydrofuran (10 ml), and then lithium aluminum hydride (34.1 mg, 0.90 mmol) was added slowly dropwise thereto at 0° C., followed by stirring at 0° C. for 2 hours. After completion of the reaction, 0° C. water (0.034 ml), 1.0N sodium hydroxide (0.034 ml) and 0° C. water (0.068 ml) were sequentially added, followed by stirring for 1 hour. Then, the reaction solution was filtered through celite and concentrated under reduced pressure. The residue was purified by column chromatography (dichloromethane:methanol=30:1) to give the title compound (130.2 mg, yield: 74%, off-white solid).

$^1$H NMR (400 MHz, CDCl$_3$); δ 7.28 (s, 1H), 6.91 (d, J=14.4 Hz, 1H), 6.06 (d, J=20.0 Hz, 1H), 5.68 (s, 2H), 4.76 (d, J=5.2 Hz, 2H), 3.41 (s, 5H), 2.68 (t, J=6.0 Hz, 2H), 1.94 (t, J=6.0 Hz, 2H).

Step 7: 8-(chloromethyl)-10-fluoro-6-(methoxymethyl)-1,2,3,4-tetrahydrobenzo[h][1,6]naphthyridin-5(6H)-one

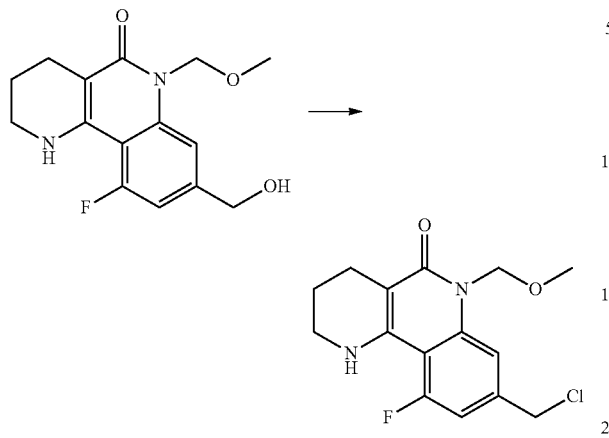

The compound (44.4 mg, 0.15 mmol) prepared in step 6 was added to anhydrous dichloromethane (7 ml), and then thionyl chloride (0.044 ml, 0.61 mmol) was added slowly dropwise thereto at 0° C. The mixture was stirred at room temperature for 4 hours. After completion of the reaction, dichloromethane and 0° C. water was added, and the organic layer was dried with anhydrous magnesium sulfate and concentrated under reduced pressure to give the title compound (33.4 mg, yield: 72%, white solid). The obtained compound was used without further purification in the next step.

Step 8: Synthesis of 10-fluoro-8-{[4-(2-fluoro-4-nitrophenyl)piperazin-1-yl]methyl}-6-(methoxymethyl)-1,2,3,4-tetrahydrobenzo[h][1,6]naphthyridin-5(6H)-one

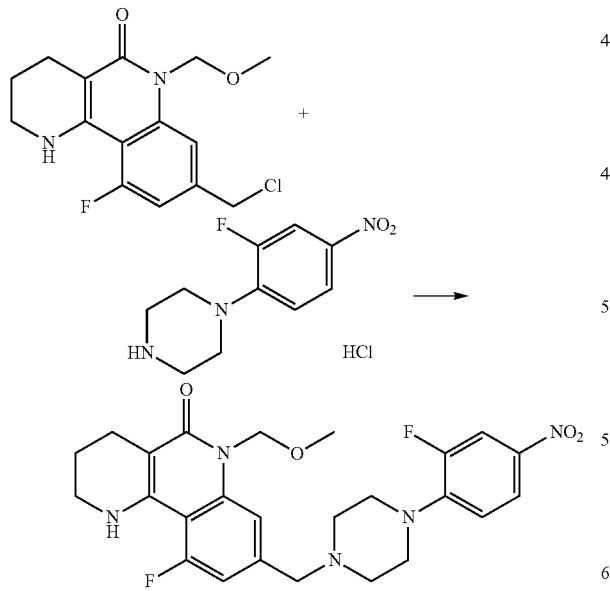

Using the compound (43 mg, 0.14 mmol) prepared in step 7, the title compound (46 mg, yield: 66%, white solid) was obtained in the same manner as step 7 of Example 1.

$^1$H NMR (400 MHz, CDCl$_3$); δ 7.99 (dd, J=2.0, 0.8 Hz, 1H), 7.97 (dd, J=2.8, 0.8 Hz, 1H), 7.30 (s, 1H), 6.97-6.88 (m, 2H), 6.07 (d, J=19.6 Hz, 1H), 5.70 (s, 2H), 3.63 (s, 2H), 3.48-3.40 (m, 5H), 3.40-3.30 (m, 4H), 2.72-2.63 (m, 6H), 2.00-1.90 (m, 2H).

Step 9: Synthesis of 10-fluoro-8-{[4-(2-fluoro-4-nitrophenyl)piperazin-1-yl]methyl}-1,2,3,4-tetrahydrobenzo[h][1,6]naphthyridin-5(6H)-one

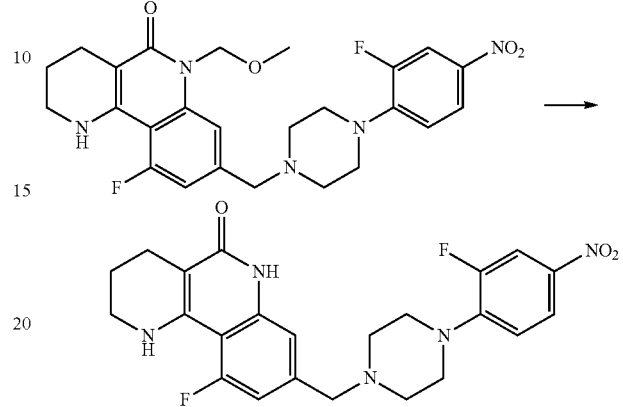

Using the compound (46 mg, 0.9 mmol) prepared in step 8, the title compound (34 mg, 74%, yellow solid) was obtained in the same manner as step 8 of Example 1.

$^1$H NMR (400 MHz, CDCl$_3$); δ 11.71 (br, 1H), 7.98 (dd, J=8.0, 2.4 Hz, 1H), 7.90 (dd, J=13.2, 2.8 Hz, 1H), 7.13 (s, 1H), 6.94-6.81 (m, 2H), 6.03 (d, J=17.6 Hz, 1H), 3.60 (s, 1H), 3.48-3.40 (m, 2H), 3.38-3.32 (m, 4H), 2.78-2.70 (m, 2H), 2.70-2.62 (m, 4H), 2.00-1.90 (m, 2H).

Step 10: Synthesis of 10-fluoro-8-{[4-(2-fluoro-4-nitrophenyl)piperazin-1-yl]methyl}-1,2,3,4-tetrahydrobenzo[h][1,6]naphthyridin-5(6H)-one dihydrochloride

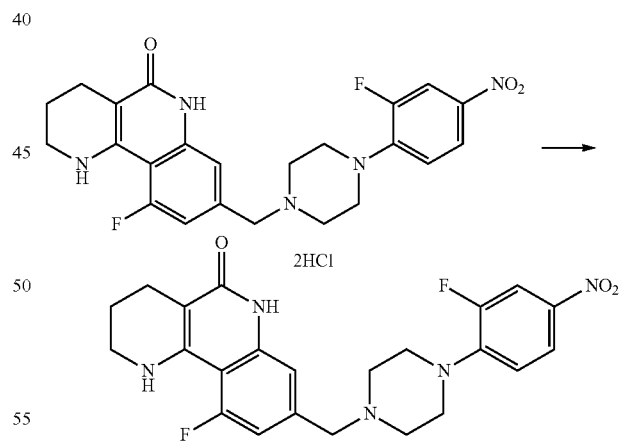

Using the compound (34 mg, 0.07 mmol) prepared in step 9, the title compound (40 mg, 99%, white solid) was obtained in the same manner as step 9 of Example 1.

$^1$H NMR (400 MHz, DMSO-d$_6$); δ 11.32 (br, 1H), 11.20 (br, 1H), 8.10-8.04 (m, 2H), 7.33-7.25 (m, 2H), 7.13 (s, 1H), 4.40 (br, 2H), 3.83-3.67 (m, 2H), 3.50-3.20 (m, 8H), 2.50-2.40 (m, 2H), 1.80-1.70 (m, 2H).

Compounds of Examples 167 to 177 were prepared in the same manner as described in Examples 166, except that substituents were changed as shown in Table 3 below.

TABLE 3

| Example | Structure | NMR |
|---|---|---|
| 167 | 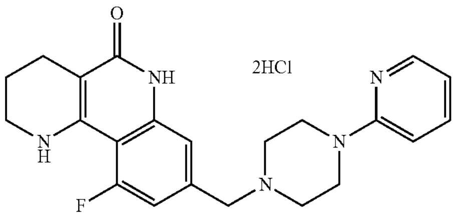 [SMILES: O=c1[nH]c2cc(CN3CCN(c4ccccn4)CC3)cc(F)c2c2c1CCCN2] | ¹H NMR (400 MHz, DMSO-d₆); δ 11.60-11.40 (br, 1H), 11.36 (s, 1H), 8.13 (d, J = 5.2 Hz, 1H), 8.00-7.70 (m, 1H), 7.37 (s, 1H), 7.21 (d, J = 14.0 Hz, 1H), 7.11 (s, 1H), 6.92 (t, J = 6.2 Hz, 1H), 4.37 (s, 2H), 4.0-3.65 (m, 4H), 3.65-3.55 (m, 2H), 2.60-2.40 (m, 4H), 1.76-1.70 (m, 2H) |
| 168 | 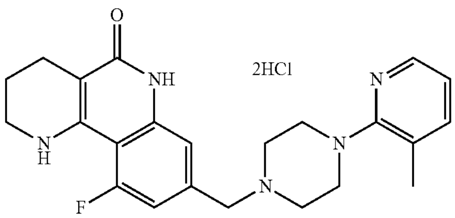 [SMILES: Cc1cccnc1N1CCN(Cc2cc(F)c3c4c(c(=O)[nH]c3c2)CCCN4)CC1] | ¹H NMR (400 MHz, DMSO-d₆); δ 11.35 (s, 1H), 11.10-10.98 (br, 1H), 8.14 (d, J = 4.0 Hz, 1H), 7.64 (d, J = 7.6 Hz, 1H), 7.34 (d, J = 14.0 Hz, 1H), 7.14 (s, 1H), 7.07-7.04 (m, 1H), 4.40 (s, 2H), 3.53 (br, 4H), 3.36-3.26 (m, 2H), 2.67-2.44 (m, 4H), 2.35-2.30 (m, 2H), 2.25 (S, 3H), 1.80-1.70 (m, 2H) |
| 169 | 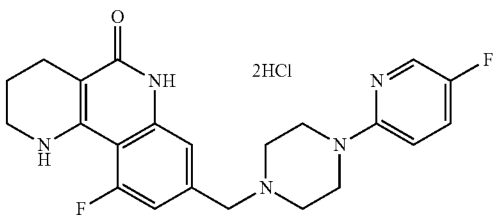 [SMILES: O=c1[nH]c2cc(CN3CCN(c4ccc(F)cn4)CC3)cc(F)c2c2c1CCCN2] | ¹H NMR (400 MHz, DMSO-d₆); δ 11.36 (s, 1H), 11.33 (br, 1H), 8.15 (s, 1H), 7.60 (t, J = 7.32 Hz, 1H), 7.38 (d, J = 14.16 Hz, 1H), 7.12 (s, 1H), 7.00 (d, J = 8.78 Hz, 1H), 4.35 (s, 2H), 4.29 (d, J = 13.18 Hz, 2H), 3.37-3.26 (m, 6H), 3.10 (s, 2H), 1.77 (s, 2H) |
| 170 | 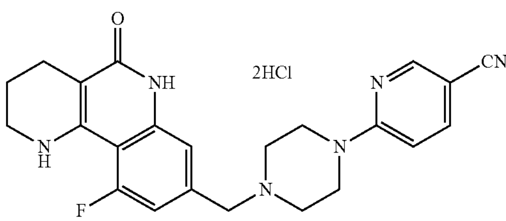 [SMILES: N#Cc1ccc(N2CCN(Cc3cc(F)c4c5c(c(=O)[nH]c4c3)CCCN5)CC2)nc1] | ¹H NMR (400 MHz, DMSO-d₆); δ 11.76 (br, 1H), 11.62 (br, 1H), 8.56 (d, J = 2.0 Hz, 1H), 7.98 (dd, J = 9.2 Hz, 2.4 Hz, 1H), 7.42 (d, J = 14.0 Hz, 1H), 7.13 (s, 1H), 7.04 (d, J = 8.8 Hz, 1H), 4.60-4.45 (m, 2H), 4.35 (br, 2H), 3.70-3.25 (m, 8H), 2.50-2.40 (m, 2H), 1.80-1.70 (m, 2H) |
| 171 | 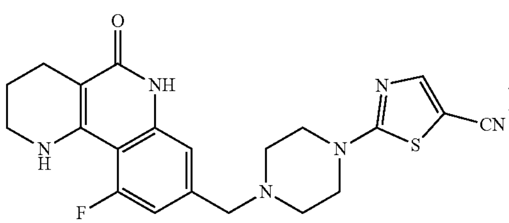 [SMILES: N#Cc1cnc(N2CCN(Cc3cc(F)c4c5c(c(=O)[nH]c4c3)CCCN5)CC2)s1] | ¹H NMR (400 MHz, DMSO-d₆); δ 10.96 (br, 1H), 8.02 (s, 1H), 7.01 (s, 1H), 6.83 (d, J = 14.8 Hz, 1H), 6.52 (d, J = 14.0 Hz, 1H), 3.60-3.50 (m, 8H), 3.50-3.20 (m, 4H), 2.50-2.40 (m, 2H), 1.80-1.70 (m, 2H) |
| 172 | 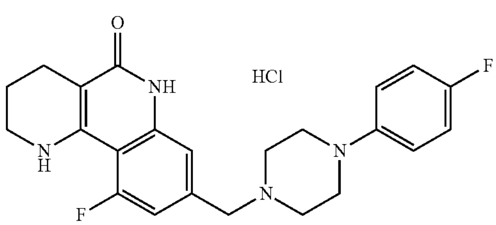 [SMILES: O=c1[nH]c2cc(CN3CCN(c4ccc(F)cc4)CC3)cc(F)c2c2c1CCCN2 ; Cl] | ¹H NMR (400 MHz, DMSO-d₆); δ 11.88 (s, 2H), 7.60 (d, J = 14.4 Hz, 1H), 7.29 (s, 1H), 7.09-7.07 (m, 2H), 7.01 (s, 2H), 4.43 (s, 2H), 3.80-3.65 (m, 2H), 3.40-3.30 (m, 4H), 3.21-3.15 (m, 4H), 2.55-2.45 (m, 2H), 1.85-1.75 (m, 2H) |
| 173 | 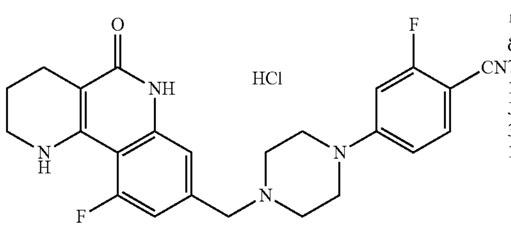 | ¹H NMR (400 MHz, DMSO-d₆); δ 12.0-11.8 (br, 1H), 11.4-11.2 (s, 1H), 7.69 (t, J = 8.2 Hz, 1H), 7.44-7.40 (m, 1H), 7.16-7.05 (m, 2H), 6.92 (d, J = 7.6 Hz, 1H), 4.42 (s, 2H), 3.71-3.12 (m, 6H), 2.50-2.20 (m, 6H), 1.80-1.70 (m, 2H) |

TABLE 3-continued

| Example | Structure | NMR |
|---|---|---|
| 174 | 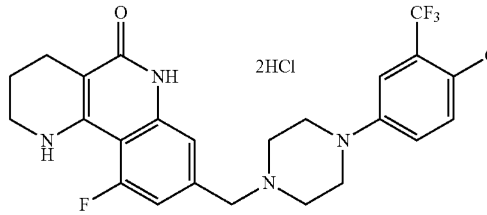 | $^1$H NMR (400 MHz, DMSO-$d_6$); δ 11.62 (br, 1H), 11.40 (s, 1H), 7.94 (d, J = 8.3 Hz, 1H), 7.41-7.36 (m, 2H), 7.31 (d, J = 7.8 Hz, 1H), 7.10 (s, 1H), 4.36 (s, 4H), 4.24 (d, J = 13.1 Hz, 2H), 3.50-3.16 (m, 8H), 1.76 (s, 2H) |
| 175 | 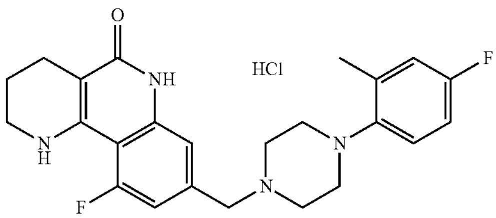 [SMILES: Cc1cc(F)ccc1N1CCN(Cc2cc(F)c3c4c(c(=O)[nH]c3c2)CCCN4)CC1 ; Cl] | $^1$H NMR (400 MHz, DMSO-$d_6$); δ 11.35 (s, 1H), 10.40-10.25 (br, 1H), 7.20 (d, J = 13.6 Hz, 1H), 7.13 (s, 1H), 7.09-7.05 (m, 1H), 7.02-6.98 (m, 1H), 6.65 (d, J = 12.8 Hz, 1H), 4.41 (d, J = 4.4 Hz, 1H), 3.16-3.11 (m, 2H), 3.02-2.96 (m, 2H), 2.70-2.60 (m 2H), 2.34-2.33 (m, 2H), 2.26 (S, 4H), 1.80-1.70 (m, 2H) |
| 176 | 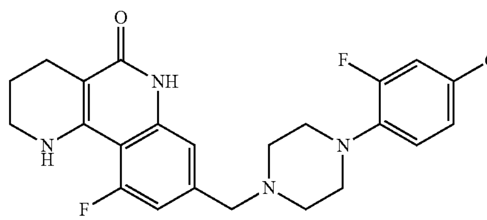 | $^1$H NMR (400 MHz, CD$_3$OD); δ 7.68 (s, 1H), 7.49-7.42 (m, 3H), 7.13 (t, J = 7.6 Hz, 1H), 4.53 (s, 2H), 3.73-3.70 (m, 2H), 3.51 (br, 4H), 3.35-3.24 (m, 4H), 2.75-2.60 (m, 2H), 2.00-1.85 (m, 2H) |
| 177 | 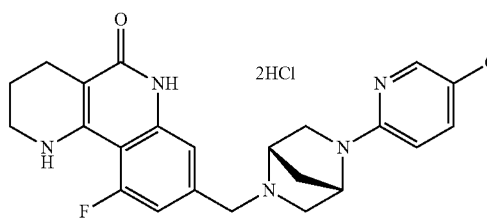 | $^1$H NMR (400 MHz, DMSO-$d_6$); δ 11.42 (br, 1H), 11.10 (br, 1H), 8.49 (s, 1H), 7.89 (d, J = 9.2 Hz, 1H), 7.47 (d, J = 14.4 Hz, 1H), 7.21 (s, 1H), 6.71 (br, 1H), 5.08-4.98 (m, 1H), 4.60-4.52 (m, 1H), 4.47 (br, 2H), 4.40-4.32 (m, 1H), 3.68-3.54 (m, 2H), 3.50-3.40 (m, 1H), 3.36-3.20 (m, 1H), 2.62-2.56 (m, 1H), 2.54-2.40 (m, 3H), 2.20-2.12 (m, 1H), 1.82-1.70 (m, 2H) |

Example 178: Synthesis of 10-fluoro-8-{[4-(pyrazin-2-yl)piperazin-1-yl]methyl}-1,2,3,4-tetrahydrobenzo[h][1,6]naphthyridin-5(6H)-one Dihydrochloride Step 1: Synthesis of 8-(chloromethyl)-10-fluoro-1,2,3,4-tetrahydrobenzo[h][1,6]naphthyridin-5(6H)-one

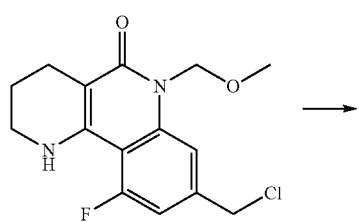

-continued

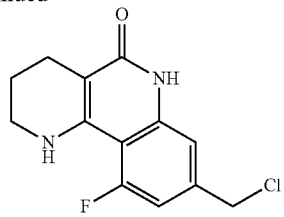

To the compound (163 mg, 0.52 mmol) prepared in step 7 of Example 166, dichloromethane (8.0 ml) was added, and then trifluoroacetic acid (1.5 ml) was added. The reaction was performed by stirring the mixture at 50° C. for 24 hours. The reaction solution was cooled to room temperature, and then neutralized with a saturated aqueous solution of sodium hydrogen carbonate. The organic layer was dried with anhydrous magnesium sulfate, and then concentrated under reduced pressure to give the title compound (124 mg, 89%, yellow solid).

$^1$H NMR (400 MHz, DMSO-d$_6$); δ 11.11 (br, 1H), 7.08 (s, 1H), 6.94 (d, J=14.8 Hz, 1H), 6.56 (d, J=14.0 Hz, 1H), 4.75 (s, 2H), 3.30-3.20 (m, 2H), 2.50-2.40 (m, 2H), 1.80-1.70 (m, 2H).

Step 2: Synthesis of 10-fluoro-8-{[4-piperazin-2-yl)piperazin-1-yl]methyl}-1,2,3,4-tetrahydrobenzo[h][1,6]naphthyridin-5(6H)-one

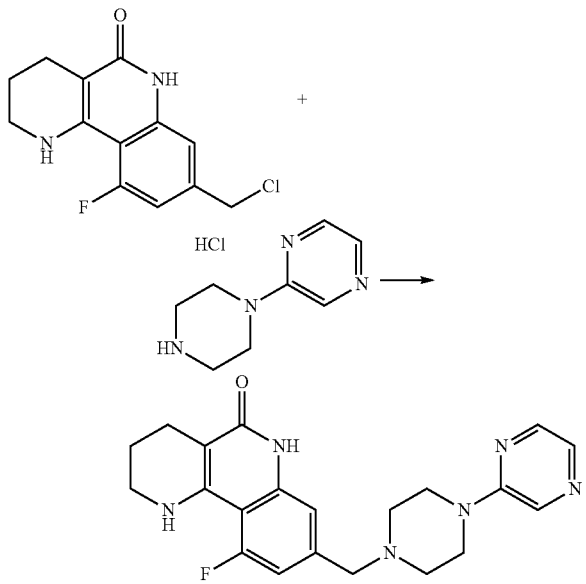

Using the compound (33 mg, 0.12 mmol) prepared in step 1, the title compound (16 mg, yield: 33%, white solid) was obtained in the same manner as step 7 of Example 1.

$^1$H NMR (400 MHz, DMSO-d$_6$); δ 10.95 (br, 1H), 8.29 (s, 1H), 8.06 (s, 1H), 7.82 (d, J=2.8 Hz, 1H), 7.03 (s, 1H), 6.84 (d, J=14.4 Hz, 1H), 6.57 (d, J=14.0 Hz, 1H), 4.00-3.20 (m, 12H), 2.50-2.40 (m, 2H), 1.80-1.70 (m, 2H).

Step 3: Synthesis of 10-fluoro-8-{[4-(pyrazin-2-yl)piperazin-1-yl]methyl}-1,2,3,4-tetrahydrobenzo[h][1,6]naphthyridin-5(6H)-one dihydrochloride

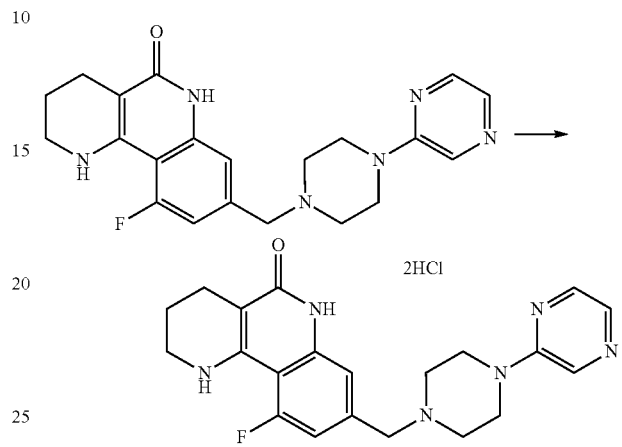

Using the compound (11 mg, 0.03 mmol) prepared in step 2, the title compound (5 mg, yield: 38%, white solid) was obtained in the same manner as step 9 of Example 1.

$^1$H NMR (400 MHz, DMSO-d$_6$); δ 11.47 (br, 1H), 11.37 (br, 1H), 8.42 (s, 1H), 8.16 (s, 1H), 7.95 (d, J=2.4 Hz, 1H), 7.37 (d, J=14.0 Hz, 1H), 7.12 (s, 1H), 4.50-4.30 (m, 4H), 3.50-3.25 (m, 6H), 3.20-3.05 (m, 2H), 2.50-2.42 (m, 2H), 1.80-1.70 (m, 2H).

Compounds of Examples 179 to 185 were prepared in the same manner as described in Examples 178, except that substituents were changed as shown in Table 4 below.

TABLE 4

| Example | Structure | NMR |
|---|---|---|
| 179 | 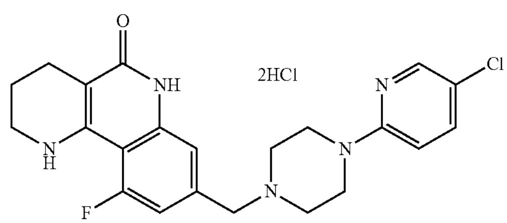 [SMILES: O=c1[nH]c2cc(CN3CCN(c4ccc(Cl)cn4)CC3)cc(F)c2c2c1CCCN2] | $^1$H NMR (400 MHz, DMSO-d$_6$); δ 8.17 (s, 1H), 7.70 (d, J = 8.8 Hz, 1H), 7.60 (s, 1H), 7.40 (d, J = 14.0 Hz, 1H), 6.99 (d, J = 9.6 Hz, 1H), 4.42 (s, 2H), 4.40-4.25 (m, 2H), 3.45-3.25 (m, 6H), 3.15-3.00 (m, 2H), 2.60-2.40 (m, 2H), 1.85-1.75 (m, 2H) |
| 180 | 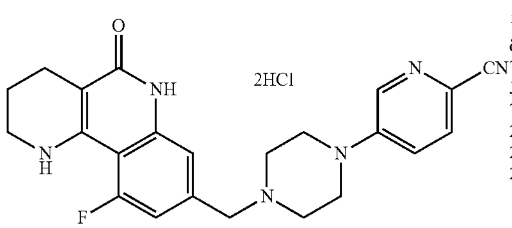 | $^1$H NMR (400 MHz, DMSO-d$_6$); δ 11.39 (br, 2H), 8.48 (d, J = 2.4 Hz, 1H), 7.85 (d, J = 9.2 Hz, 1H), 7.46 (dd, J1 = 8.8 Hz, J2 = 3.2 Hz, 1H), 7.35 (d, J = 14.4 Hz, 1H), 7.10 (s, 1H), 4.37 (s, 2H), 4.20-4.10 (m, 2H), 3.50-3.25 (m, 6H), 3.22-3.10 (m, 2H), 2.60-2.40 (m, 2H), 1.80-1.70 (m, 2H) |

TABLE 4-continued

| Example | Structure | NMR |
|---|---|---|
| 181 | 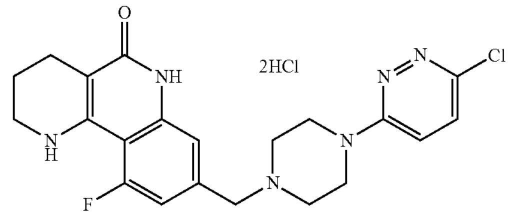 [SMILES: O=c1[nH]c2cc(CN3CCN(c4ccc(Cl)nn4)CC3)cc(F)c2c2c1CCCN2] | $^1$H NMR (400 MHz, DMSO-$d_6$); δ 11.78 (br, 1H), 11.46 (br, 1H), 7.66 (d, J = 9.2 Hz, 1H), 7.49 (d, J = 9.2 Hz, 1H), 7.44 (d, J = 14.0 Hz, 1H), 7.14 (s, 1H), 5.00-4.50 (br, 2H), 4.50-4.30 (m, 6H), 3.55-3.40 (m, 2H), 3.40-3.25 (m, 4H), 2.50-2.40 (m, 4H), 1.80-1.70 (m, 2H) |
| 182 | 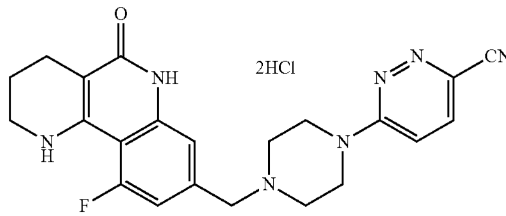 | $^1$H NMR (400 MHz, DMSO-$d_6$); δ 11.37 (br, 2H), 8.01 (d, J = 10 Hz, 1H), 7.47 (d, J = 10.4 Hz, 1H), 7.32 (d, J = 14 Hz, 1H), 7.09 (s, 1H), 4.70-4.60 (m, 2H), 4.35 (s, 2H), 3.60-3.47 (m, 2H), 3.47-3.37 (m, 2H), 3.35-3.27 (m, 2H), 3.22-3.10 (m, 2H), 2.70-2.30 (m, 2H), 1.80-1.70 (m, 2H) |
| 183 | 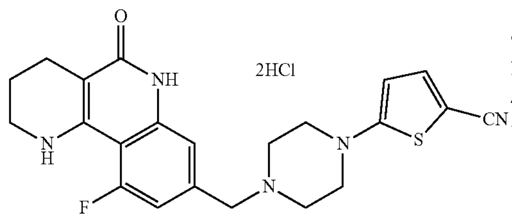 [SMILES: N#Cc1ccc(N2CCN(Cc3cc(F)c4c5c(c(=O)[nH]c4c3)CCCN5)CC2)s1] | $^1$H NMR (400 MHz, DMSO-$d_6$); δ 11.43 (br, 1H), 11.36 (br, 1H), 7.69 (d, J = 4.4 Hz, 1H), 7.33 (d, J = 15.6 Hz, 1H), 7.10 (s, 1H), 6.38 (d, J = 4 Hz, 1H), 4.76 (br, 2H), 4.00-3.50 (m, 4H), 3.50-3.15 (m, 6H), 2.50-2.40 (m, 2H), 1.80-1.70 (m, 2H) |
| 184 | 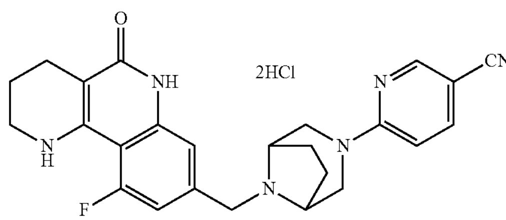 | $^1$H NMR (400 MHz, DMSO-$d_6$); δ 11.87 (br, 1H), 11.42 (br, 1H), 8.54 (s, 1H), 7.96 (d, J = 8.8 Hz, 1H), 7.55 (d, J = 14.4 Hz, 1H), 7.25 (s, 1H), 4.35-4.20 (m, 2H), 4.05-3.95 (m, 2H), 3.70-3.60 (m, 2H), 3.40-3.25 (m, 2H), 2.50-2.40 (m, 2H), 2.35-2.20 (m, 2H), 1.90-1.70 (m, 4H) |
| 185 | 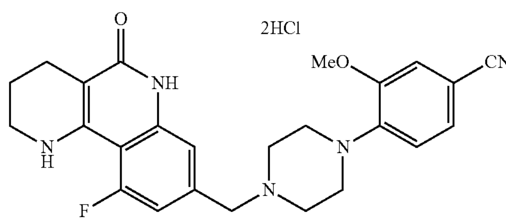 [SMILES: COc1cc(C#N)ccc1N1CCN(Cc2cc(F)c3c4c(c(=O)[nH]c3c2)CCCN4)CC1] | $^1$H NMR (400 MHz, DMSO-$d_6$); δ 11.44 (br, 1H), 11.29 (br, 1H), 7.50-7.25 (m, 3H), 7.20-6.90 (m, 2H), 4.33 (br, 2H), 4.20-2.90 (m, 13H), 2.60-2.40 (m, 2H), 1.80-1.70 (m, 2H) |

Example 186: Synthesis of 5-[4-(5-oxo-1,2,3,4,5,6-hexahydrobenzo[h][1,6]naphthyridin-8-carbonyl)piperazin-1-yl]thiophene-2-carbonitrile Dihydrochloride Step 1: Synthesis of ethyl 5-oxo-1,2,3,4,5,6-hexahydrobenzo[h][1,6]naphthyridin-8-carboxylate

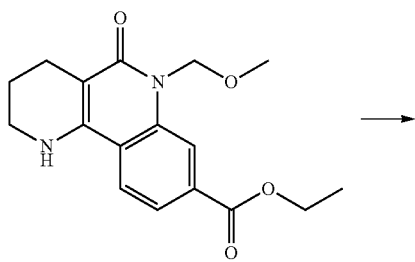

-continued

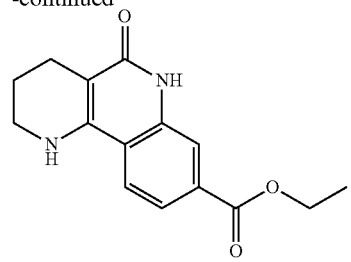

To the compound (500 mg, 1.56 mmol) prepared in step 4 of Example 1, ethanol (50 mL) was added, and then 12N hydrochloric acid (5.0 mL, 15.60 mmol) was added slowly dropwise, followed by reaction at room temperature for 24 hours. The reaction mixture was concentrated under reduced pressure to remove ethanol, and then cooled to 0° C. by addition of water (5.0 mL), after which it was neutralized with 4N sodium hydroxide solution. After stirring for 1 hour, the produced solid was filtered and washed with water to give the title compound (423 mg, 99%, yellow solid).

$^1$H NMR (400 MHz, CD$_3$OD); δ 7.91 (s, 1H), 7.79 (d, J=8.4 Hz, 1H), 7.72 (d, J=8.4 Hz, 1H), 4.63 (br. 2H), 3.45-3.00 (m, 2H), 2.62-2.52 (m, 2H), 1.95-1.80 (m, 2H), 1.35 (t, J=7.2 Hz, 3H).

Step 2: Synthesis of 5-oxo-1,2,3,4,5,6-hexahydrobenzo[h][1,6]naphthyridin-8-carboxylic acid

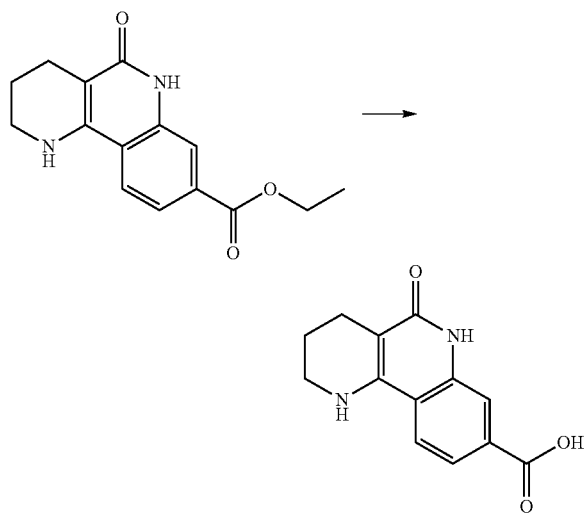

The compound (150 mg, 0.55 mmol) prepared in step 1 was dissolved in methanol (6 ml), and then aqueous sodium hydroxide solution (200 mg sodium hydroxide in 3 ml water) was added thereto. The reaction solution was cooled under reflux for 24 hours, and then concentrated under reduced pressure to remove the solvent. Ethyl acetate was added to the concentrated residue, followed by neutralization with 2N hydrochloric acid. The produced solid was filtered and washed with ethyl acetate.

$^1$H NMR (400 MHz, DMSO-d$_6$); δ 11.04 (br, 1H), 7.88 (d, J=8.0 Hz, 1H), 7.28 (s, 1H), 7.59 (d, J=8.0 Hz, 1H), 7.06 (br, 1H), 3.30-3.20 (m, 2H), 2.50-2.40 (m, 2H), 1.90-1.80 (m, 2H).

Step 3: Synthesis of 5-[4-(5-oxo-1,2,3,4,5,6-hexahydrobenzo[h][1,6]naphthyridin-8-carbonyl)piperazin-1-yl]thiophene-2-carbonitrile

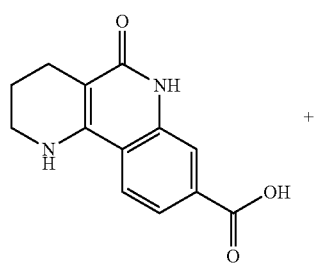

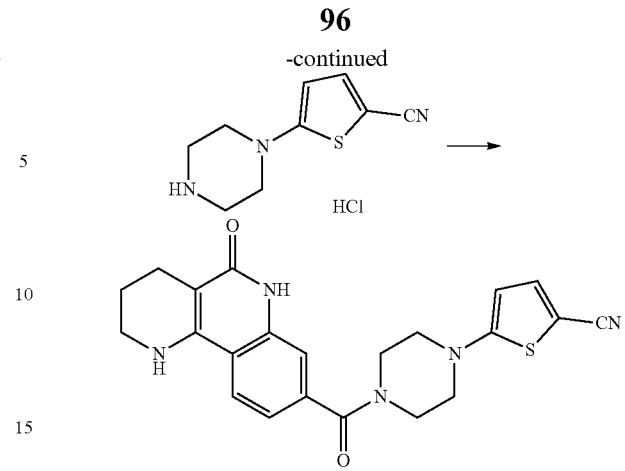

The compound (30 mg, 0.12 mmol) prepared in step 2 was dissolved in dimethylformamide (3 ml), and then 1-ethyl-3-(3-dimethylaminopropyl)carbodiimide (35 mg, 0.18 mmol), hydroxybenzotriazole (25 mg, 0.18 mmol), 4-methylmorpholine (70 uL, 0.64 mmol), 5-(piperazin-1-yl)-thiophene-carbonitrile hydrochloride (38 mg, 0.17 mmol) were added thereto. The mixture was stirred for 1 hour at room temperature. After completion of the reaction, water was added, followed by the extraction three times with ethyl acetate. The organic solvent layer was dried with anhydrous magnesium sulfate and concentrated under reduced pressure. The residue obtained by concentration under reduced pressure was purified by column chromatography (dichloromethane:methanol=20:1) to give the title compound (37 mg, yield: 71%, white solid).

$^1$H NMR (400 MHz, CD$_3$OD); δ 7.88 (d, J=8.0 Hz, 1H), 7.48 (d, J=4.4 Hz, 1H), 7.38 (d, J=0.8 Hz, 1H), 7.28 (d, J=8.4 Hz, 1.6 Hz, 1H), 6.26 (d, J=4.0 Hz, 1H), 3.96 (br, 2H), 3.65 (br, 2H), 3.50-3.20 (m, 6H), 2.60-2.50 (m, 2H), 2.00-1.90 (m, 2H).

Step 4: Synthesis of 5-[4-(5-oxo-1,2,3,4,5,6-hexahydrobenzo[h][1,6]naphthyridin-8-carbonyl)piperazin-1-yl]thiophene-2-carbonitrile dihydrochloride

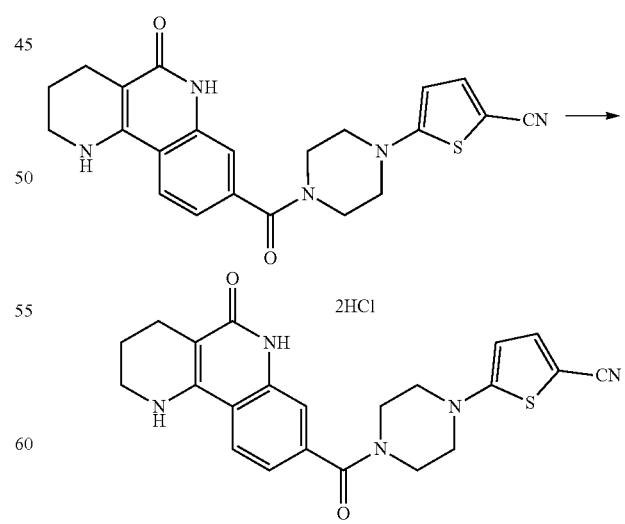

Using the compound (25 mg, 0.06 mmol) prepared in step 3, the title compound (27 mg, yield: 91%, white solid) was obtained in the same manner as step 9 of Example 1.

¹H NMR (400 MHz, DMSO-d₆); δ 11.13 (br, 1H), 7.90 (d, J=8.4 Hz, 1H), 7.64 (d, J=4.4 Hz, 1H), 7.28 (s, 1H), 7.17 (d, J=7.6 Hz, 1H), 6.30 (d, J=4.4 Hz, 1H), 3.80-3.50 (m, 4H), 3.45-3.20 (m, 6H), 2.60-2.40 (m, 2H), 1.80-1.70 (m, 2H).

Compounds of Examples 187 to 189 were prepared in the same manner as described in Examples 186, except that substituents were changed as shown in Table 5 below.

TABLE 5

| Example | Structure | NMR |
|---|---|---|
| 187 | (structure with 2HCl) | ¹H NMR (400 MHz, DMSO-d₆); δ 11.03 (s, 1H), 8.52 (s, 2H), 7.92-7.89 (m, 2H), 7.27 (s, 1H), 7.17 (d, J = 7.2 Hz, 1H), 6.95 (d, J = 7.6 Hz, 1H), 3.79-3.60 (m, 8H), 3.60-3.40 (m, 2H), 3.36-3.32 (m, 2H), 1.85-1.75 (m, 2H) |
| 188 | (structure with 2HCl) | ¹H NMR (400 MHz, DMSO-d₆); δ 11.34 (s, 1H), 8.00 (s, 1H), 7.95 (d, J = 8.4 Hz, 1H), 7.33 (s, 1H), 7.20 (d, J = 8.8 Hz, 1H), 4.78 (br, 4H), 3.75-3.33 (m, 8H), 1.80-1.65 (m, 2H) |
| 189 | (structure with 2HCl) | ¹H NMR (400 MHz, DMSO-d₆); δ 11.20 (s, 1H), 8.04 (s, 1H), 7.90 (d, J = 8.4 Hz, 1H), 7.29 (s, 1H), 7.17 (d, J = 7.6 Hz, 1h), 4.19 (br, 4H), 3.75-3.62 (m, 6H), 3.40-3.30 (m, 2H), 1.97-1.80 (m, 2H) |

Experimental Example 1: Experiment on Inhibition of Poly(ADP-Ribose)Polymerase [PARP-1] Enzyme The PARP-1 enzyme inhibitory activities of the compounds of the present invention were assayed in the following manner by use of a kit (cat. 80551) purchased from BPS Bioscience.

The 96-well plate provided in BPS Bioscience kit was coated with histone and incubated at 4° C. for 16 hours. Then, the plate was washed four times with PBST (7.5 mM Na₂HPO₄, 2.5 mM NaH₂PO₄, 145 mM NaCl, 0.05% Tween 20, pH 7.4), and blocking buffer (provided in BPS Bioscience kit) was added thereto in order to block nonspecific reaction, and was then incubated at 25° C. for 1 hour. After incubation for 1 hour, the plate was washed four times with PBST, and varying concentrations of each of the compounds of the Examples were added to a reaction solution containing PARP-1 enzyme (50 ng/well), an assay mixture and activated DNA, and allowed to react at 25° C. for 1 hour. After 1 hour, each well was washed four times with PBST, and in order to measure the level of ribosylation by PARP enzyme, streptavidin-linked peroxidase (Strep-HRP, 1:50 dilution) was added and allowed to react at 25° C. for 30 minutes. The plate was washed four times with PBST, and then finally an HRP chemiluminescent substrate was added and allowed to react. The level of histone ribosylation formed by each enzyme was quantified using Synergy™ H4 Hybrid Multi-Mode Microplate Reader (BioTek Instruments, Inc., USA). The results obtained for various concentrations of the compounds of the present invention are average values obtained from two wells, and the results were analyzed by calculating the IC₅₀ values of the compounds using SigmaPlot 10 (Systat Software Inc., USA) (see Table 6).

TABLE 6

| Example | PARP-1 enzyme (nM) |
|---|---|
| 1 | 4.99 |
| 2 | 13.70 |
| 3 | 29.57 |
| 5 | 17.97 |
| 6 | 27.98 |
| 7 | 20.15 |
| 9 | 24.63 |
| 10 | 115.13 |
| 12 | 128.56 |
| 13 | 33.75 |
| 15 | 16.04 |
| 16 | 42.99 |
| 17 | 15.36 |
| 18 | 18.31 |
| 19 | 17.98 |
| 20 | 22.78 |

TABLE 6-continued

| Example | PARP-1 enzyme (nM) |
|---|---|
| 21 | 53.20 |
| 22 | 89.96 |
| 23 | 38.55 |
| 24 | 33.53 |
| 25 | 57.07 |
| 26 | 100.61 |
| 27 | 59.63 |
| 28 | 92.00 |
| 29 | 24.71 |
| 30 | 23.45 |
| 31 | 27.75 |
| 32 | 43.98 |
| 33 | 28.87 |
| 34 | 31.60 |
| 35 | 25.84 |
| 36 | 52.37 |
| 37 | 52.27 |
| 38 | 58.94 |
| 39 | 9.13 |
| 40 | 14.65 |
| 41 | 11.52 |
| 42 | 13.72 |
| 43 | 21.74 |
| 44 | 11.57 |
| 45 | 63.13 |
| 46 | 32.51 |
| 47 | 17.33 |
| 48 | 6.49 |
| 49 | 11.08 |
| 50 | 6.65 |
| 51 | 7.69 |
| 52 | 15.93 |
| 53 | 6.44 |
| 54 | 7.47 |
| 55 | 30.09 |
| 56 | 6.67 |
| 57 | 5.98 |
| 58 | 11.57 |
| 59 | 1.95 |
| 60 | 4.80 |
| 61 | 11.12 |
| 62 | 27.82 |
| 63 | 4.46 |
| 64 | 7.55 |
| 65 | 7.85 |
| 66 | 5.51 |
| 67 | 6.59 |
| 68 | 4.74 |
| 69 | 3.04 |
| 70 | 7.90 |
| 71 | 6.87 |
| 72 | 10.54 |
| 73 | 9.73 |
| 74 | 7.11 |
| 75 | 7.27 |
| 76 | 10.87 |
| 77 | 7.11 |
| 78 | 6.64 |
| 79 | 14.40 |
| 80 | 22.34 |
| 81 | 9.58 |
| 82 | 22.11 |
| 83 | 26.44 |
| 84 | 11.91 |
| 85 | 9.87 |
| 86 | 14.08 |
| 87 | 28.63 |
| 88 | 13.48 |
| 89 | 2.35 |
| 90 | 5.49 |
| 91 | 6.61 |
| 92 | 4.92 |
| 93 | 3.25 |
| 94 | 12.93 |
| 95 | 8.59 |
| 96 | 6.01 |
| 97 | 7.38 |
| 98 | 5.04 |
| 99 | 57.63 |
| 100 | 32.33 |
| 101 | 3.87 |
| 102 | 6.67 |
| 103 | 7.00 |
| 104 | 8.16 |
| 105 | 56.85 |
| 106 | 32.01 |
| 107 | 24.38 |
| 108 | 12.35 |
| 109 | 19.83 |
| 110 | 14.25 |
| 111 | 9.01 |
| 112 | 5.61 |
| 113 | 10.31 |
| 114 | 52.90 |
| 115 | 17.42 |
| 116 | 21.22 |
| 117 | 111.98 |
| 118 | 179.64 |
| 119 | 4.82 |
| 120 | 4.81 |
| 121 | 13.97 |
| 122 | 19.42 |
| 123 | 3.49 |
| 124 | 7.09 |
| 125 | 7.08 |
| 126 | 77.15 |
| 127 | 10.38 |
| 128 | 4.50 |
| 129 | 6.28 |
| 130 | 17.35 |
| 131 | 7.59 |
| 132 | 3.60 |
| 133 | 8.29 |
| 134 | 12.23 |
| 135 | 3.66 |
| 136 | 10.31 |
| 137 | 7.43 |
| 138 | 17.61 |
| 139 | 85.82 |
| 140 | 3.05 |
| 141 | 8.83 |
| 142 | 4.60 |
| 143 | 39.79 |
| 144 | 107.73 |
| 145 | 25.41 |
| 146 | 302.93 |
| 147 | 15.88 |
| 148 | 24.51 |
| 149 | 7.61 |
| 150 | 2.49 |
| 151 | 5.65 |
| 152 | 4.86 |
| 153 | 44.84 |
| 154 | 77.37 |
| 155 | 29.26 |
| 156 | 20.36 |
| 157 | 17.88 |
| 158 | 8.23 |
| 159 | 139.8 |
| 160 | 4.82 |
| 161 | 9.41 |
| 162 | 10.22 |
| 163 | 43.45 |
| 164 | 81.74 |
| 165 | 37.01 |
| 166 | 7.46 |
| 167 | 7.24 |
| 168 | 19.63 |
| 169 | 8.47 |
| 170 | 3.30 |
| 171 | 4.99 |
| 172 | 7.94 |
| 173 | 23.98 |
| 174 | 109.76 |

TABLE 6-continued

| Example | PARP-1 enzyme (nM) |
|---|---|
| 175 | 18.57 |
| 176 | 11.47 |
| 177 | 7.28 |
| 178 | 7.33 |
| 179 | 159.00 |
| 180 | 5.27 |
| 181 | 4.65 |
| 182 | 4.02 |
| 183 | 5.04 |
| 184 | 5.79 |
| 185 | 11.78 |
| 186 | 13.28 |
| 187 | 5.92 |
| 188 | 47.98 |
| 189 | 7.43 |

Experimental Example 2: Experiment on Inhibition of Tankyrase-1 and 2 Enzymes

The tankyrase-1 or tankyrase-2 enzyme inhibitory activities of the compounds of the present invention were assayed in the following manner by use of a kit (cat. 80573 or 80578) purchased from BPS Bioscience.

The 96-well plate provided in BPS Bioscience kit was coated with histone and incubated at 4° C. for 16 hours. Then, the plate was washed four times with PBST (7.5 mM $Na_2HPO_4$, 2.5 mM $NaH_2PO_4$, 145 mM NaCl, 0.05% Tween 20, pH 7.4), and blocking buffer (provided in BPS Bioscience kit) was added thereto in order to block nonspecific reaction, and was then incubated at 25° C. for 1 hour. After incubation for 1 hour, the plate was washed four times with PBST, and varying concentrations of each of the compounds of the Examples were added to a reaction solution containing tankyrase-1 enzyme (40 ng/well) or tankyrase-2 enzyme (15 ng/well) and an assay mixture, and allowed to react at 25° C. for 1 hour. After 1 hour, each well was washed four times with PBST, and in order to measure the level of ribosylation by PARP enzyme, streptavidin-linked peroxidase (Strep-HRP, 1:50 dilution) was added and allowed to react at 25° C. for 30 minutes. The plate was washed four times with PBST, and then finally an HRP chemiluminescent substrate was added and allowed to react. The level of histone ribosylation formed by each enzyme was quantified using Synergy™ H4 Hybrid Multi-Mode Microplate Reader (BioTek Instruments, Inc., USA). The results obtained for various concentration of the compounds of the present invention are average values obtained from two wells, and the results were analyzed by calculating the $IC_{50}$ values of the compounds using SigmaPlot 10 (Systat Software Inc., USA) (see Tables 7 and 8).

TABLE 7

| Example | TNK-1 enzyme (nM) |
|---|---|
| 1 | 59.58 |
| 7 | 34.03 |
| 39 | 35.18 |
| 48 | 89.07 |
| 50 | 34.95 |
| 51 | 31.35 |
| 52 | 56.42 |
| 53 | 20.10 |
| 54 | 16.75 |
| 56 | 4.96 |
| 57 | 26.52 |
| 59 | 1.37 |
| 60 | 12.11 |
| 61 | 13.68 |
| 62 | 26.18 |
| 63 | 15.02 |
| 64 | 16.17 |
| 65 | 13.87 |
| 66 | 13.21 |
| 67 | 14.03 |
| 68 | 49.19 |
| 69 | 5.77 |
| 70 | 12.37 |
| 71 | 14.19 |
| 72 | 16.34 |
| 73 | 15.55 |
| 74 | 17.26 |
| 75 | 11.38 |
| 76 | 11.28 |
| 77 | 16.28 |
| 78 | 10.96 |
| 80 | 39.86 |
| 81 | 45.93 |
| 82 | 35.07 |
| 84 | 8.46 |
| 85 | 11.76 |
| 89 | 5.07 |
| 90 | 30.98 |
| 91 | 35.20 |
| 92 | 12.87 |
| 93 | 3.59 |
| 94 | 42.44 |
| 95 | 11.45 |
| 96 | 6.77 |
| 97 | 8.81 |
| 98 | 36.72 |
| 99 | 5.59 |
| 100 | 18.92 |
| 101 | 25.16 |
| 102 | 28.81 |
| 103 | 12.46 |
| 104 | 50.71 |
| 107 | 11.40 |
| 108 | 25.12 |
| 110 | 38.47 |
| 111 | 18.77 |
| 112 | 12.55 |
| 113 | 10.66 |
| 119 | 5.00 |
| 120 | 10.20 |
| 122 | 7.28 |
| 123 | 3.92 |
| 124 | 10.43 |
| 125 | 10.40 |
| 128 | 25.76 |
| 129 | 5.56 |
| 131 | 9.89 |
| 132 | 2.77 |
| 133 | 14.19 |
| 134 | 4.15 |
| 135 | 4.04 |
| 137 | 3.36 |
| 139 | 10.57 |
| 140 | 18.53 |
| 141 | 5.82 |
| 142 | 4.42 |
| 143 | 21.45 |
| 145 | 6.29 |
| 149 | 14.26 |
| 150 | 18.05 |
| 151 | 56.67 |
| 152 | 16.97 |
| 158 | 17.33 |
| 160 | 10.65 |
| 161 | 32.04 |
| 166 | 36.28 |
| 167 | 97.20 |

TABLE 7-continued

| Example | TNK-1 enzyme (nM) |
|---|---|
| 169 | 32.39 |
| 170 | 9.65 |
| 171 | 16.65 |
| 172 | 162.00 |
| 174 | 90.32 |
| 176 | 116.40 |
| 177 | 14.78 |
| 178 | 27.33 |
| 180 | 8.05 |
| 181 | 11.57 |
| 182 | 3.33 |
| 183 | 46.16 |
| 184 | 37.08 |
| 185 | 35.79 |
| 186 | 47.13 |
| 187 | 22.92 |
| 189 | 16.05 |

TABLE 8

| Example | TNK-2 enzyme (nM) |
|---|---|
| 48 | 49.94 |
| 50 | 14.52 |
| 51 | 14.81 |
| 53 | 10.23 |
| 54 | 12.79 |
| 56 | 3.78 |
| 59 | 0.92 |
| 60 | 6.47 |
| 61 | 3.80 |
| 63 | 4.96 |
| 64 | 3.38 |
| 65 | 4.20 |
| 67 | 4.36 |
| 69 | 1.32 |
| 76 | 2.86 |
| 78 | 1.87 |
| 85 | 10.35 |
| 89 | 1.48 |
| 90 | 13.22 |
| 91 | 11.40 |
| 93 | 1.97 |
| 96 | 1.75 |
| 97 | 3.70 |
| 99 | 1.99 |
| 101 | 15.84 |
| 103 | 2.10 |
| 107 | 6.21 |
| 113 | 3.49 |
| 119 | 1.38 |
| 120 | 4.82 |
| 122 | 2.37 |
| 123 | 2.38 |
| 124 | 4.71 |
| 125 | 3.18 |
| 129 | 1.65 |
| 131 | 2.81 |
| 132 | 1.31 |
| 134 | 2.70 |
| 135 | 1.75 nM |
| 137 | 0.95 nM |
| 141 | 2.62 nM |
| 142 | 2.45 nM |
| 143 | 12.01 nM |
| 145 | 3.24 nM |
| 149 | 6.99 nM |
| 150 | 6.06 nM |
| 152 | 10.56 nM |
| 158 | 6.59 nM |
| 160 | 4.63 nM |
| 161 | 8.60 nM |
| 169 | 34.67 nM |

TABLE 8-continued

| Example | TNK-2 enzyme (nM) |
|---|---|
| 170 | 1.96 nM |
| 172 | 67.41 nM |
| 177 | 10.65 nM |
| 180 | 2.12 nM |
| 182 | 1.26 nM |
| 189 | 14.07 nM |

Experimental Example 3: Experiment on Inhibition of PARP-1 Enzyme Using Cells

In order to examine the PARP-1 enzyme inhibitory abilities of the compounds of the present invention, the amount of PAR produced in cells was measured.

HCT-15 colorectal cancer cells were cultured in RPMI medium containing 10% fetal bovine serum (FBS). The cultured HCT-15 cells were seeded on a 96-well plate at a density of $2 \times 10^4$ cells/well, and then cultured under the conditions of 37° C. and 5% $CO_2$ for 16 hours. After culture, the cells were treated with varying concentrations of each of the compounds of the Examples, and then cultured at 37° C. for 30 minutes. Next, the cells were treated with 50 mM of the DNA damage material $H_2O_2$, and then reacted at 25° C. for 5 minutes and fixed with methanol/acetone (7/3) at −20° C. for 10 minutes. After 10 minutes, the plate was washed three times with TBST, and then 5% non-fat dry milk was added thereto in order to prevent nonspecific reactions, followed by incubation at 25° C. for 1 hour. After 1 hour, anti-PAR antibody (1:1000 dilution) was added and allowed to react at 25° C. for 1 hour, and the plate was washed three times with TBST. Next, HRP-conjugated anti-mouse antibody (1:1000 dilution) was added and allowed to react at 25° C. for 1 hour. The plate was washed three times with TBST, and then finally an HRP chemiluminescent substrate was added and allowed to react. The amount of PAR produced in the cells was quantified using Synergy™ H4 Hybrid Multi-Mode Microplate Reader (BioTek Instruments, Inc., USA). The results obtained for various concentration of the compounds of the present invention are average values obtained from three wells, and the results were analyzed by calculating the $IC_{50}$ values of the compounds using SigmaPlot 10 (Systat Software Inc., USA) (see Table 9).

TABLE 9

| Example | PARP-1 cell (nM) |
|---|---|
| 1 | 3.56 |
| 7 | 10.65 |
| 20 | 31.12 |
| 39 | 8.17 |
| 48 | 2.01 |
| 50 | 4.06 |
| 51 | 3.97 |
| 52 | 9.48 |
| 53 | 2.56 |
| 54 | 5.96 |
| 56 | 8.48 |
| 57 | 2.30 |
| 59 | 0.43 |
| 60 | 1.95 |
| 61 | 3.32 |
| 62 | 19.50 |
| 63 | 5.17 |
| 64 | 17.65 |
| 65 | 20.33 |

TABLE 9-continued

| Example | PARP-1 cell (nM) |
|---|---|
| 66 | 39.73 |
| 67 | 10.24 |
| 68 | 5.21 |
| 69 | 10.09 |
| 70 | 26.18 |
| 71 | 19.16 |
| 72 | 53.99 |
| 73 | 33.46 |
| 74 | 39.11 |
| 75 | 31.32 |
| 76 | 12.31 |
| 77 | 11.04 |
| 78 | 12.78 |
| 79 | 38.26 |
| 80 | 58.77 |
| 81 | 18.32 |
| 82 | 38.42 |
| 84 | 12.49 |
| 85 | 13.35 |
| 86 | 2.03 |
| 89 | 0.84 |
| 90 | 2.06 |
| 91 | 3.08 |
| 92 | 9.72 |
| 93 | 6.60 |
| 94 | 14.38 |
| 95 | 148.15 |
| 96 | 31.00 |
| 97 | 105.25 |
| 98 | 4.80 |
| 101 | 1.89 |
| 102 | 8.52 |
| 103 | 4.71 |
| 104 | 13.45 |
| 107 | 1.30 |
| 108 | 7.93 |
| 110 | 11.52 |
| 111 | 8.20 |
| 112 | 3.45 |
| 113 | 9.98 |
| 119 | 5.53 |
| 120 | 3.38 |
| 123 | 3.16 |
| 124 | 10.55 |
| 125 | 11.74 |
| 128 | 6.76 |
| 129 | 8.79 |
| 131 | 33.79 |
| 132 | 20.05 |
| 133 | 4.42 |
| 134 | 14.12 |
| 135 | 9.15 |
| 137 | 42.59 |
| 140 | 2.25 |
| 141 | 16.38 |
| 142 | 1.11 |
| 149 | 9.74 |
| 150 | 10.06 |
| 151 | 10.99 |
| 152 | 20.61 |
| 158 | 30.12 |
| 160 | 45.66 |
| 161 | 8.39 |
| 166 | 4.85 |
| 167 | 7.29 |
| 168 | 4.84 |
| 169 | 12.23 |
| 170 | 1.69 |
| 171 | 2.31 |
| 172 | 7.61 |
| 174 | 16.57 |
| 176 | 2.99 |
| 177 | 5.09 |
| 178 | 4.95 |
| 180 | 2.96 |
| 181 | 7.49 |
| 182 | 5.90 |

TABLE 9-continued

| Example | PARP-1 cell (nM) |
|---|---|
| 183 | 10.93 |
| 184 | 9.35 |
| 187 | 8.71 |
| 189 | 161.11 |

The compounds according to the present invention can inhibit PARP-1, tankyrase-1 or tankyrase-2 activity, and thus can be effectively used for prevention or treatment of neuropathic pain, neurodegenerative diseases, cardiovascular diseases, diabetic neuropathy, inflammatory diseases, osteoporosis, or cancer.

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

INDUSTRIAL APPLICABILITY

As described above, the tricyclic derivative compounds according to the present invention can inhibit PARP-1, tankyrase-1 or tankyrase-2 activity, and thus can be effectively used for prevention or treatment of neuropathic pain, neurodegenerative diseases, cardiovascular diseases, diabetic neuropathy, inflammatory diseases, osteoporosis, or cancer.

The invention claimed is:

1. A tricyclic compound represented by the following formula 1, an optical isomer thereof, a racemate thereof or a pharmaceutically acceptable salt thereof:

[Formula 1]

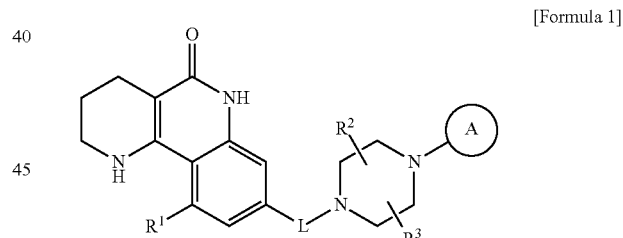

wherein
L is —$CH_2$— or —C(=O)—;
$R^1$ is H, a halogen atom, or $C_1$-$C_3$ alkoxy;
$R^2$ and $R^3$ are each independently H or $C_1$-$C_3$ alkyl, or $R^2$ and $R^3$ are linked to each other to form a ring;
ring A is phenyl or a heteroaryl, selected from the group consisting of pyridine, pyrazine, pyrimidine, pyridazine, thiophene, thiazole, thiadiazole, oxazole, oxadiazole, indole, indazole, cyclopentapyridine, dihydrocyclopentapyridine, furopyridine, dihydrofuropyridine, oxazolopyridine, benzoxazole and benzoisoxazole.
wherein the phenyl and the heteroaryl are each independently unsubstituted, or one or more H atoms thereof are each independently substituted with a substituent selected from the group consisting of a halogen atom, —CN, —$CF_3$, —$C_1$-$C_3$ alkyl, —$C_1$-$C_3$ alkoxy, —$CH_2$—$OR^4$, —C(=O)—$R^4$, —C(=O)—$OR^4$, —S(=O)$_2$—R$^4$, —NH—C(=O)—R$^4$, —NO$_2$, —NR$^4$R$^5$ and —C(=O)—NR$^6$R$^7$;

R$^4$, R$^5$ and R$^6$ are each independently H or C$_1$-C$_3$ alkyl; and

R$^7$ is C$_1$-C$_3$ alkyl or C$_3$-C$_7$ cycloalkyl.

2. The tricyclic compound, the optical isomer thereof, the racemate thereof or the pharmaceutically acceptable salt according to claim 1, wherein R$^2$ and R$^3$ are each independently H or C$_1$-C$_3$ alkyl.

3. The tricyclic compound, the optical isomer thereof, the racemate thereof or the pharmaceutically acceptable salt according to claim 2, wherein ring A is substituted with one or more substituents.

4. The tricyclic compound, the optical isomer thereof, the racemate thereof or the pharmaceutically acceptable salt according to claim 1, wherein R$^2$ and R$^3$ are linked to each other to form a ring.

5. The tricyclic compound, the optical isomer thereof, the racemate thereof or the pharmaceutically acceptable salt according to claim 1, wherein the compound is any one of the following compounds:

1) 8-{[4-(4-methoxyphenyl)piperazin-1-yl]methyl}-1,2,3,4-tetrahydrobenzo[h][1,6]naphthyridin-5(6H)-one;
2) 8-{[4-(4-fluorophenyl)piperazin-1-yl]methyl}-10-methoxy-1,2,3,4-tetrahydrobenzo[h][1,6]naphthyridin-5(6H)-one;
3) 10-ethoxy-8-{[4-(4-fluorophenyl)piperazin-1-yl]methyl}-1,2,3,4-tetrahydrobenzo[h][1,6]naphthyridin-5(6H)-one;
4) 10-ethoxy-8-({[4-(pyrimidin-2-yl)piperazin-1-yl]methyl}-1,2,3,4-tetrahydrobenzo[h][1,6]naphthyridin-5(6H)-one;
5) 10-ethoxy-8-{[4-(pyridin-2-yl)piperazin-1-yl]methyl}-1,2,3,4-tetrahydrobenzo[h][1,6]naphthyridin-5(6H)-one;
6) 10-ethoxy-8-{[4-(5-fluoropyrimidin-2-yl)piperazin-1-yl]methyl}-1,2,3,4-tetrahydrobenzo[h][1,6]naphthyridin-5(6H)-one;
7) 10-ethoxy-8-{[4-(5-fluoropyridin-2-yl)piperazin-1-yl]methyl}-1,2,3,4-tetrahydrobenzo[h][1,6]naphthyridin-5(6H)-one;
8) 10-ethoxy-8-{[4-(6-fluoropyridin-2-yl)piperazin-1-yl]methyl}-1,2,3,4-tetrahydrobenzo[h][1,6]naphthyridin-5(6H)-one;
9) 10-ethoxy-8-{[4-(3-fluoropyridin-2-yl)piperazin-1-yl]methyl}-1,2,3,4-tetrahydrobenzo[h][1,6]naphthyridin-5(6H)-one;
10) 8-{[4-(5-chloro-3-fluoropyridin-2-yl)piperazin-1-yl]methyl}-10-ethoxy-1,2,3,4-tetrahydrobenzo[h][1,6]naphthyridin-5(6H)-one;
11) 10-ethoxy-8-{[4-(6-(trifluoromethyl)pyridin-2-yl)piperazin-1-yl]methyl}-1,2,3,4-tetrahydrobenzo[h][1,6]naphthyridin-5(6H)-one;
12) 8-({4-[3-chloro-5-(trifluoromethyl)pyridin-2-yl]piperazin-1-yl}methyl)-10-ethoxy-1,2,3,4-tretrahydrobenzo[h][1,6]naphthyridin-5(6H)-one;
13) 8-{[4-(5-chloropyridin-2-yl)piperazin-1-yl]methyl}-10-ethoxy-1,2,3,4-tetrahydrobenzo[h][1,6]naphthyridin-5(6H)-one;
14) 8-{[4-(6-chloropyridin-2-yl)piperazin-1-yl]methyl}-10-ethoxy-1,2,3,4-tetrahydrobenzo[h][1,6]naphthyridin-5(6H)-one;
15) 8-{[4-(3-chloropyridin-2-yl)piperazin-1-yl]methyl}-10-ethoxy-1,2,3,4-tetrahydrobenzo[h][1,6]naphthyridin-5(6H)-one;
16) 8-{[4-(5-bromopyridin-2-yl)piperazin-1-yl]methyl}-10-ethoxy-1,2,3,4-tetrahydrobenzo[h][1,6]naphthyridin-5(6H)-one;
17) 10-ethoxy-8-{[4-(3-methylpyridin-2-yl)piperazin-1-yl]methyl}-1,2,3,4-tetrahydrobenzo[h][1,6]naphthyridin-5(6H)-one;
18) 6-{4-{(10-ethoxy-5-oxo-1,2,3,4,5,6-hexahydrobenzo[h][1,6]naphthyridin-8-yl)methyl]piperzin-1-yl})-N-methylnicotinamide;
19) 6-{4-{(10-ethoxy-5-oxo-1,2,3,4,5,6-hexahydrobenzo[h][1,6]naphthyridin-8-yl)methyl]piperazin-1-yl}-N-ethylnicotinamide;
20) N-cyclopropyl-6-{4-[(10-ethoxy-5-oxo-1,2,3,4,5,6-hexahydrobenzo[h][1,6]naphthyridin-8-yl)methyl]piperazin-1-yl}nicotinamide;
21) 8-{[4-(4-chlorophenyl)piperazin-1-yl]methyl}-10-ethoxy-1,2,3,4-tetrahydrobenzo[h][1,6]naphthyridin-5(6H)-one;
22) 8-{[4-(4-bromophenyl)piperazin-1-yl]methyl}-10-ethoxy-1,2,3,4-tetrahydrobenzo[h][1,6]naphthyridin-5(6H)-one;
23) 4-{4-[(1-ethoxy-5-oxo-1,2,3,4,5,6-hexahydrobenzo[h][1,6]naphthyridin-8-yl)methyl]piperazin-1-yl}benzonitrile;
24) 3-fluoro-4-{4-[(10-ethoxy-5-oxo-1,2,3,4,5,6-hexahydrobenzo[h]naphthyridin-8-yl)methyl]piperazin-1-yl}benzonitrile;
25) 3-chloro-4-{4-[(10-ethoxy-5-oxo-1,2,3,4,5,6-hexahydrobenzo[h][1,6]naphthyridin-8-yl)methyl]piperazin-1-yl}benzonitrile;
26) 4-{4-[(10-ethoxy-5-oxo-1,2,3,4,5,6-hexahydrobenzo[h][1,6]naphthyridin-8-yl)methyl]piperazin-1-yl}-3-methylbenzonitrile;
27) 10-ethoxy-8-{[4-(4-fluoro-2-methylphenyl)piperazin-1-yl]methyl}-1,2,3,4-tetrahydrobenzo[h][1,6]naphthyridin-5(6H)-one;
28) 4-{4-[(10-ethoxy-5-oxo-1,2,3,4,5,6-hexahydrobenzo[h][1,6]naphthyridin-8-yl)methyl]piperazin-1-yl}-3,5-difluorobenzonitrile;
29) 4-{4-[(10-ethoxy-5-oxo-1,2,3,4,5,6-hexahydrobenzo[h][1,6]naphthyridin-8-yl)methyl]piperazin-1-yl}-2-fluorobenzonitrile;
30) 4-{4-[(10-ethoxy-5-oxo-1,2,3,4,5,6-hexahydrobenzo[h][1,6]naphthyridin-8-yl)methyl]piperazin-1-yl}-N-ethylbenzamide;
31) 4-{4-[(10-ethoxy-5-oxo-1,2,3,4,5,6-hexahydrobenzo[h][1,6]naphthyridin-8-yl)methyl]piperazin-1-yl}-2-fluoro-N-methylbenzamide;
32) 4-{4-[(10-ethoxy-5-oxo-1,2,3,4,5,6-hexahydrobenzo[h][1,6]naphthyridin-8-yl)methyl]piperazin-1-yl}-N-ethyl-2-fluorobenzamide;
33) 3-chloro-4-{4-[(10-ethoxy-5-oxo-1,2,3,4,5,6-hexahydrobenzo[h][1,6]naphthyridin-8-yl)methyl]piperazin-1-yl}-N-ethylbenzamide;
34) 3-chloro-N-cyclopropyl-4-{4-[(10-ethoxy-5-oxo-1,2,3,4,5,6-hexahydrobenzo[h][1,6]naphthyridin-8-yl)methyl]piperazin-1-yl}benzamide;
35) 3-chloro-4-{4-[(10-ethoxy-5-oxo-1,2,3,4,5,6-hexahydrobenzo[h][1,6]naphthyridin-8-yl)methyl]piperazin-1-yl}-N-methylbenzamide;
36) 4-{4-[(10-ethoxy-5-oxo-1,2,3,4,5,6-hexahydrobenzo[h][1,6]naphthyridin-8-yl)methyl]piperazin-1-yl}-N,3-dimethylbenzamide;
37) 4-{4-[(1-ethoxy-5-oxo-1,2,3,4,5,6-hexahydrobenzo[h][1,6]naphthyridin-8-yl)methyl]piperazin-1-yl}-N-ethyl-3-methylbenzamide;

38) N-cyclopropyl-4-{4-[(10-ethoxy-5-oxo-1,2,3,4,5,6-hexahydrobenzo[h][1,6]naphthyridin-8-yl)methyl]piperazin-1-yl}-3-methylbenzamide;
39) 10-methoxy-8-{[4-(pyridin-2-yl)piperazin-1-yl]methyl}-1,2,3,4-tetrahydrobenzo[h][1,6]naphthyridin-5(6H)-one;
40) 10-methoxy-8-{[4-(3-methylpyridin-2-yl)piperazin-1-yl]methyl}-1,2,3,4-tetrahydrobenzo[h][1,6]naphthyridin-5(6H)-one;
41) 8-{[4-(5-fluoropyridin-2-yl)piperazin-1-yl]methyl}-10-methoxy-1,2,3,4-tetrahydrobenzo[h][1,6]naphthyridin-5(6H)-one;
42) 4-{4-[(1-methoxy-5-oxo-1,2,3,4,5,6-hexahydrobenzo[h][1,6]naphthyridin-8-yl)methyl]piperazin-1-yl}benzonitrile;
43) 8-{[4-(4-fluoro-2-methylphenyl)piperazin-1-yl]methyl}-10-methoxy-1,2,3,4-tetrahydrobenzo[h][1,6]naphthyridin-5(6H)-one;
44) 4-{4-[(10-methoxy-5-oxo-1,2,3,4,5,6-hexahydrobenzo[h][1,6]naphthyridin-8-yl)methyl]piperazin-1-yl}-3-methylbenzonitrile;
45) 3-fluoro-4-{4-[(10-methoxy-5-oxo-1,2,3,4,5,6-hexahydrobenzo[h]naphthyridin-8-yl)methyl]piperazin-1-yl}benzonitrile;
46) 3,5-difluoro-4-{4-[(10-methoxy-5-oxo-1,2,3,4,5,6-hexahydrobenzo[h][1,6]naphthyridin-8-yl)methyl]piperazin-1-yl}benzonitrile;
47) 2-fluoro-4-{4-[(10-methoxy-5-oxo-1,2,3,4,5,6-hexahydrobenzo[h]naphthyridin-8-yl)methyl]piperazin-1-yl}benzonitrile;
48) 8-{[4-(4-fluorophenyl)piperazin-1-yl]methyl}-1,2,3,4-tetrahydrobenzo[h][1,6]naphthyridin-5(6H)-one;
49) 8-{[4-(4-fluoro-2-methylphenyl)piperazin-1-yl]methyl}-1,2,3,4-tetrahydrobenzo[h][1,6]naphthyridin-5(6H)-one;
50) 3-fluoro-4-{4-[(5-oxo-1,2,3,4,5,6-hexahydrobenzo[h][1,6]naphthyridin-8-yl)methyl]piperazin-1-yl}benzonitrile;
51) 3-chloro-4-{4-[(5-oxo-1,2,3,4,5,6-hexahydrobenzo[h][1,6]naphthyridin-8-yl)methyl]piperazin-1-yl}benzonitrile;
52) 3-bromo-4-{4-[(5-oxo-1,2,3,4,5,6-hexahydrobenzo[h][1,6]naphthyridin-8-yl)methyl]piperazin-1-yl}benzonitrile;
53) 3-methyl-4-{4-[(5-oxo-1,2,3,4,5,6-hexahydrobenzo[h][1,6]naphthyridin-8-yl)methyl]piperazin-1-yl}benzonitrile;
55) 8-({4-[4-(diethylamino)-2-fluorophenyl]piperazin-1-yl}methyl)-1,2,3,4-tetrahydrobenzo[h][1,6]naphthyridin-5-(6H)-one;
56) 3-acetyl-4-{4-[(5-oxo-1,2,3,4,5,6-hexahydrobenzo[h][1,6]naphthyridin-8-yl)methyl]piperazin-1-yl}benzonitrile;
57) 4-fluoro-2-{4-[(5-oxo-1,2,3,4,5,6-hexahydrobenzo[h][1,6]naphthyridin-8-yl)methyl]piperazin-1-yl}benzonitrile;
58) 3,5-difluoro-4-{4-[(5-oxo-1,2,3,4,5,6-hexahydrobenzo[h][1,6]naphthyridin-8-yl)methyl]piperazin-1-yl}benzonitrile;
59) 8-{[4-(2-fluoro-4-nitrophenyl)piperazin-1-yl]methyl}-1,2,3,4-tetrahydrobenzo[h][1,6]naphthyridin-5(6H)-one;
60) 2-fluoro-4-{4-[(5-oxo-1,2,3,4,5,6-hexahydrobenzo[h][1,6]naphthyridin-8-yl)methyl]piperazin-1-yl}benzonitrile;
61) 2-chloro-4-{4-[(5-oxo-1,2,3,4,5,6-hexahydrobenzo[h][1,6]naphthyridin-8-yl)methyl]piperazin-1-yl}benzonitrile;
62) 4-{4-[(5-oxo-1,2,3,4,5,6-hexahydrobenzo[h][1,6]naphthyridin-8-yl)methyl]piperazin-1-yl}-2-(trifluoromethyl)benzonitrile;
63) 2-methyl-4-{4-[(5-oxo-1,2,3,4,5,6-hexahydrobenzo[h][1,6]naphthyridin-8-yl)methyl]piperazin-1-yl}benzonitrile;
64) N-ethyl-3-methyl-4-{4-[(5-oxo-1,2,3,4,5,6-hexahydrobenzo[h][1,6]naphthyridin-8-yl)methyl]piperazin-1-yl}benzamide;
65) N-cyclopropyl-3-methyl-4-{4-[(5-oxo-1,2,3,4,5,6-hexahydrobenzo[h][1,6]naphthyridin-8-yl)methyl]piperazin-1-yl}benzamide;
66) 3-fluoro-N-methyl-4-{4-[(5-oxo-1,2,3,4,5,6-hexahydrobenzo[h][1,6]naphthyridin-8-yl)methyl]piperazin-1-yl}benzamide;
67) N-ethyl-3-fluoro-4-{4-[(5-oxo-1,2,3,4,5,6-hexahydrobenzo[h][1,6]naphthyridin-8-yl)methyl]piperazin-1-yl}benzamide;
68) N-(3-fluoro-4-{4-[(5-oxo-1,2,3,4,5,6-hexahydrobenzo[h][1,6]naphthyridin-8-yl)methyl]piperazin-1-yl}phenyl)propionamide;
69) N-cyclopropyl-3-fluoro-4-{4-[(5-oxo-1,2,3,4,5,6-hexahydrobenzo[h][1,6]naphthyridin-8-yl)methyl]piperazin-1-yl}benzamide;
70) 3-chloro-N-methyl-4-{4-[(5-oxo-1,2,3,4,5,6-hexahydrobenzo[h]naphthyridin-8-yl)methyl]piperazin-1-yl}benzamide;
71) 3-chloro-N-ethyl-4-{4-[(5-oxo-1,2,3,4,5,6-hexahydrobenzo[h][1,6]naphthyridin-8-yl)methyl]piperazin-1-yl}benzamide;
72) 3-chloro-N-cyclopropyl-4-{4-[(5-oxo-1,2,3,4,5,6-hexahydrobenzo[h][1,6]naphthyridin-8-yl)methyl]piperazin-1-yl}benzamide;
73) 3-bromo-N-methyl-4-{4-[(5-oxo-1,2,3,4,5,6-hexahydrobenzo[h][1,6]naphthyridin-8-yl)methyl]piperazin-1-yl}benzamide;
74) 3-bromo-N-ethyl-4-{(4-[(5-oxo-1,2,3,4,5,6-hexahydrobenzo[h][1,6]naphthyridin-8-yl)methyl]piperazin-1-yl}benzamide;
75) 3-bromo-N-cyclopropyl-4-{4-[(5-oxo-1,2,3,4,5,6-hexahydrobenzo[h]naphthyridin-8-yl)methyl]piperazin-1-yl}benzamide;
76) 2-fluoro-N-methyl-4-{4-[(5-oxo-1,2,3,4,5,6-hexahydrobenzo[h][1,6]naphthyridin-8-yl)methyl]piperazin-1-yl}benzamide;
77) N-ethyl-2-fluoro-4-{(4-[(5-oxo-1,2,3,4,5,6-hexahydrobenzo[h][1,6]naphthyridin-8-yl)methyl]piperazin-1-yl}benzamide;
78) N-cyclopropyl-2-fluoro-4-{4-[(5-oxo-1,2,3,4,5,6-hexahydrobenzo[h][1,6]naphthyridin-8-yl)methyl]piperazin-1-yl}benzamide;
79) N-ethyl-2-fluoro-N-methyl-4-{4-[(5-oxo-1,2,3,4,5,6-hexahydrobenzo[h][1,6]naphthyridin-8-yl)methyl]piperazin-1-yl}benzamide;
80) 2-chloro-N-methyl-4-{(4-[(5-oxo-1,2,3,4,5,6-hexahydrobenzo[h][1,6]naphthyridin-8-yl)methyl]piperazin-1-yl}benzamide;
81) 2-chloro-N-ethyl-4-{4-[(5-oxo-1,2,3,4,5,6-hexahydrobenzo[h][1,6]naphthyridin-8-yl)methyl]piperazin-1-yl}benzamide;
82) 2-chloro-N-cyclopropyl-4-{4-[(5-oxo-1,2,3,4,5,6-hexahydrobenzo[h][1,6]naphthyridin-8-yl)methyl]piperazin-1-yl}benzamide;

83) ethyl 2-chloro-5-(4-[(5-oxo-1,2,3,4,5,6-hexahydrobenzo[h][1,6]naphthyridin-8-yl)methyl]piperazin-1-yl}benzoate;
84) N-ethyl-3,5-difluoro-4-{(4-[(5-oxo-1,2,3,4,5,6-hexahydrobenzo[h][1,6]naphthyridin-8-yl)methyl]piperazin-1-yl}benzamide;
85) N-cyclopropyl-3,5-difluoro-4-{4-[(5-oxo-1,2,3,4,5,6-hexahydrobenzo[h][1,6]naphthyridin-8-yl)methyl]piperazin-1-yl}benzamide;
86) 8-{[4-(pyridin-2-yl)piperazin-1-yl]methyl}-1,2,3,4-tetrahydrobenzo[h][1,6]naphthyridin-5(6H)-one;
87) 8-({(4-[4-(trifluoromethyl)pyridin-2-yl]piperazin-1-yl}methyl)-1,2,3,4-tetrahydrobenzo[h][1,6]naphthyridin-5(6H)-one;
88) 8-({4-[3-(trifluoromethyl)pyridin-2-yl]piperazin-1-yl}methyl)-1,2,3,4-tetrahydrobenzo[h][1,6]naphthyridin-5(6H)-one;
89) 6-{4-[(5-oxo-1,2,3,4,5,6-hexahydrobenzo[h][1,6]naphthyridin-8-yl)methyl]piperazin-1-yl}nicotinonitrile;
90) 8-{[4-(3-methylpyridin-2-yl)piperazin-1-yl]methyl}-1,2,3,4-tetrahydrobenzo[h][1,6]naphthyridin-5(6H)-one;
91) 8-{[4-(5-fluoro-3-methylpyridin-2-yl)piperazin-1-yl]methyl}-1,2,3,4-tetrahydrobenzo[h][1,6]naphthyridin-5(6H)-one;
92) 8-{[4-(pyrazin-2-yl)piperazin-1-yl]methyl}-1,2,3,4-tetrahydrobenzo[h][1,6]naphthyridin-5(6H)-one;
93) 8-{[4-(6-chloropyridazin-3-yl)piperazin-1-yl]methyl}-1,2,3,4-tetrahydrobenzo[h][1,6]naphthyridin-5(6H)-one;
94) 8-{[4-(3,5-dichloropyridin-2-yl)piperazin-1-yl]methyl}-1,2,3,4-tetrahydrobenzo[h][1,6]naphthyridin-5(6H)-one;
95) N-methyl-6-{4-[(5-oxo-1,2,3,4,5,6-hexahydrobenzo[h][1,6]naphthyridin-8-yl)methyl]piperazin-1-yl})nicotinamide;
96) N-ethyl-6-{4-[(5-oxo-1,2,3,4,5,6-hexahydrobenzo[h][1,6]naphthyridin-8-yl)methyl]piperazin-1-yl}nicotinamide;
97) N-cyclopropyl-6-{4-[(5-oxo-1,2,3,4,5,6-hexahydrobenzo[h][1,6]naphthyridin-8-yl)methyl]piperazin-1-yl}nicotinamide;
98) 8-{[4-(thiazol-2-yl)piperazin-1-yl]methyl}-1,2,3,4-tetrahydrobenzo[h][1,6]naphthyridin-5(6H)-one;
99) ethyl-2-{4-[(5-oxo-1,2,3,4,5,6-hexahydrobenzo[h][1,6]naphthyridin-8-yl)methyl]piperazin-1-yl}thiazole-4-carboxylate;
100) N-ethyl-2-{4-[(5-oxo-1,2,3,4,5,6-hexahydrobenzo[h][1,6]naphthyridin-8-yl)methyl]piperazin-1-yl}thiazole-4-carboxamide;
101) 2-fluoro-4-{8-[(5-oxo-1,2,3,4,5,6-hexahydrobenzo[h][1,6]naphthyridin-8-yl)methyl]-3,8-diazabicyclo[3,2,1]octan-3-yl}benzonitrile;
102) 6-{8-[(5-oxo-1,2,3,4,5,6-hexahydrobenzo[h][1,6]naphthyridin-8-yl)methyl]-3,8-diazabicyclo[3,2,1]octan-3-yl}nicotinonitrile;
103) 2-fluoro-4-{(1S,4S)-5-[(5-oxo-1,2,3,4,5,6-hexahydrobenzo[h][1,6]naphthyridin-8-yl)methyl]-2,5-diazabicyclo[2.2.1]heptan-2-yl}benzonitrile;
104) 6-{(1S,4S)-5-[(oxo-1,2,3,4,5,6-hexahydrobenzo[h][1,6]naphthyridin-8-yl)methyl]-2,5-diazabicyclo[2.2.1]heptan-2-yl}nicotinonitrile;
105) 10-ethoxy-8-{[4-(5-fluoropyrimidin-2-yl)-2-methylpiperazin-1-yl]methyl}-1,2,3,4-tetrahydrobenzo[h][1,6]naphthyridin-5(6H)-one;
106) 10-ethoxy-8-{[4-(5-fluoropyridin-2-yl)-2-methylpiperazin-1-yl]methyl}-1,2,3,4-tetrahydrobenzo[h][1,6]naphthyridin-5(6H)-one;
107) 3-fluoro-4-{3-methyl-4-[(5-oxo-1,2,3,4,5,6-hexahydrobenzo[h][1,6]naphthyridin-8-yl)methyl]piperazin-1-yl}benzonitrile;
108) (R)-3-fluoro-4-{3-methyl-4-[(5-oxo-1,2,3,4,5,6-hexahydrobenzo[h][1,6]naphthyridin-8-yl)methyl]piperazin-1-yl}benzonitrile;
109) (S)-3-fluoro-4-{3-methyl-4-[(5-oxo-1,2,3,4,5,6-hexahydrobenzo[h][1,6]naphthyridin-8-yl)methyl]piperazin-1-yl}benzonitrile;
110) (R)-3-fluoro-4-{2-methyl-4-[(5-oxo-1,2,3,4,5,6-hexahydrobenzo[h][1,6]naphthyridin-8-yl)methyl]piperazin-1-yl}benzonitrile;
111) 2-fluoro-4-{3-methyl-4-[(5-oxo-1,2,3,4,5,6-hexahydrobenzo[h][1,6]naphthyridin-8-yl)methyl]piperazin-1-yl}benzonitrile;
112) (R)-2-fluoro-4-{3-methyl-4-[(5-oxo-1,2,3,4,5,6-hexahydrobenzo[h][1,6]naphthyridin-8-yl)methyl]piperazin-1-yl}benzonitrile;
113) (S)-2-fluoro-4-{3-methyl-4-[(5-oxo-1,2,3,4,5,6-hexahydrobenzo[h][1,6]naphthyridin-8-yl)methyl]piperazin-1-yl}benzonitrile;
114) (R)-2-fluoro-4-{2-methyl-4-[(5-oxo-1,2,3,4,5,6-hexahydrobenzo[h][1,6]naphthyridin-8-yl)methyl]piperazin-1-yl}benzonitrile;
115) 8-({(4-[4-(trifluoromethyl)phenyl]piperazin-1-yl}methyl)-1,2,3,4-tetrahydrobenzo[h][1,2]naphthyridin-5(6H)-one;
116) 6-{4-[(10-ethoxy-5-oxo-1,2,3,4,5,6-hexahydrobenzo[h][1,6]naphthyridin-8-yl)methyl]piperazin-1-yl}nicotinonitrile;
117) 8-({{4-[2-chloro-4-(trifluoromethyl)phenyl]piperazin-1-yl}methyl)-1,2,3,4-tetrahydrobenzo[h][1,6]naphthyridin-5(6H)-one;
118) 8-({{4-[3-chloro-4-(trifluoromethyl)phenyl]piperazin-1-yl}methyl)-1,2,3,4-tetrahydrobenzo[h][1,6]naphthyridin-5(6H)-one;
119) 8-{[4-(3-fluoro-4-nitrophenyl)piperazin-1-yl]methyl}-1,2,3,4-tetrahydrobenzo[h][1,6]naphthyridin-5(6H)-one;
120) 8-{[4-(5-chloropyridin-2-yl)piperazin-1-yl]methyl}-1,2,3,4-tetrahydrobenzo[h][1,6]naphthyridin-5(6H)-one;
121) 8-({4-[5-(trifluoromethyl)pyridin-2-yl]piperazin-1-yl}methyl)-1,2,3,4-tetrahydrobenzo[h][1,6]naphthyridin-5(6H)-one;
122) 8-({4-[5-(methylsulfonyl)pyridin-2-yl]piperazin-1-yl}methyl)-1,2,3,4-tetrahydrobenzo[h][1,6]naphthyridin-5(6H)-one;
123) 5-{4-[(5-oxo-1,2,3,4,5,6-hexahydrobenzo[h][1,6]naphthyridin-8-yl)methyl]piperazin-1-yl}picolinonitrile;
124) 2-{4-[(5-oxo-1,2,3,4,5,6-hexahydrobenzo[h][1,6]naphthyridin-8-yl)methyl]piperazin-1-yl}isonicotinonitrile;
125) 2-{4-[(5-oxo-1,2,3,4,5,6-hexahydrobenzo[h][1,6]naphthyridin-8-yl)methyl]piperazin-1-yl}nicotinonitrile;
126) 6-{4-[(5-oxo-1,2,3,4,5,6-hexahydrobenzo[h][1,6]naphthyridin-8-yl)methyl]piperazin-1-yl}picolinonitrile;
127) 8-{[4-(4-methoxypyridin-2-yl)piperazin-1-yl]methyl}-1,2,3,4-tetrahydrobenzo[h][1,6]naphthyridin-5(6H)-one;

128) 8-({4-[5-(methoxymethyl)-pyridin-2-yl]piperazin-1-yl}methyl)-1,2,3,4-tetrahydrobenzo[h][1,6]naphthyridin-5(6H)-one;
129) 5-{4-[(5-oxo-1,2,3,4,5,6-hexahydrobenzo[h][1,6]naphthyridin-8-yl)methyl]piperazin-1-yl}pyrazine-2-carbonitrile;
130) 8-{[4-(6-methylpyridazin-3-yl)piperazin-1-yl]methyl}-1,2,3,4-tetrahydrobenzo[h][1,6]naphthyridin-5(6H)-one;
131) 8-{[4-(6-methoxypyridazin-3-yl)piperazin-1-yl]methyl}-1,2,3,4-tetrahydrobenzo[h][1,6]naphthyridin-5(6H)-one;
132) 6-{4-[(5-oxo-1,2,3,4,5,6-hexahydrobenzo[h][1,6]naphthyridin-8-yl)methyl]piperazin-1-yl}pyridazine-3-carbonitrile;
133) 5-chloro-6-{4-[(5-oxo-1,2,3,4,5,6-hexahydrobenzo[h][1,6]naphthyridin-8-yl)methyl]piperazin-1-yl}nicotinonitrile;
134) 6-chloro-4-{4-[(5-oxo-1,2,3,4,5,6-hexahydrobenzo[h][1,6]naphthyridin-8-yl)methyl]piperazin-1-yl}nicotinonitrile;
135) 4-chloro-6-{4-[(5-oxo-1,2,3,4,5,6-hexahydrobenzo[h][1,6]naphthyridin-8-yl)methyl]piperazin-1-yl}nicotinonitrile;
136) 5-chloro-2-{4-[(5-oxo-1,2,3,4,5,6-hexahydrobenzo[h][1,6]naphthyridin-8-yl)methyl]piperazin-1-yl}isonicotinonitrile;
137) 4-methoxy-6-{4-[(5-oxo-1,2,3,4,5,6-hexahydrobenzo[h][1,6]naphthyridin-8-yl)methyl]piperazin-1-yl}nicotinonitrile;
138) 8-{[4-(5-bromo-4-methoxypyridin-2-yl)piperazin-1-yl]methyl}-1,2,3,4-tetrahydrobenzo[h][1,6]naphthyridin-5(6H)-one;
139) 2-{4-[(5-oxo-1,2,3,4,5,6-hexahydrobenzo[h][1,6]naphthyridin-8-yl)methyl]piperazin-1-yl}thiazole-4-carbonitrile;
140) 5-{4-[(5-oxo-1,2,3,4,5,6-hexahydrobenzo[h][1,6]naphthyridin-8-yl)methyl]piperazin-1-yl}thiophene-2-carbonitrile;
141) ethyl-2-{4-[((5-oxo-1,2,3,4,5,6-hexahydrobenzo[h][1,6]naphthyridin-8-yl)methyl]piperazin-1-yl}thiazole-5-carboxylate;
142) 2-{4-[(5-oxo-1,2,3,4,5,6-hexahydrobenzo[h][1,6]naphthyridin-8-yl)methyl]piperazin-1-yl}thiazole-5-carbonitrile;
143) 5-{4-[(5-oxo-1,2,3,4,5,6-hexahydrobenzo[h][1,6]naphthyridin-8-yl)methyl]piperazin-1-yl}-1,3,4-thiadiazole-2-carbonitrile;
144) 2-{4-[(5-oxo-1,2,3,4,5,6-hexahydrobenzo[h][1,6]naphthyridin-8-yl)methyl]piperazin-1-yl}oxazole-4-carbonitrile;
145) 5-{4-[(5-oxo-1,2,3,4,5,6-hexahydrobenzo[h][1,6]naphthyridin-8-yl)methyl]piperazin-1-yl}-1,2,4-thiadiazole-3-carbonitrile;
146) 5-{4-[(5-oxo-1,2,3,4,5,6-hexahydrobenzo[h][1,6]naphthyridin-8-yl)methyl]piperazin-1-yl}-1,3,4-oxadiazole-2-carbonitrile;
147) 8-{[4-(5-chlorobenzo[d]oxazol-2-yl)piperazin-1-yl]methyl}-1,2,3,4-tetrahydrobenzo[h][1,6]naphthyridin-5(6H)-one;
148) 8-{[4-(2-methylbenzo[d]oxazol-6-yl)piperazin-1-yl]methyl}-1,2,3,4-tetrahydrobenzo[h][1,6]naphthyridin-5(6H)-one;
149) 8-{[4-(3-methylbenzo[d]isoxazol-5-yl)piperazin-1-yl]methyl}-1,2,3,4-tetrahydrobenzo[h][1,6]naphthyridin-5(6H)-one;
150) 8-{[4-(1H-indol-6-yl)piperazin-1-yl]methyl}-1,2,3,4-tetrahydrobenzo[h][1,6]naphthyridin-5(6H)-one;
151) 8-{[4-(1H-indazol-5-yl)piperazin-1-yl]methyl}-1,2,3,4-tetrahydrobenzo[h][1,6]naphthyridin-5(6H)-one;
152) 8-{[4-(1H-indazol-6-yl)piperazin-1-yl]methyl}-1,2,3,4-tetrahydrobenzo[h][1,6]naphthyridin-5(6H)-one;
153) 8-{[4-(benzo[d]isoxazol-5-yl)piperazin-1-yl]methyl}-1,2,3,4-tetrahydrobenzo[h][1,6]naphthyridin-5(6H)-one;
154) 8-{[4-(oxazolo[4,5-b]pyridin-2-yl)piperazin-1-yl]methyl}-1,2,3,4-tetrahydrobenzo[h][1,6]naphthyridin-5(6H)-one;
155) 8-{[4-(oxazolo[5,4-b]pyridin-2-yl)piperazin-1-yl]methyl}-1,2,3,4-tetrahydrobenzo[h][1,6]naphthyridin-5(6H)-one;
156) 8-{[4-(2,3-dihydrofuro[2,3-b]pyridin-6-yl)piperazin-1-yl]methyl}-1,2,3,4-tetrahydrobenzo[h][1,6]naphthyridin-5(6H)-one;
157) 1-{4-[(5-oxo-1,2,3,4,5,6-hexahydrobenzo[h][1,6]naphthyridin-8-yl)methyl]piperazin-1-yl}-6,7-dihydro-5H-cyclopenta[c]pyridine-4-carbonitrile;
158) 8-{[3-(pyrazin-2-yl)-3,8-diazabicyclo[3.2.1]octan-8-yl]methyl}-1,2,3,4-tetrahydrobenzo[h][1,6]naphthyridin-5(6H)-one;
159) 6-{3-[(5-oxo-1,2,3,4,5,6-hexahydrobenzo[h][1,6]naphthyridin-8-yl)methyl]-3,8-diazabicyclo[3.2.1]octan-8-yl)nicotinonitrile;
160) 8-{[3-(6-chloropyridazin-3-yl)-3,8-diazabicyclo[3.2.1]octan-8-yl]methyl}-1,2,3,4-tetrahydrobenzo[h][1,6]naphthyridin-5(6H)-one;
161) 3-fluoro-4-{(1 S,4S)-5-[(5-oxo-1,2,3,4,5,6-hexahydrobenzo[h][1,6]naphthyridin-8-yl)methyl]-2,5-diazabicyclo[2.2.1]heptan-2-yl}benzonitrile;
162) 8-{[(1 S,4S)-5-(2-fluoro-4-nitrophenyl)-2,5-diazabicyclo[2.2.1]heptan-2-yl]methyl) 1,2,3,4-tetrahydrobenzo[h][1,6]naphthyridin-5(6H)-one;
163) 8-{[(1 S,4S)-5-(6-chloropyridazin-3-yl)-2,5-diazabicyclo[2.2.1]heptan-2-yl]methyl}-10-fluoro-1,2,3,4-tetrahydrobenzo[h][1,6]naphthyridin-5(6H)-one;
164) 10-fluoro-8-{[(1 S,4S)-5-(pyridazin-2-yl)-2,5-diazabicyclo[2.2.1]heptan-2-yl]methyl}-1,2,3,4-tetrahydrobenzo[h][1,6]naphthyridin-5(6H)-one;
165) (S)-2-fluoro-4-{2-methyl-4-[(5-oxo-1,2,3,4,5,6-hexahydrobenzo[h][1,6]naphthyridin-8-yl)methyl]piperazin-1-yl}benzonitrile;
166) 10-fluoro-8-{[4-(2-fluoro-4-nitrophenyl)piperazin-1-yl]methyl}-1,2,3,4-tetrahydrobenzo[h][1,6]naphthyridin-5(6H)-one;
167) 10-fluoro-8-{[4-(pyridin-2-yl)piperazin-1-yl]methyl}-1,2,3,4-tetrahydrobenzo[h][1,6]naphthyridin-5(6H)-one;
168) 10-fluoro-8-{[4-(3-methylpyridin-2-yl)piperazin-1-yl]methyl}-1,2,3,4-tetrahydrobenzo[h][1,6]naphthyridin-5(6H)-one;
169) 10-fluoro-8-{[4-(5-fluoropyridin-2-yl)piperazin-1-yl]methyl}-1,2,3,4-tetrahydrobenzo[h][1,6]naphthyridin-5(6H)-one;
170) 6-{4-[(1-fluoro-5-oxo-1,2,3,4,5,6-hexahydrobenzo[h][1,6]naphthyridin-8-yl]methyl}piperazin-1-yl)nicotinonitrile;
171) 2-{4-[(10-fluoro-5-oxo-1,2,3,4,5,6-hexahydrobenzo[h][1,6]naphthyridin-8-yl]methyl}piperazin-1-yl)thiazole-5-carbonitrile;
172) 10-fluoro-8-{[4-(4-fluorphenyl)piperazin-1-yl]methyl}-1,2,3,4-tetrahydrobenzo[h][1,6]naphthyridin-5(6H)-one;

173) 2-fluoro-4-{[4-(1-fluoro-5-oxo-1,2,3,4,5,6-hexahydrobenzo[h][1,6]naphthyridin-8-yl]methyl}piperazin-1-yl)benzonitrile;
174) 4-{[4-(1-fluoro-5-oxo-1,2,3,4,5,6-hexahydrobenzo[h][1,6]naphthyridin-8-yl]methyl}piperazin-1-yl)-2-(trifluoromethyl)benzonitrile;
175) 10-fluoro-8-{[4-(4-fluoro-2-methylphenyl)piperazin-1-yl]methyl}-1,2,3,4-tetrahydrobenzo[h][1,6]naphthyridin-5(6H)-one;
176) 3-fluoro-4-{4-[(1-fluoro-5-oxo-1,2,3,4,5,6-hexahydrobenzo[h][1,6]naphthyridin-8-yl]methyl}piperazin-1-yl)benzonitrile;
177) 6-f (1 S,4S)-5-[(1-fluoro-5-oxo-1,2,3,4,5,6-hexahydrobenzo[h][1,6]naphthyridin-8-yl)methyl]-2,5-diazabicyclo[2.2.1]heptan-2-yl}nicotinonitrile;
178) 10-fluoro-8-{[4-(pyrazin-2-yl)piperazin-1-yl]methyl}-1,2,3,4-tetrahydrobenzo[h][1,6]naphthyridin-5(6H)-one;
179) 8-{[4-(5-chloropyridin-2-yl)piperazin-1-yl]methyl}-10-fluoro-1,2,3,4-tetrahydrobenzo[h][1,6]naphthyridin-5(6H)-one;
180) 5-{4-[(1-fluoro-5-oxo-1,2,3,4,5,6-hexahydrobenzo[h][1,6]naphthyridin-8-yl)methyl]piperazin-1-yl}picolinonitrile;
181) 8-{[4-(6-chloropyridazin-3-yl)piperazin-1-yl]methyl})-10-fluoro-1,2,3,4-tetrahydrobenzo[h][1,6]naphthyridin-5(6H)-one;
182) 6-{4-[(10-fluoro-5-oxo-1,2,3,4,5,6-hexahydrobenzo[h][1,6]naphthyridin-8-yl)methyl]piperazin-1-yl}pyridazine-3-carbonitrile;
183) 5-{4-[(10-fluoro-5-oxo-1,2,3,4,5,6-hexahydrobenzo[h][1,6]naphthyridin-8-yl)methyl]piperazin-1-yl}thiophene-2-carbonitrile;
184) 6-{8-[(10-fluoro-5-oxo-1,2,3,4,5,6-hexahydrobenzo[h][1,6]naphthyridin-8-yl)methyl]-3,8-diazabicyclo[3,2,1]octan-3-yl}nicotinonitrile;
185) 4-{4-[(10-fluoro-5-oxo-1,2,3,4,5,6-hexahydrobenzo[h][1,6]naphthyridin-8-yl)methyl]piperazin-1-yl}-3-methoxybenzonitrile;
186) 5-[4-(5-oxo-1,2,3,4,5,6-hexahydrobenzo[h][1,6]naphthyridin-8-carbonyl)piperazin-1-yl]thiophene-2-carbonitrile;
187) 6-[4-(5-oxo-1,2,3,4,5,6-hexahydrobenzo[h][1,6]naphthyridin-8-carbonyl)piperazin-1-yl]nicotinonitrile;
188) 2-[4-(5-oxo-1,2,3,4,5,6-hexahydrobenzo[h][1,6]naphthyridin-8-carbonyl)piperazin-1-yl]thiazole-4-carbonitrile; and
189) 2-[4-(5-oxo-1,2,3,4,5,6-hexahydrobenzo[h][1,6]naphthyridin-8-carbonyl)piperazin-1-yl]thiazole-5-carbonitrile.

6. A method for preparing a tricyclic compound represented by the following formula 1a, an optical isomer thereof, a racemate thereof or a pharmaceutically acceptable salt thereof, the method comprising the steps of:
(1) preparing an acid chloride using a reagent that converts a nicotinic acid compound of formula 2 to the acid chloride, and subjecting the acid chloride to an amidation reaction with an aniline of formula 3, or subjecting the nicotinic acid compound of formula 2 to a coupling reaction with the aniline of formula 3, thereby preparing a compound of formula 4;
(2) introducing a protection group into the compound of formula 4, prepared in step (1), thereby preparing an N-protected compound of formula 5;
(3) cyclizing the compound of formula 5, prepared in step (2), in the presence of a metal catalyst, thereby preparing a compound of formula 6;
(4) subjecting the compound of formula 6, prepared in step (3), to a ring-reducing reaction with hydrogen in the presence of a palladium catalyst, thereby preparing a compound of formula 7;
(5) reducing the compound of formula 7, prepared in step (4), with a reducing agent, thereby preparing a compound of formula 8;
(6) subjecting the compound of formula 8, prepared in step (5), to halogenation and an amination reaction with an amine compound, thereby preparing a compound of formula 9; and
(7) removing the protection group from the compound of formula 9, prepared in step (6), by a deprotection reaction, thereby preparing a compound of formula 1a

[Reaction Scheme 1]

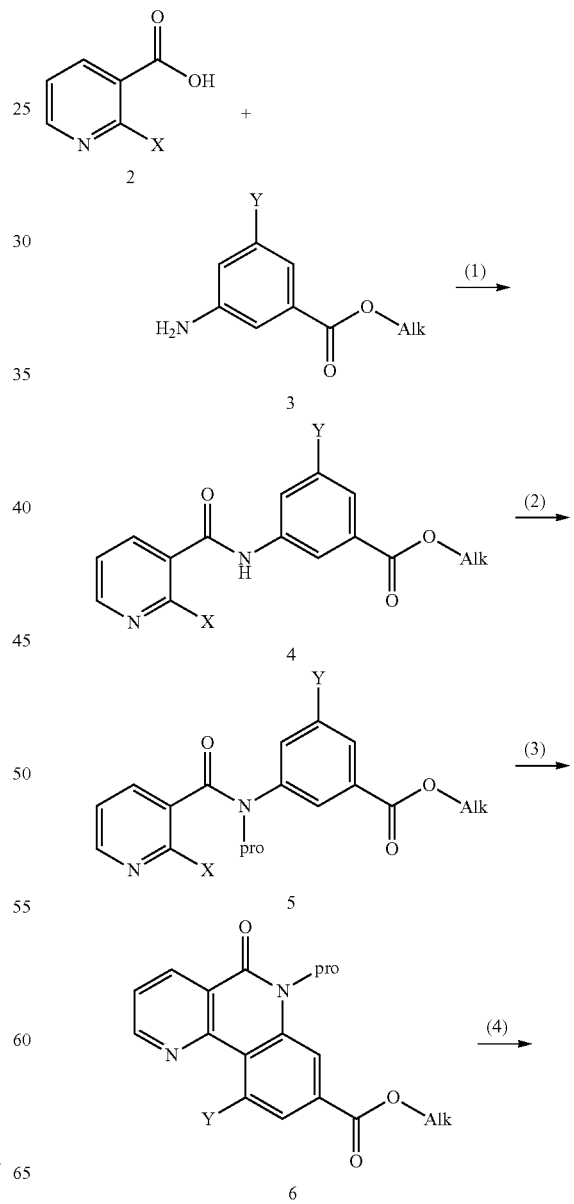

-continued

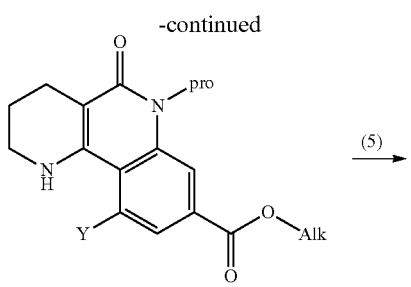
7

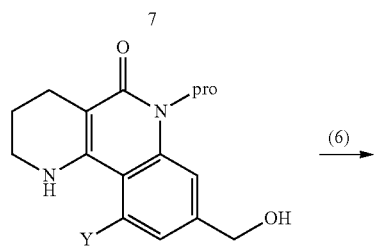
8

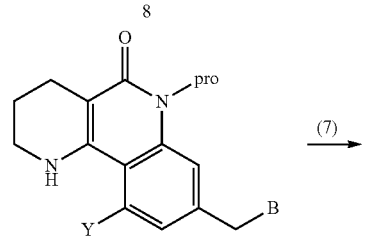
9

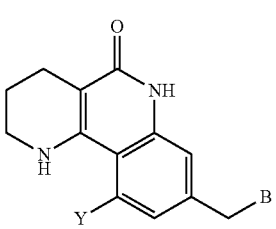
1a wherein
X is a halogen atom;
Y is He, C₁-C₃ alkoxy or a halogen atom;
Alk is a C₁-C₁₀ straight or branched chain alkyl;
pro is a protection group selected from the group consisting of an aryl group, a benzyl group, a benzyloxymethyl group, a para-methoxybenzyl group and a methoxymethyl group; and
B is

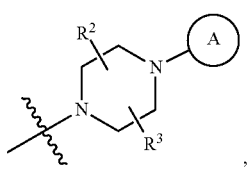

wherein ring A, R² and R³ are as defined in claim 1.

7. A method for preparing a tricyclic compound represented by the following formula 1a, an optical isomer thereof, a racemate thereof or a pharmaceutically acceptable salt thereof, the method comprising the steps of:

(1) removing a protection group from a compound of formula 8 by a deprotection reaction, thereby preparing a compound of formula 10; and
(2) subjecting the compound of formula 10, prepared in step (1), to halogenation and an amination reaction with an amine compound, thereby preparing a compound of formula 1a

[Reaction Scheme 2]

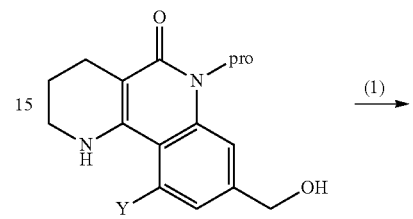
8

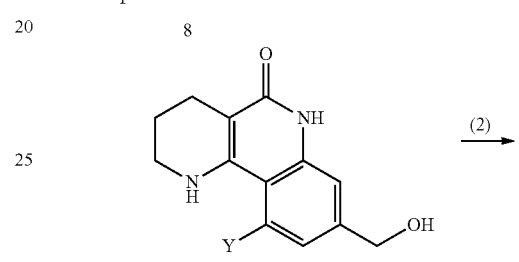
10

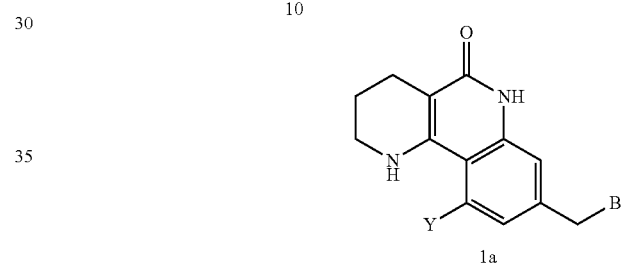
1a wherein
Y is H, C₁-C₃ alkoxy or a halogen atom;
pro is a protection group selected from the group consisting of an aryl group, a benzyl group, a benzyloxymethyl group, a para-methoxybenzyl group and a methoxymethyl group; and
B is

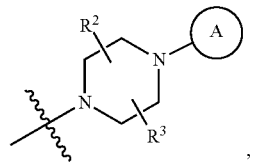

wherein ring A, R² and R³ are as defined in claim 1.

8. A method for preparing a tricyclic compound represented by the following formula 1b, an optical isomer thereof, a racemate thereof or a pharmaceutically acceptable salt thereof, the method comprising the steps of:

(1) removing a protection group from a compound of formula 7 by a deprotection reaction, thereby preparing a compound of formula 11;
(2) adding an aqueous solution of potassium hydroxide or sodium hydroxide slowly dropwise to the compound of formula 11, prepared in step (1), thereby preparing a compound of formula 12, which is a hydrolyzed carboxylic acid; and (3) subjecting the compound of formula 12, prepared in step (2), to a coupling reaction with an amine compound, thereby preparing a compound of formula 1b

[Reaction Scheme 3]

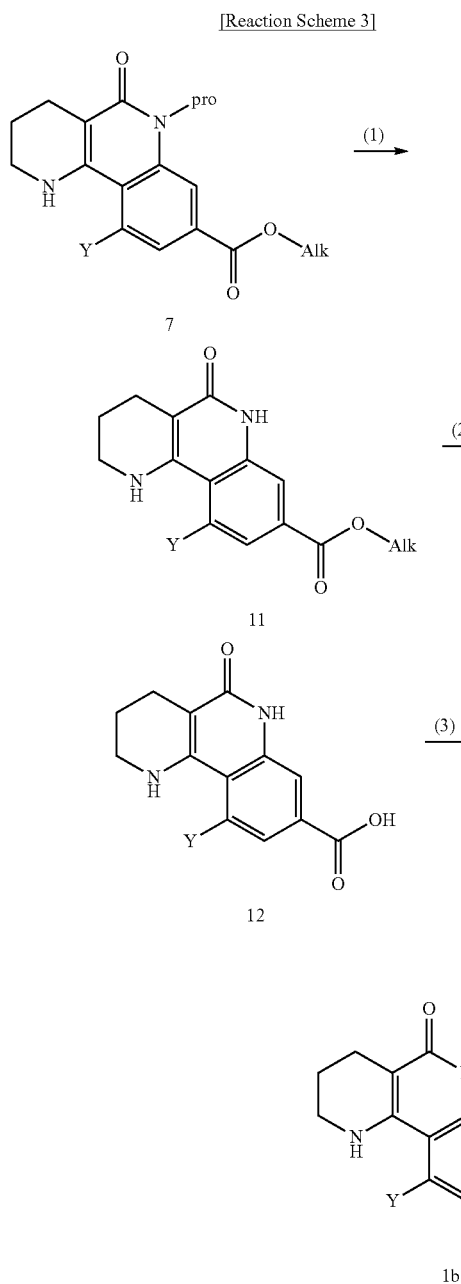

wherein

Y is H, $C_1$-$C_3$ alkoxy or a halogen atom;

Alk is a $C_1$-$C_{10}$ straight or branched chain alkyl;

pro is a protection group selected from the group consisting of an aryl group, a benzyl group, a benzyloxymethyl group, a para-methoxybenzyl group and a methoxymethyl group; and B is

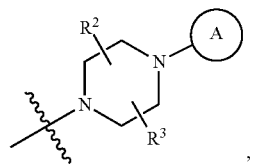

wherein ring A, $R^2$ and $R^3$ are as defined in claim 1.

9. A pharmaceutical composition, comprising a tricyclic compound according to claim 1, an optical isomer thereof, the racemate thereof or a pharmaceutically acceptable salt thereof; and
a pharmaceutically acceptable carrier.

10. The tricyclic compound, the optical isomer thereof, the racemate thereof or the pharmaceutically acceptable salt according to claim 1, wherein
L is —$CH_2$— or —C(=O)—;
$R^1$ is H, a halogen atom or $C_1$-$C_3$ alkoxy;
$R^2$ and $R^3$ are each independently H or $C_1$-$C_3$ alkyl, or $R^2$ and $R^3$ are linked to each other to form a ring;
ring A phenyl or a heteroaryl selected from the group consisting of pyridine, pyrazine, pyrimidine, pyridazine, thiophene, thiazole, thiadiazole, oxazole, oxadiazole, indole, indazole, cyclopentapyridine, dihydrocyclopentapyridine, furopyridine, dihydrofuropyridine, oxazolopyridine, benzoxazole, and benzoisoxazole,
wherein one or more H atoms of the phenyl is substituted with a substituent selected from the group consisting of a halogen atom, —CN, —$CF_3$, —$C_1$-$C_3$ alkyl, —$C_1$-$C_3$ alkoxy, —C(=O)—$R^4$, —C(=O)—$OR^4$, —S(=O)$_2$—$R^4$, —NH—C(=O)—$R^4$, —$NO_2$, —$NR^4R^5$ and —C(=O)—$NR^6R^7$, and the heteroaryl is unsubstituted, or one or more H atoms of the heteroaryl is substituted with a substituent selected from the group consisting of a halogen atoms, —CN, —$CF_3$, —$C_1$-$C_3$ alkyl, —$C_1$-$C_3$ alkoxy, —$CH_2$—$OR^4$, —C(=O)—$OR^4$, —S(=O)$_2$—$R^4$, —$NO_2$, —$NR^4R^5$ and —C(=O)—$NR^6R^7$
$R^4$ is $C_1$-$C_3$ alkyl;
$R^5$ is H or $C_1$-$C_3$ alkyl;
$R^6$ is H or $C_1$-$C_3$ alkyl; and
$R^7$ is $C_1$-$C_3$ alkyl or $C_3$-$C_7$ cycloalkyl.

11. The tricyclic compound, the optical isomer thereof, the racemate thereof or the pharmaceutically acceptable salt according to claim 10, wherein
L is —$CH_2$— or —C(=O)—;
$R^1$ is H or a halogen atom or $C_1$-$C_3$ alkoxy;
$R^2$ and $R^3$ are each independently H or $C_1$-$C_3$ alkyl, or $R^2$ and $R^3$ are linked to each other to form a ring;
ring A is the phenyl or the heteroaryl selected from the group consisting of pyridine, pyrazine, pyrimidine, pyridazine, thiophene, thiazole, thiadiazole, indole, indazole, cyclopentapyridine, dihydrocyclopentapyridine, dihydrofuropyridine, oxazolopyridine, benzoxazole, and benzoisoxazole,
wherein one or more H atoms of the phenyl is substituted with a substituent selected from the group consisting or a halogen atom, —CN, —$CF_3$, —$C_1$-$C_3$ alkyl, —$C_1$-$C_3$ alkoxy, —C(=O)—$R^4$, —C(=O)—$OR^4$, —NH—C(=O)—$R^4$, —$NO_2$, —$NR^4R^5$ and —C(=O)—$NR^6R^7$, and the heteroaryl is unsubstituted, or one or more H atoms of the heteroaryl is substituted with a substituent selected from the group consisting of a halogen atom, —CN, —CF$_3$, —C$_1$-C$_3$ alkyl, —C$_1$-C$_3$ alkoxy, —CH$_2$—OR$^4$, —C(=O)—OR$^4$, —S(=O)$_2$—R$^4$ and —C(=O)—NR$^6$R$^7$ R$^4$ is C$_1$-C$_3$ alkyl;
R$^5$ is H or C$_1$-C$_3$ alkyl;
R$^6$ is H or C$_1$-C$_3$ alkyl; and
R$^7$ is C$_1$-C$_3$ alkyl or C$_3$-C$_7$ cycloalkyl.

* * * * *

UNITED STATES PATENT AND TRADEMARK OFFICE
CERTIFICATE OF CORRECTION

PATENT NO. : 10,464,919 B2
APPLICATION NO. : 15/579692
DATED : November 5, 2019
INVENTOR(S) : Hyunho Lee et al.

It is certified that error appears in the above-identified patent and that said Letters Patent is hereby corrected as shown below:

In the Claims

Column 106, Lines 60-61, Claim 1, delete "benzoisoxazole." and insert -- benzoisoxazole, --;

Column 107, Line 31, Claim 5, delete "-({[4-" and insert -- -{[4- --;

Column 107, Lines 57-58, Claim 5, delete "-tretrahydrobenzo" and insert -- -tetrahydrobenzo --;

Column 108, Line 8, Claim 5, delete "piperzin-1-yl})-" and insert -- piperazin-1-yl}- --;

Column 108, Line 23, Claim 5, delete "-[(1-" and insert -- -[(10- --;

Column 108, Line 27, Claim 5, delete "[h]" and insert -- [h][1,6] --;

Column 108, Line 65, Claim 5, delete "-[(1-" and insert -- -[(10- --;

Column 109, Line 13 (approx.), Claim 5, delete "-[(1-" and insert -- -[(10- --;

Column 109, Line 24, Claim 5, delete "[h]" and insert -- [h][1,6] --;

Column 109, Line 31 (approx.), Claim 5, delete "[h]" and insert -- [h][1,6] --;

Column 109, Line 49, Claim 5, below "yl}benzonitrile;" insert -- 54) 3-methoxy-4-{4-[(5-oxo-1,2,3,4,5,6-hexahydrobenzo[h][1,6]naphthyridin-8-yl)methyl]piperazin-1-yl}benzonitrile; --;

Column 110, Line 30, Claim 5, delete "[h]" and insert -- [h][1,6] --;

Column 110, Line 41, Claim 5, delete "-{(4-" and insert -- -{4- --;

Column 110, Line 45, Claim 5, delete "[h]" and insert -- [h][1,6] --;

Signed and Sealed this
Twenty-first Day of July, 2020

Andrei Iancu
*Director of the United States Patent and Trademark Office*

CERTIFICATE OF CORRECTION (continued)
U.S. Pat. No. 10,464,919 B2

Column 110, Line 50, Claim 5, delete "-{(4-" and insert -- -{4- --;

Column 110, Line 59, Claim 5, delete "-{(4-" and insert -- -{4- --;

Column 111, Line 1, Claim 5, delete "-(4-" and insert -- -{4- --;

Column 111, Line 4, Claim 5, delete "-{(4-" and insert -- -{4- --;

Column 111, Line 12, Claim 5, delete "-({(4-" and insert -- -({4- --;

Column 111, Line 37, Claim 5, delete "-yl})" and insert -- -yl} --;

Column 112, Line 29, Claim 5, delete "-({(4-" and insert -- -({4- --;

Column 112, Line 35, Claim 5, delete "-({(4-" and insert -- -({4- --;

Column 112, Line 38, Claim 5, delete "-({(4-" and insert -- -({4- --;

Column 114, Line 32, Claim 5, delete "-{(1 S," and insert -- -{(1S, --;

Column 114, Line 35, Claim 5, delete "8-{[(1 S," and insert -- 8-{[(1S, --;

Column 114, Line 36, Claim 5, delete ") 1," and insert -- }-1, --;

Column 114, Line 38, Claim 5, delete "8-{[(1 S," and insert -- 8-{[(1S, --;

Column 114, Line 41, Claim 5, delete "-8-{[(1 S," and insert -- -8-{[(1S, --;

Column 114, Line 59, Claim 5, delete "-[(1-" and insert -- -[(10- --;

Column 115, Line 1, Claim 5, delete "-(1-" and insert -- -(10- --;

Column 115, Line 4, Claim 5, delete "-(1-" and insert -- -(10- --;

Column 115, Line 11 (approx.), Claim 5, delete "-[(1-" and insert -- -[(10- --;

Column 115, Line 13 (approx.), Claim 5, delete "6-f(1 S,4S)-5-[(1-" and insert -- 6-{(1S,4S)-5-[(10- --;

Column 115, Line 23, Claim 5, delete "-[(1-" and insert -- -[(10- --;

Column 115, Line 27, Claim 5, delete "methyl})-" and insert -- methyl}- --;

Column 117, Line 45, Claim 6, delete "He," and insert -- H, --;

Column 120, Line 24, Claim 10, after "A" insert -- is --;

Column 120, Line 39, Claim 10, delete "atoms," and insert -- atom, --.